US010744295B2

(12) United States Patent
Kenyon et al.

(10) Patent No.: US 10,744,295 B2
(45) Date of Patent: Aug. 18, 2020

(54) RESPIRATORY THERAPY APPARATUS

(71) Applicant: ResMed Pty Ltd, Bella Vista, New South Wales (AU)

(72) Inventors: Barton John Kenyon, Sydney (AU); Timothy Nicholas Shadie, Sydney (AU); Cem Tarakci, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 1236 days.

(21) Appl. No.: 14/993,351

(22) Filed: Jan. 12, 2016

(65) Prior Publication Data

US 2016/0199607 A1    Jul. 14, 2016

(30) Foreign Application Priority Data

Jan. 13, 2015  (AU) ................ 2015900075
Jan. 19, 2015  (AU) ................ 2015900138
Jul. 2, 2015   (AU) ................ 2015902607

(51) Int. Cl.
*A61M 16/00*       (2006.01)
*F04B 45/04*       (2006.01)
(Continued)

(52) U.S. Cl.
CPC ...... *A61M 16/207* (2014.02); *A61M 16/0066* (2013.01); *F04B 45/043* (2013.01);
(Continued)

(58) Field of Classification Search
CPC ...... F04B 43/02; F04B 43/025; F04B 43/026; F04B 43/04; F04B 43/043; F04B 43/046; F04B 45/04; F04B 45/043; F04B 45/045; A61B 9/02–027; A61B 9/00; A61M 16/00; A61M 16/06–0694; A61M 16/20–209; A61M 16/0003–0012;
(Continued)

(56) References Cited

U.S. PATENT DOCUMENTS 4,782,832 A   11/1988  Trimble et al.
4,944,310 A    7/1990  Sullivan
(Continued)

FOREIGN PATENT DOCUMENTS

EP      2 610 602 A2    7/2013
WO      WO 98/04310 A1  2/1998
(Continued)

OTHER PUBLICATIONS

West, John B., "Respiratory Physiology", Lippincott Williams & Wilkins, 9th edition published 2012, 8 pages.

*Primary Examiner* — Samchuan C Yao
*Assistant Examiner* — Ned T Heffner
(74) *Attorney, Agent, or Firm* — Nixon & Vanderhye P.C.

(57) ABSTRACT

A blower comprises a housing, an inlet to receive air, an outlet to deliver a flow of air and a deformable member configured to pump a chamber. The deformable member may be configurable to a first configuration and a second configuration, for example by electrical energy that may be applied as current or voltage. The blower may comprise a plurality of chambers, wherein each chamber may be compressed out of phase with each other, for example such that the flow rate of the generated air flow may not fluctuate as much. In other forms, the blower may comprise a plurality of chambers that vary in size.

26 Claims, 39 Drawing Sheets

(51) Int. Cl.
  *A61M 16/20* (2006.01)
  *A61M 16/16* (2006.01)

(52) U.S. Cl.
  CPC ............ *F04B 45/045* (2013.01); *A61M 16/16* (2013.01); *A61M 2016/003* (2013.01); *A61M 2016/0027* (2013.01); *A61M 2205/3334* (2013.01); *A61M 2205/3365* (2013.01); *A61M 2205/42* (2013.01)

(58) Field of Classification Search
  CPC ... A61M 2016/0015–0042; A62B 7/00; A62B 7/04; A62B 7/14; B63C 11/12; B63C 11/18
  See application file for complete search history.

(56) References Cited

U.S. PATENT DOCUMENTS

| | | | |
|---|---|---|---|
| 5,250,167 | A | 10/1993 | Adolf et al. |
| 5,488,255 | A | 1/1996 | Sato et al. |
| 5,921,757 | A | 7/1999 | Tsutsui et al. |
| 6,532,959 | B1 | 3/2003 | Berthon-Jones |
| 6,581,594 | B1 | 6/2003 | Drew et al. |
| 6,910,483 | B2 | 6/2005 | Daly et al. |
| 7,064,472 | B2 | 6/2006 | Pelrine et al. |
| 7,394,182 | B2 | 7/2008 | Pelrine et al. |
| 7,550,034 | B2 | 6/2009 | Janse Van Rensburg et al. |
| 7,553,135 | B2 | 6/2009 | Cho et al. |
| 7,866,944 | B2 | 1/2011 | Kenyon et al. |
| 8,081,454 | B2 | 12/2011 | Ishikawa et al. |
| 8,267,648 | B2 | 9/2012 | Kenyon et al. |
| 8,596,998 | B2 | 12/2013 | Fujisaki et al. |
| 8,636,479 | B2 | 1/2014 | Kenyon et al. |
| 8,638,014 | B2 | 1/2014 | Sears et al. |
| 8,678,787 | B2 | 3/2014 | Hirata et al. |
| 8,842,355 | B2 | 9/2014 | Lipton et al. |
| 2003/0117044 | A1* | 6/2003 | Urano ................. F04B 43/0054 310/367 |
| 2006/0096596 | A1* | 5/2006 | Occhialini ........ A61M 16/0057 128/204.18 |
| 2006/0157058 | A1* | 7/2006 | Aylsworth ............ A61M 16/10 128/204.23 |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2011/0023874 | A1 | 2/2011 | Bath et al. |
| 2011/0028853 | A1* | 2/2011 | Sano ................. A61B 5/02141 600/490 |

FOREIGN PATENT DOCUMENTS

| | | |
|---|---|---|
| WO | WO 98/34665 A1 | 8/1998 |
| WO | WO 00/78381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2009/152409 A1 | 12/2009 |
| WO | WO 2010/135785 A1 | 12/2010 |
| WO | WO 2011/128440 A1 | 10/2011 |
| WO | WO 2011/163530 A1 | 12/2011 |
| WO | WO 2012/067931 A2 | 5/2012 |
| WO | WO 2012/171072 A1 | 12/2012 |
| WO | WO 2013/020167 A1 | 2/2013 |
| WO | WO 2013/044195 A2 | 3/2013 |
| WO | WO 2013/067582 A1 | 5/2013 |
| WO | WO 2014/097119 A2 | 6/2014 |

\* cited by examiner

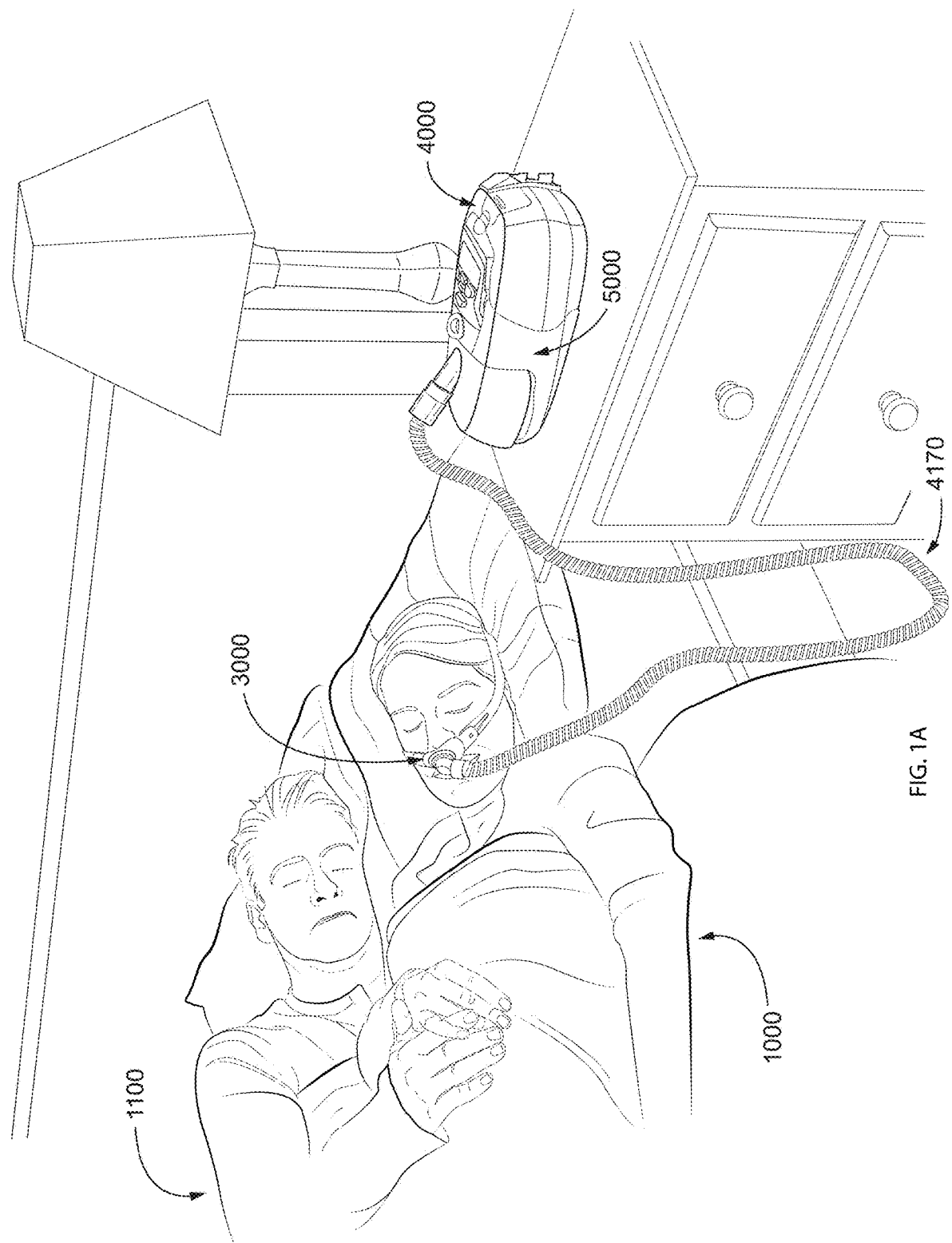

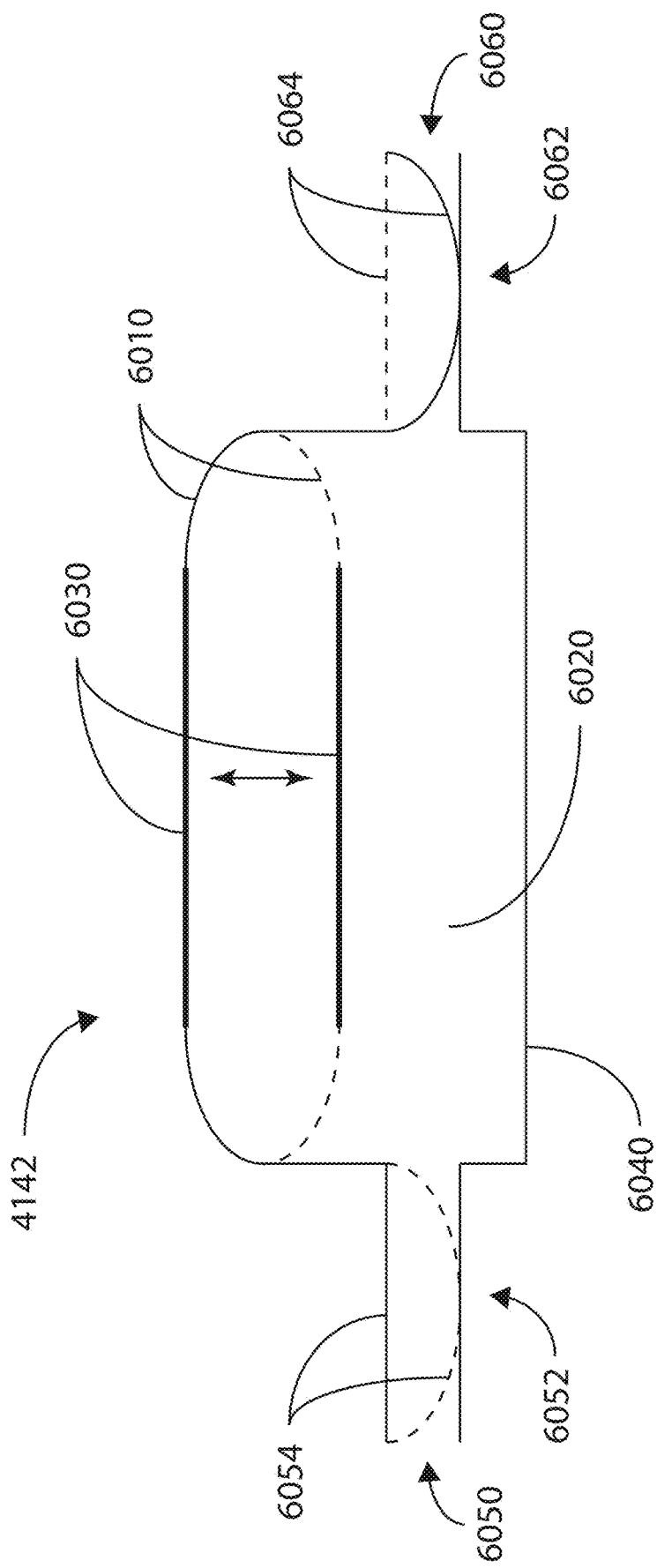

RESPIRATORY THERAPY APPARATUS

1 CROSS-REFERENCE TO RELATED APPLICATIONS

The present application claims the benefit of the filing dates of Australian Provisional Patent Application Nos. AU 2015900075, filed 13 Jan. 2015, AU 2015900138, filed 19 Jan. 2015, and AU 2015902607, filed 2 Jul. 2015, the entire contents of each of which are incorporated herewithin by reference.

2 BACKGROUND OF THE TECHNOLOGY

2.1 Field of the Technology

The present technology relates to one or more of the detection, diagnosis, treatment, prevention and amelioration of respiratory-related disorders. More specifically, the present technology relates to a component, such as a blower, or a valve for a blower, suitable for a medical device, such as a respiratory pressure therapy device.

2.2 Description of the Related Art

2.2.1 Respiratory Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR, OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.2 Treatment Systems

These therapies may be provided by a treatment system or device.

A treatment system may comprise a Respiratory Pressure Therapy Device (RPT device), an air circuit, a humidifier, a patient interface, and data management.

2.2.2.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

2.2.2.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound power level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

Examples of RPT devices include positive airway therapy (PAP) devices and ventilators.

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.2.3 Blower

As described above, a treatment system may comprise a blower to generate a flow of breathable gas (e.g. air, air with enriched oxygen or oxygen) for delivery to the patient. Some examples of prior art blowers used in an RPT device are described in U.S. Pat. Nos. 6,910,483 and 8,267,648, although other blower types such as axial or mixed flow blowers may be suitable.

Typical blowers that are used in RPT devices comprise a motor (e.g. a DC electric motor), a housing, one or more rotating parts (e.g. impellers), and one or more flow directing parts (e.g. stators). Such blowers may be axisymmetric, and may further comprise one or shafts about which the rotating parts revolve.

As a result, typical electric-motor driven rotating blowers may comprise a large number of components, leading to increased complexity, costs, and/or low reparability. Furthermore, a motor such as a DC electric motor may be expensive as it may comprise a rare earth magnet, and may be heavy.

Furthermore, not all blowers may be suitable for use as a blower for an RPT device due to unique requirements of RPT devices. For example, a blower for an RPT device is preferably quiet to not disturb the patient or a bed partner, such that the patient is more likely to comply with the therapy. The blower for an RPT device may be additionally capable of providing a flow of air to the patient in synchrony with the patient's breathing, such as by being able to accelerate and/or decelerate according to a patient's breathing patterns. Furthermore, a blower for an RPT device may comprise an elevated safety and reliability standard as it may be located adjacent to the patient, with the patient pneumatically coupled thereto, and the RPT device may be potentially a life-supporting device. Thus, blowers for an RPT device may comprise a unique field or unique requirements in at least some aspects.

3 BRIEF SUMMARY OF THE TECHNOLOGY

The present technology is directed towards a blower, such as one configured to produce a flow of gas at a positive pressure.

One aspect of the present technology relates to a blower for producing a flow of air at a positive pressure, the blower comprising a housing, one or more air inlets, one or more, e.g., a plurality of chambers in the housing e.g., arranged in parallel, each chamber configured to receive air from one or more of the one or more air inlets, at least one, e.g., a set of deformable members, each deformable member being convertible to a first configuration and a second configuration by electrical energy; and an air outlet to deliver air from the blower, wherein each said chamber is configured to produce the flow of air at a positive pressure through the blower outlet by conversion of the set of deformable members between the first configuration and the second configuration. If at least two chambers are provided, the, at least two chambers are configured to operate out of phase with each other.

In a further aspect of the present technology, the set of deformable members comprises an electroactive polymer.

In a further aspect of the present technology, the set of deformable members comprises a membrane.

In a further aspect of the present technology, a periphery of the membrane is secured to the housing.

In a further aspect of the present technology, the set of deformable members at least partly defines at least one of the plurality of chambers.

In a further aspect of the present technology, a deformable member of the set of deformable member at least partly defines at least two of the plurality of chambers.

In a further aspect of the present technology, the at least one of the set of deformable members is convertible between configurations by application of a predetermined magnitude of electrical energy.

In a further aspect of the present technology, the electrical energy is applied as a current through the one of the set of deformable members.

A further aspect of the present technology comprises a capacitive member configured to maintain at least one of the set of deformable members in a configuration by retaining electrical energy therein.

In a further aspect of the present technology, at least one of the set of deformable members is convertible to a third configuration between the first configuration and the second configuration.

In a further aspect of the present technology, all of the plurality of chambers are uniformly sized.

A further aspect of the present technology comprises a controller configured to control application of electrical energy to at least two of the set of deformable members independently of each other.

In a further aspect of the present technology, the controller is configured to vary application of electrical energy to the set of deformable members according to a measure of pressure.

In a further aspect of the present technology, the measure of pressure is indicative of a pressure at the air outlet.

A further aspect of the present technology comprises a pressure sensor to determine the measure of pressure.

In a further aspect of the present technology, the controller is configured to vary application of electrical energy to the set of deformable members to reduce a difference between the measure of pressure and a target pressure.

In a further aspect of the present technology, the target pressure is a predetermined pressure.

In a further aspect of the present technology, the controller is configured to vary a frequency of application of electrical energy to reduce the difference between the measure of pressure and the target pressure.

A further aspect of the present technology comprises a chamber arranged in series to one of the plurality of chambers.

A further aspect of the present technology comprises a valve comprising a deformable member.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.

4.2 Respiratory System and Facial Anatomy

FIG. 2A shows an overview of a human respiratory system including the nasal and oral cavities, the larynx, vocal folds, oesophagus, trachea, bronchus, lung, alveolar sacs, heart and diaphragm.

4.3 Patient Interface

FIG. 3A shows a patient interface in the form of a nasal mask in accordance with one form of the present technology.

4.4 RPT Device

4.5 Humidifier

Figure 5A:
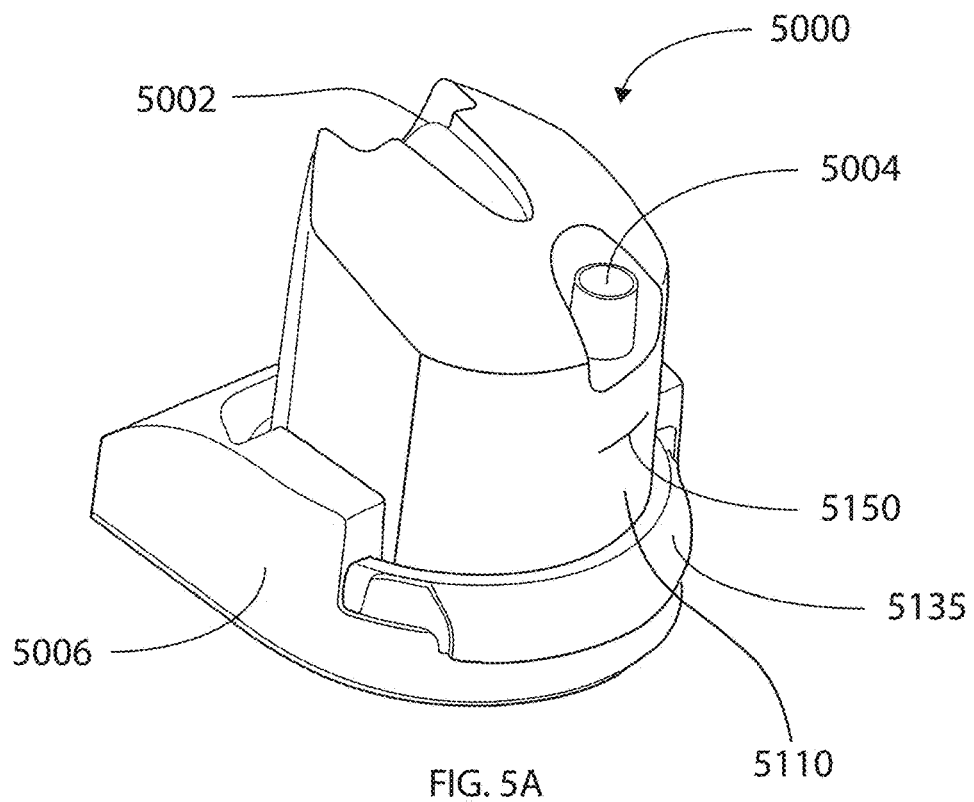

FIG. 5A shows an isometric view of a humidifier in accordance with one form of the present technology.

Figure 5B:
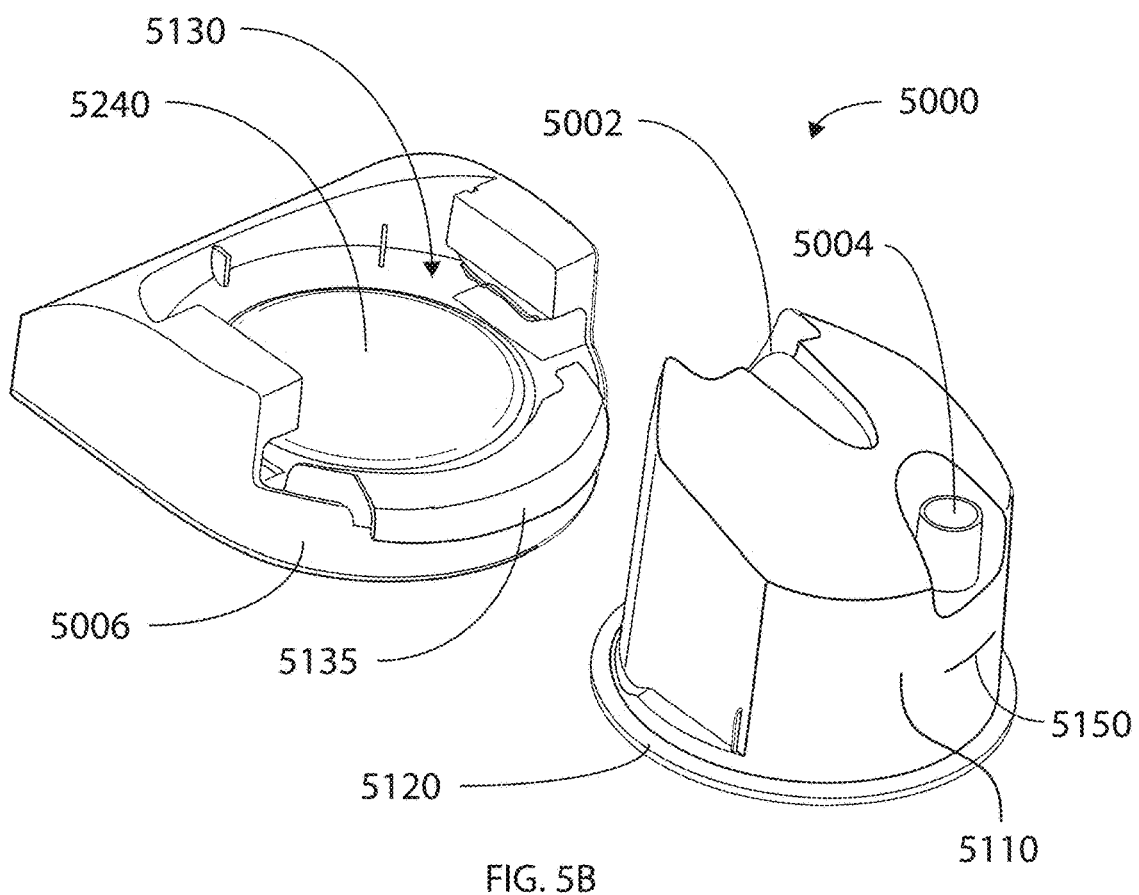

FIG. 5B shows an isometric view of a humidifier in accordance with one form of the present technology, showing a humidifier reservoir 5110 removed from the humidifier reservoir dock 5130.

4.6 Blower

Figure 6A:
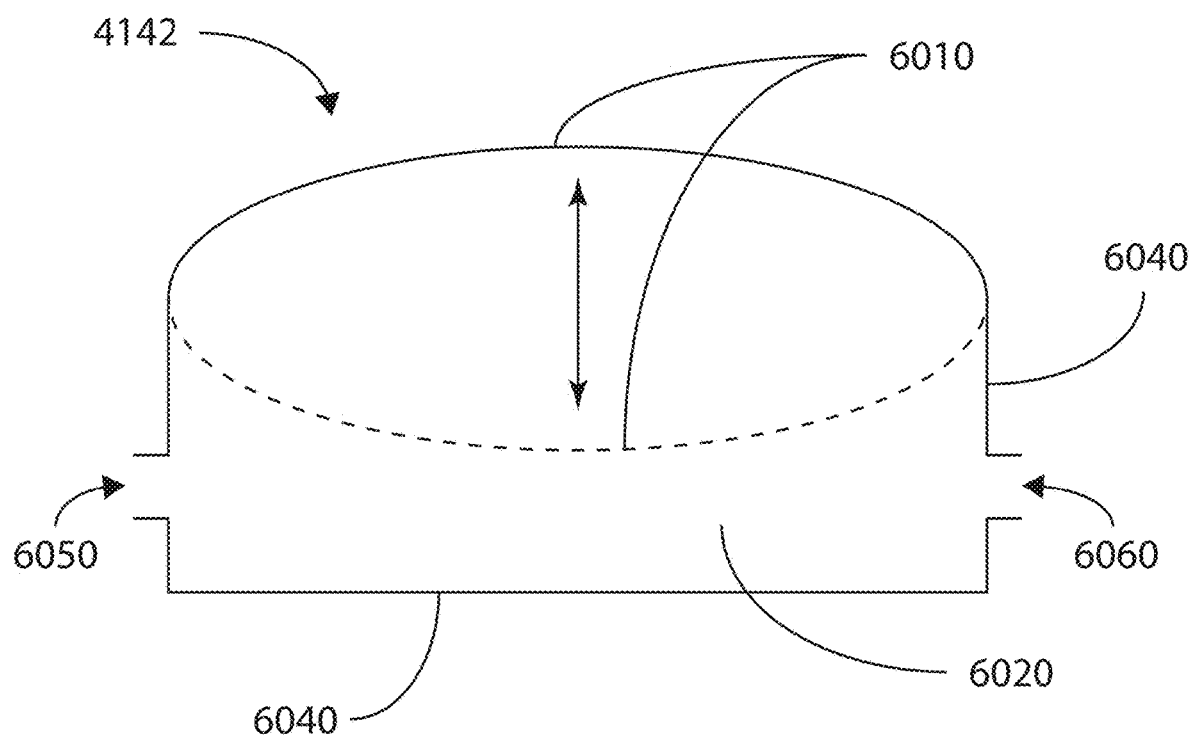

FIG. 6A shows a simplified representation of a blower 4142 according to one form of the present technology, wherein the blower 4142 comprises a deformable member 6010 convertible between a first configuration and a second configuration for generating an air flow.

Figure 6B:
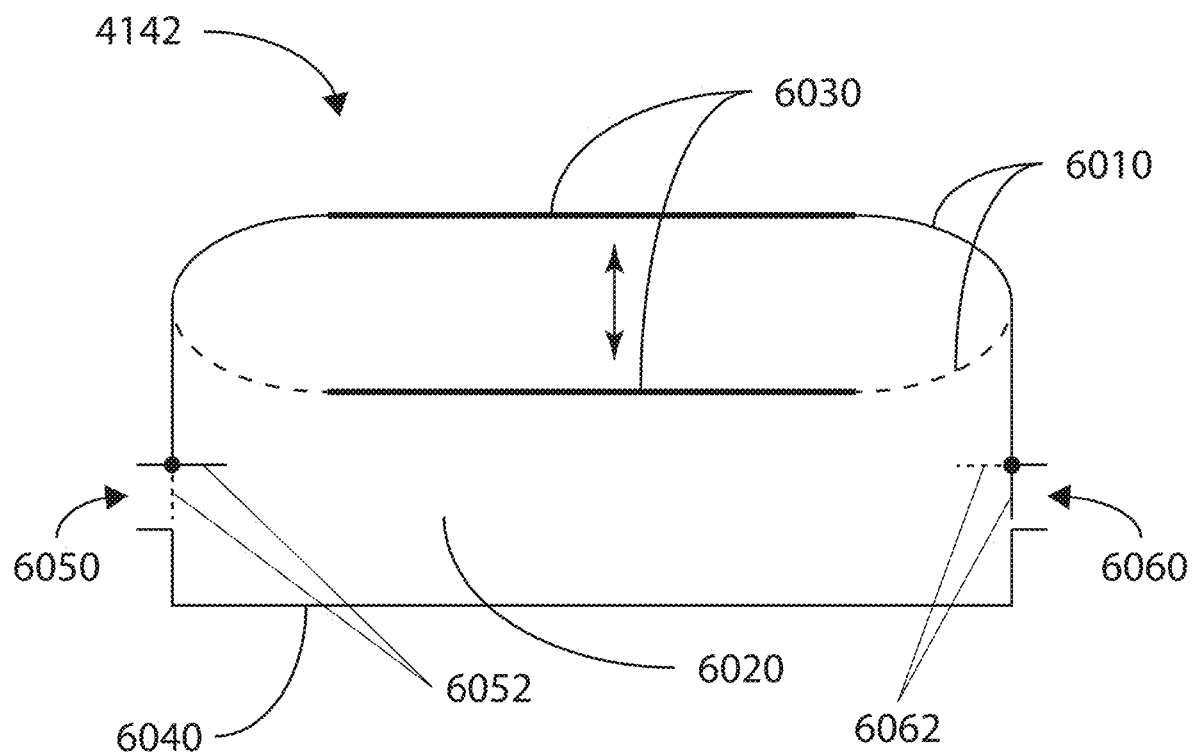

FIG. 6B shows a simplified representation of a blower 4142 according to another form of the present technology, wherein the blower 4142 comprises a deformable member 6010 connected to a movable wall 6030 and convertible between a first configuration and a second configuration to generate an air flow.

Figure 6C:
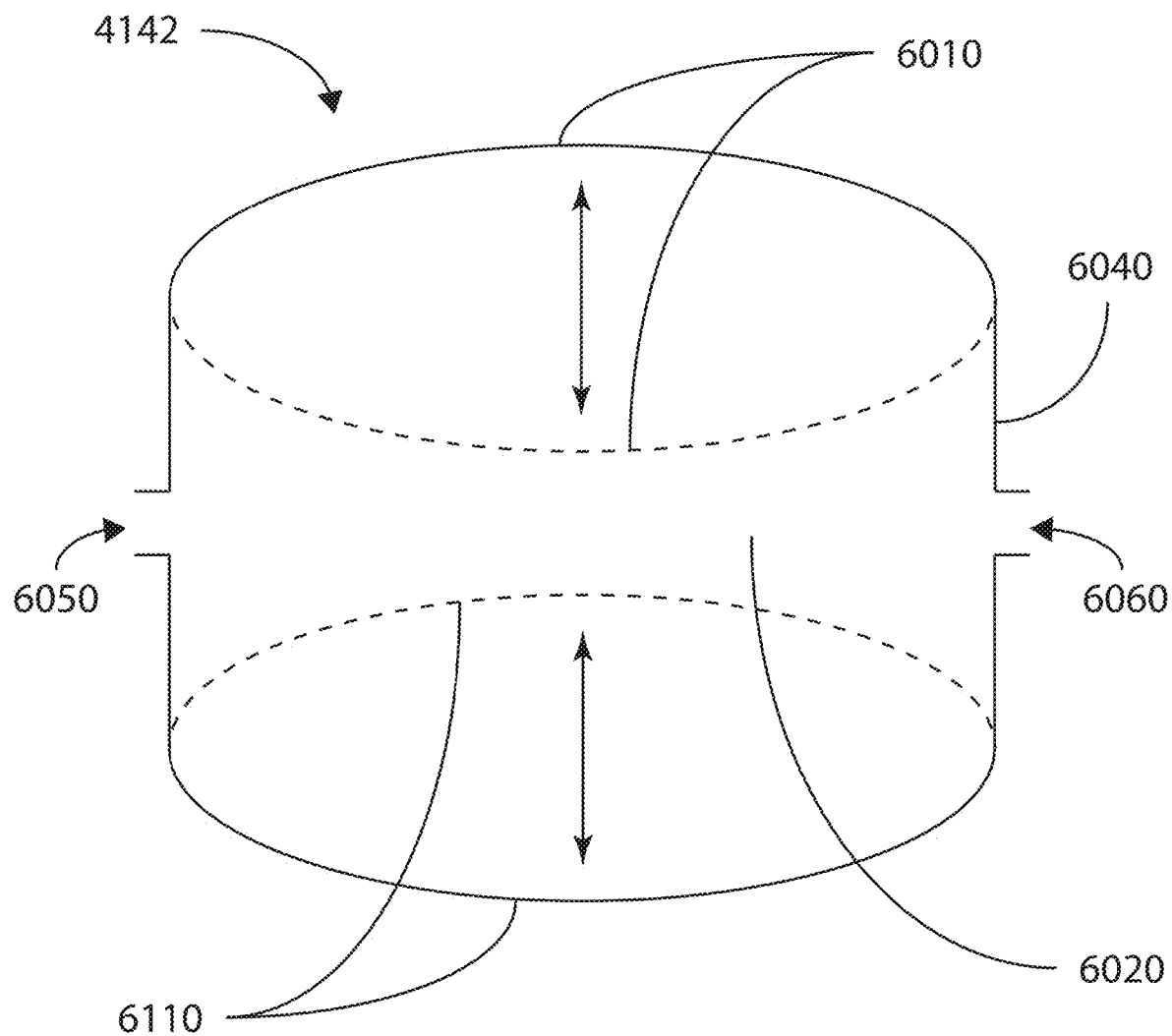

FIG. 6C shows a simplified representation of a blower 4142 according to one form of the present technology, comprising two deformable members 6010 and 6110.

Figure 6D:
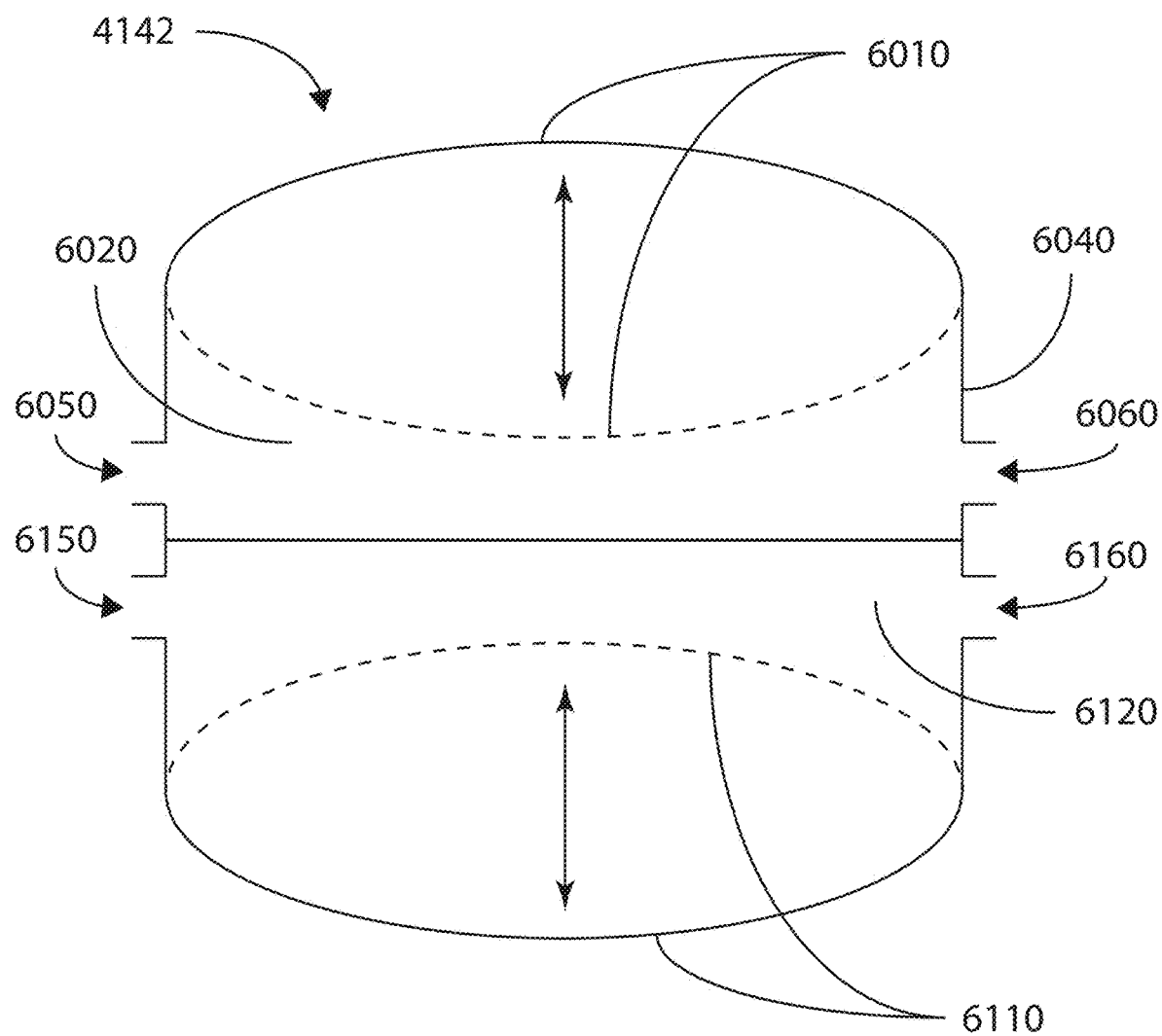

FIG. 6D shows a simplified representation of a blower 4142 according to one form of the present technology, comprising two chambers 6020 and 6120, each chamber comprising a deformable member 6010 and 6110 respectively.

Figure 6E:
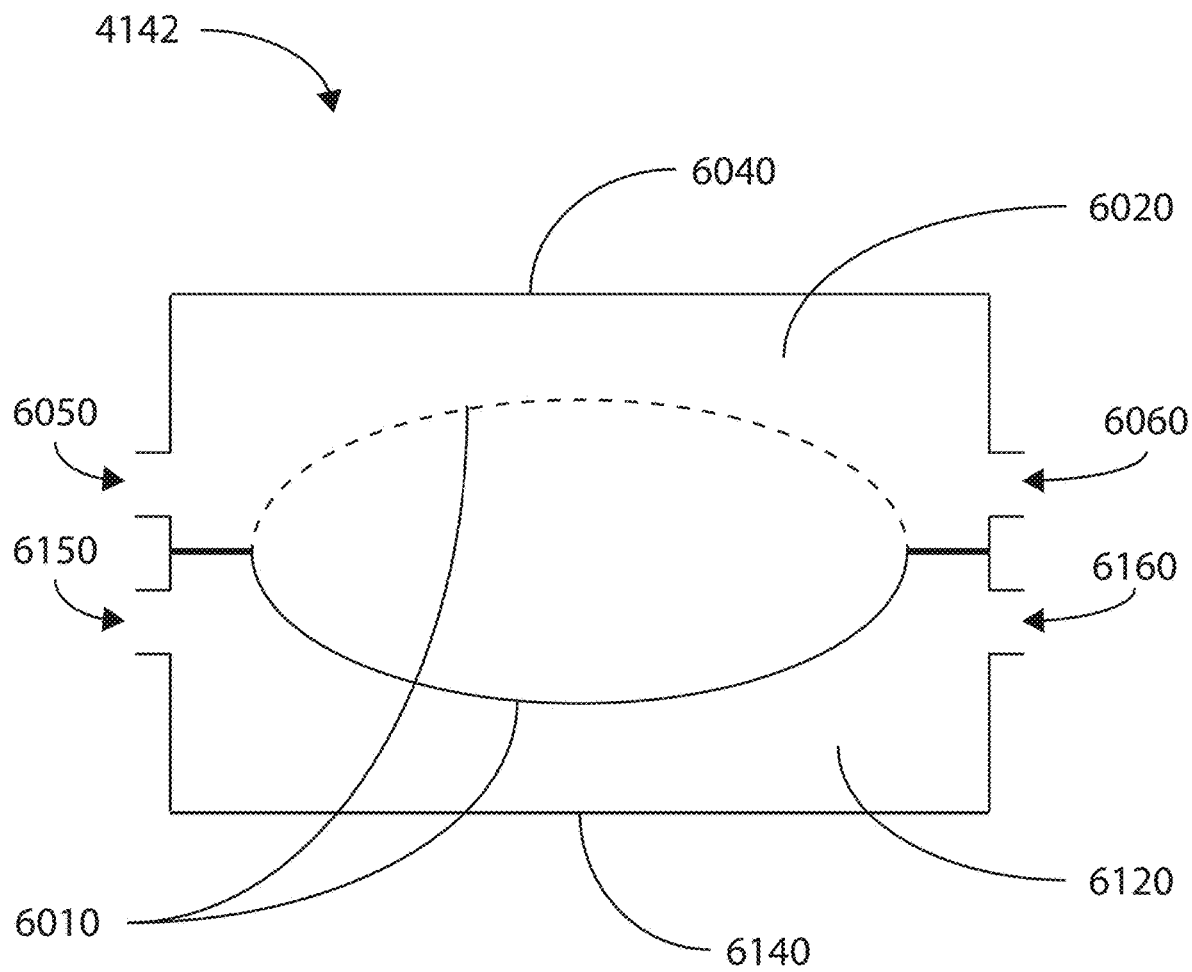

FIG. 6E shows a simplified representation of a blower 4142 according to one form of the present technology, comprising two chambers 6020 and 6120 and a deformable member 6010 configured to increase and decrease a volume of both of the chambers 6020 and 6120.

Figure 6F:
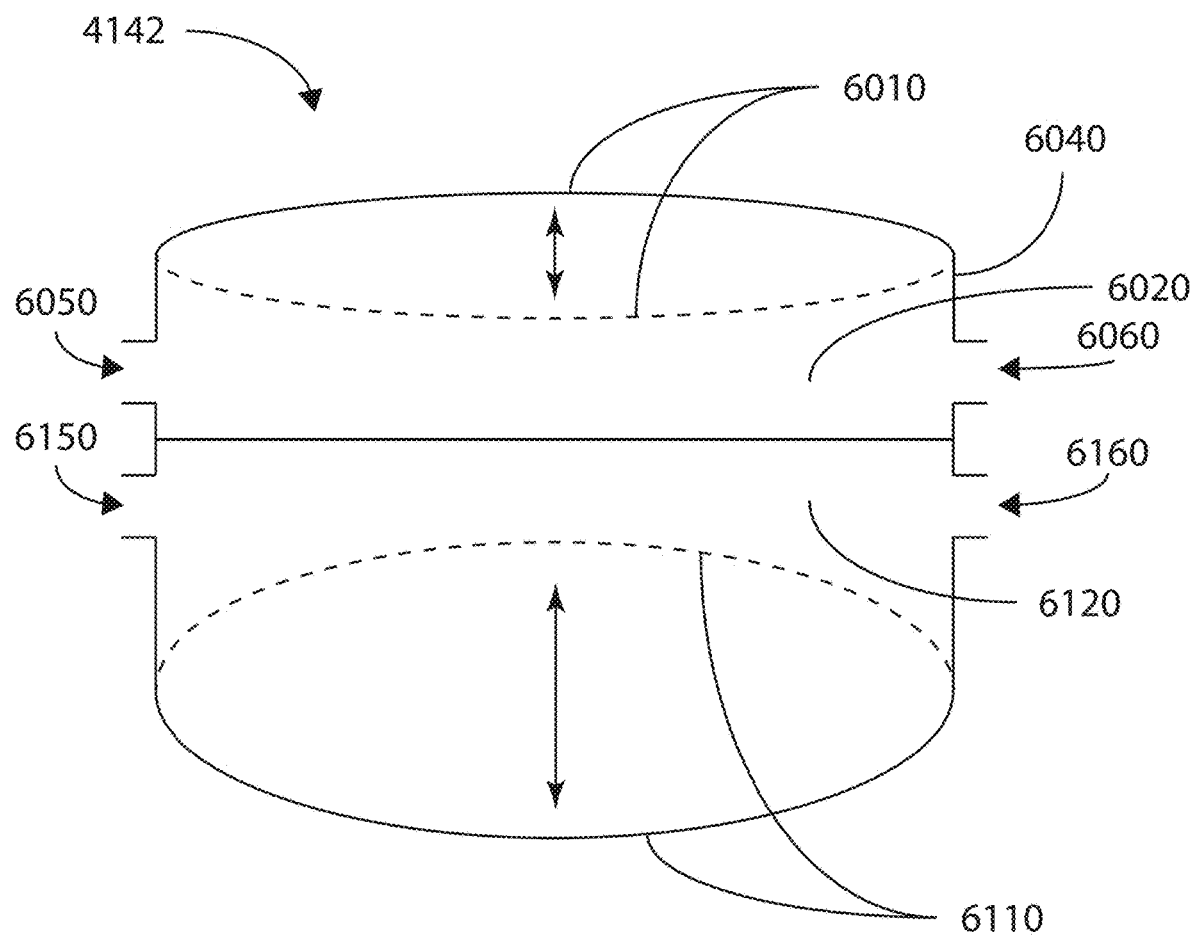

FIG. 6F shows a simplified representation of a blower 4142 according to one form of the present technology, comprising two chambers 6020 and 6120 of varying sizes and a deformable member 6010 configured to increase and decrease a volume of both of the chambers 6020.

Figure 6G:
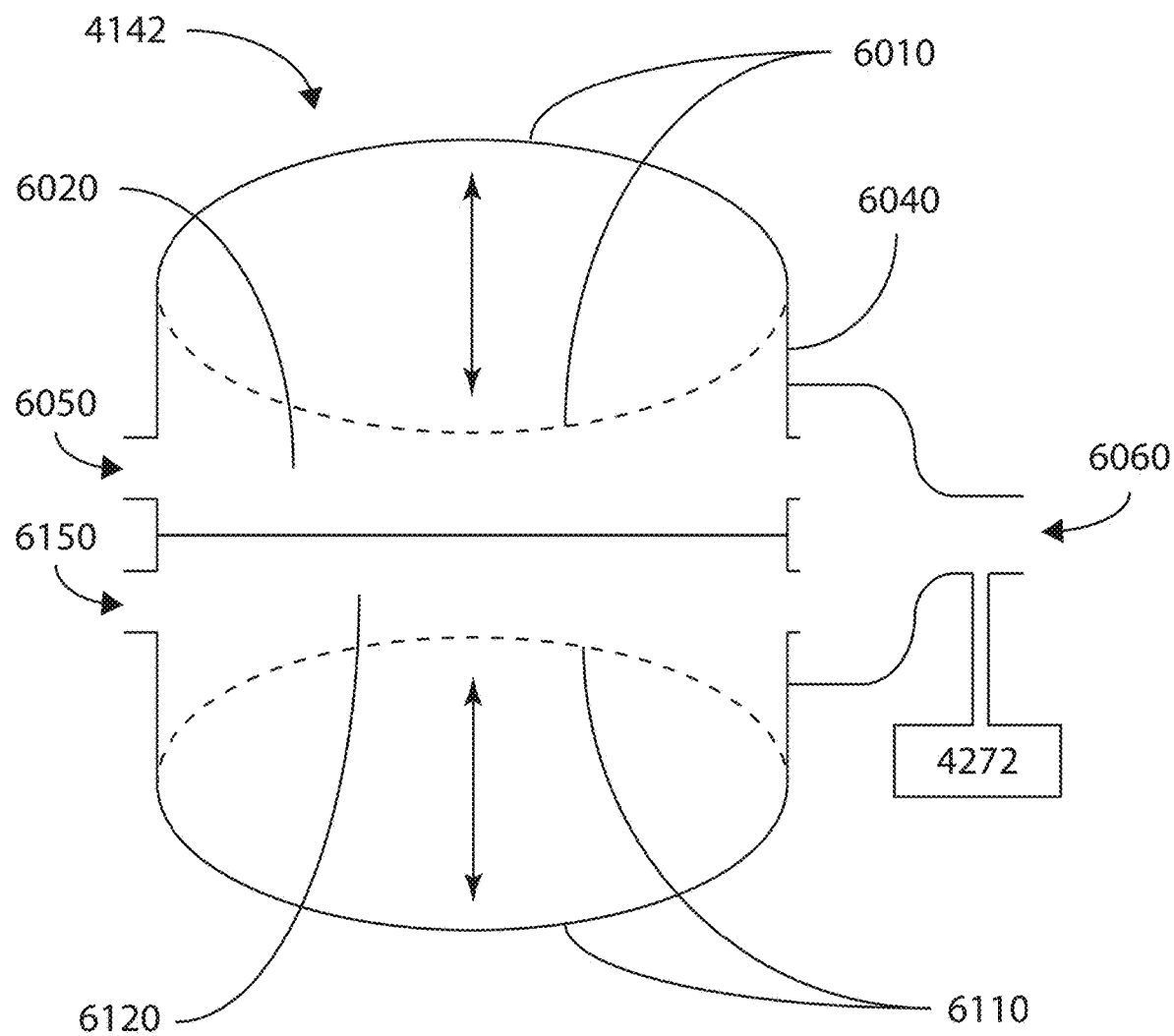
Figure 61:
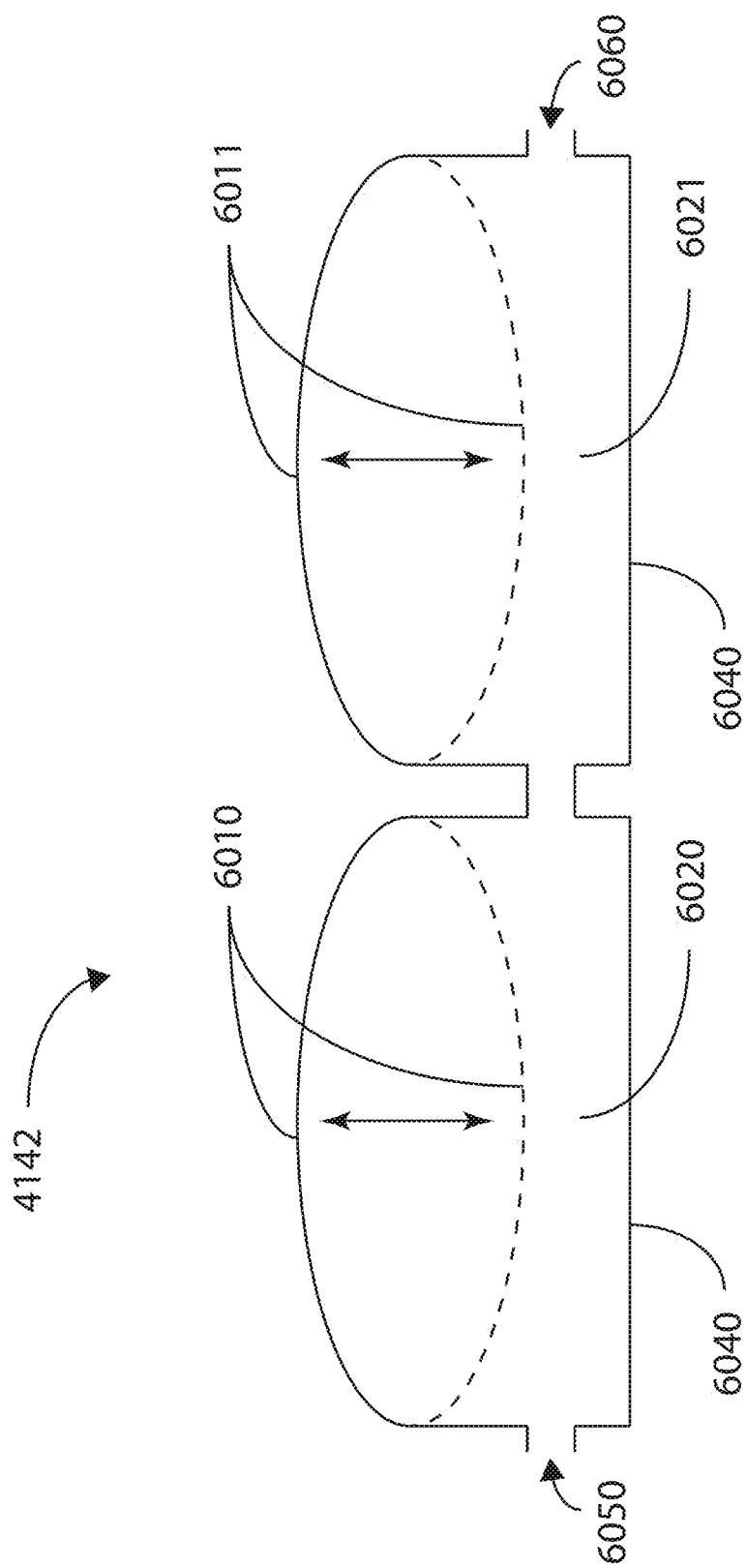

FIG. 6G shows a simplified representation of a blower 4142 according to one form of the present technology, comprising two chambers 6020 and 6120 and a single blower outlet 6060.

FIG. 6H shows an exemplary schematic of a blower 4142 according to the present technology, comprising an inlet valve 6052 and an outlet valve 6062, wherein each valve comprises a deformable member 6054 and 6064 respectively.

FIG. 6I shows an exemplary schematic of a blower 4142 according to the present technology, comprising two chambers 6020 and 6021 connected in series.

Figure 6J:
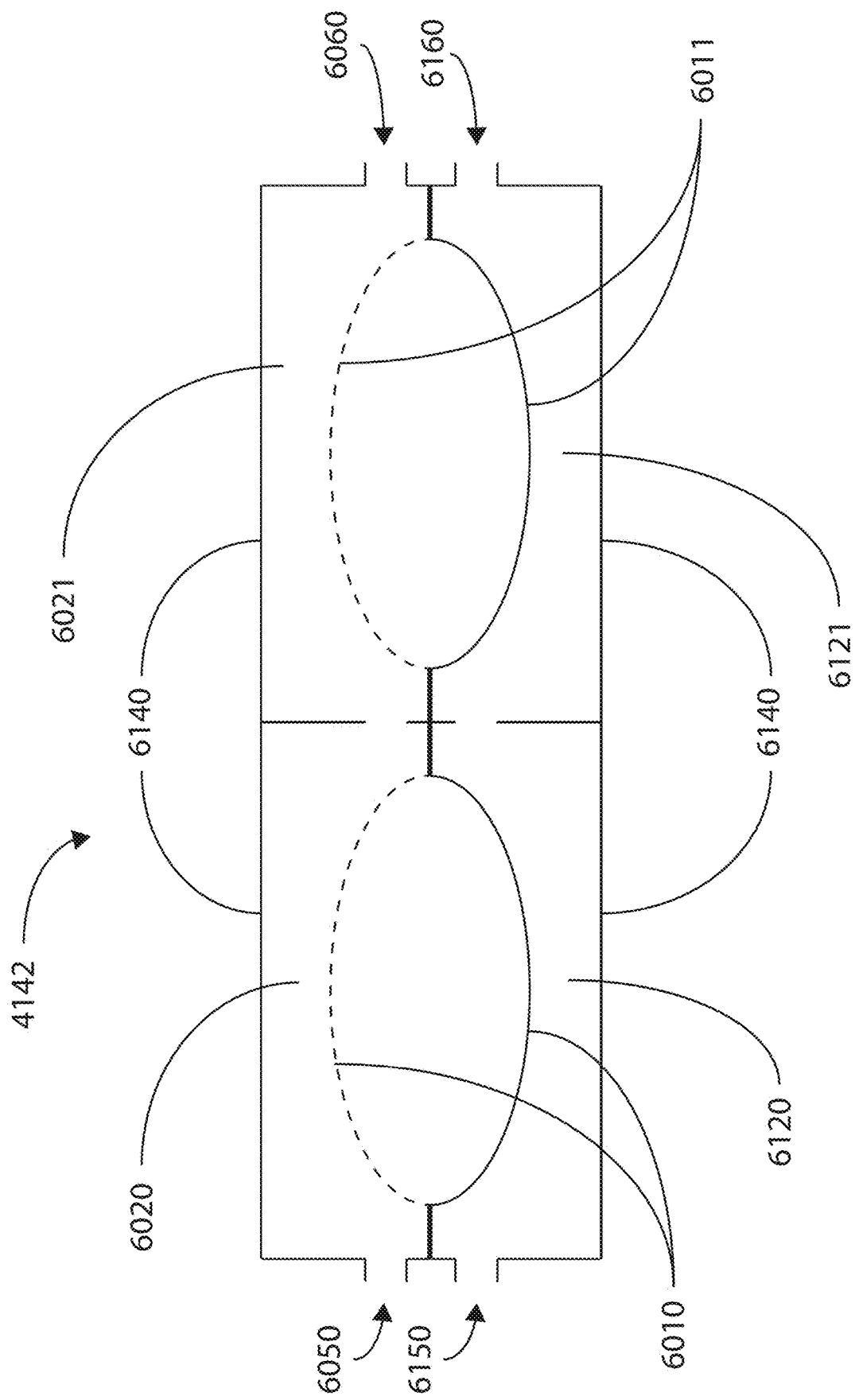

FIG. 6J shows an exemplary schematic of a blower 4142 according to the present technology, comprising four chambers 6020, 6021, 6120 and 6121.

Figure 6K:
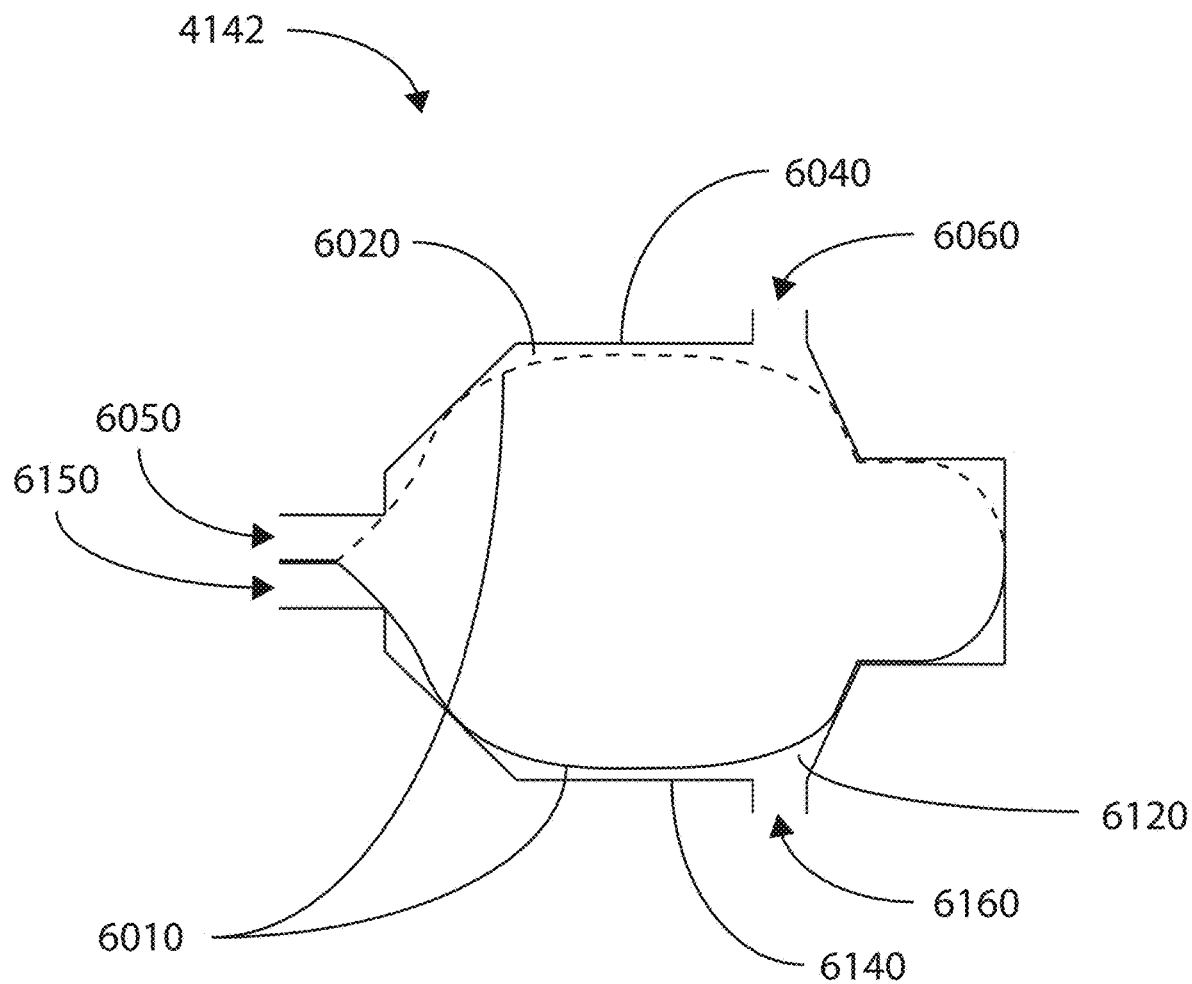

FIG. 6K shows an exemplary schematic of a blower 4142 according to one form of the present technology, comprising two chambers 6020 and 6120 and a deformable member 6010 configured to increase and decrease a volume of both of the chambers 6020 and 6120, wherein the deformable member is configured to conform to a chamber walls 6040 and 6140 in a first and second configurations respectively.

Figure 6L:
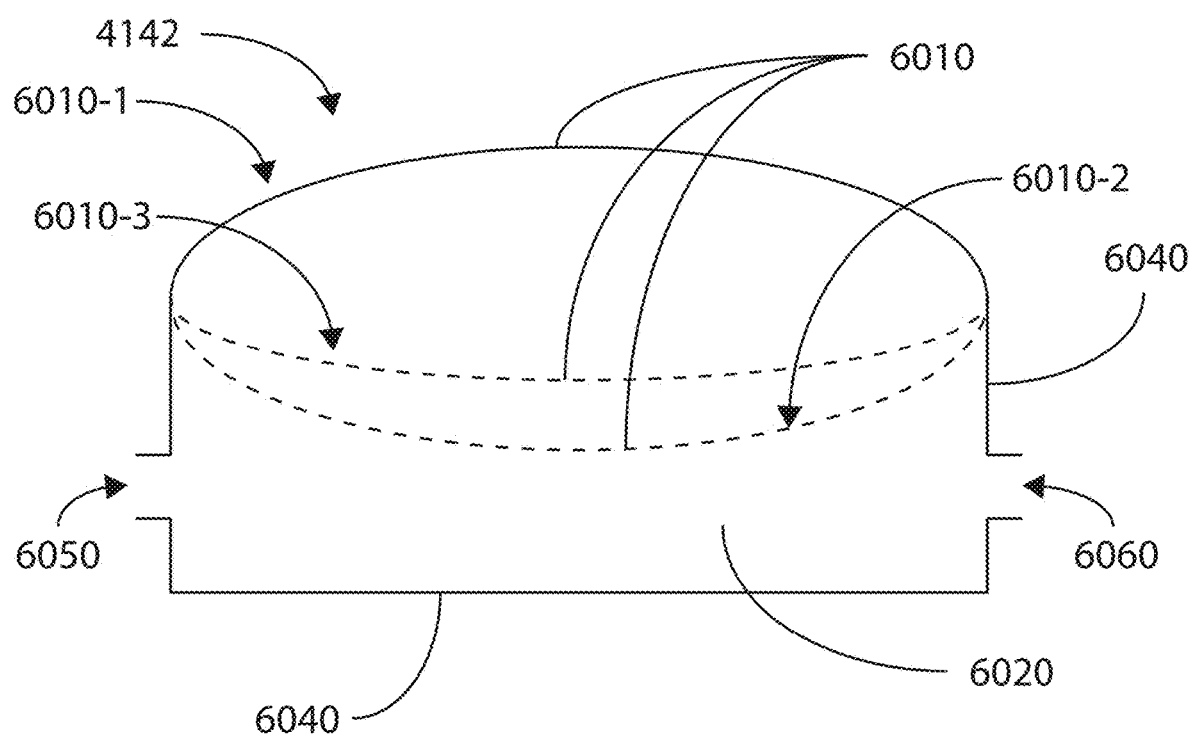

FIG. 6L shows an exemplary schematic of a blower 4142 according to the present technology, comprising a deformable member 6010, showing variable positions for the deformable member 6010 at the end of the exhaust portion of a pumping cycle.

Figure 6M:
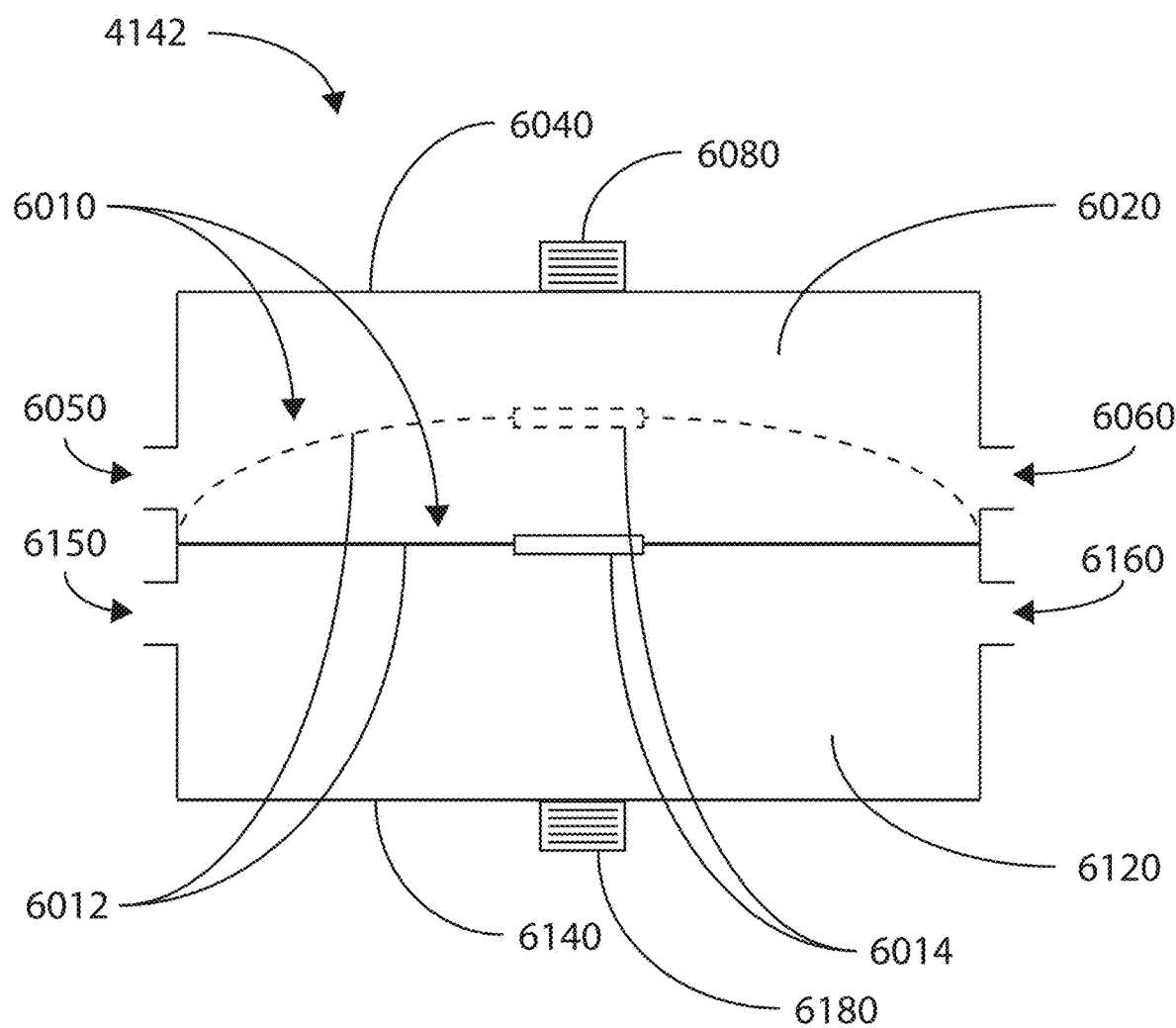

FIG. 6M shows an exemplary schematic of a blower 4142 according to the present technology, comprising a deformable member 6010 including an elastic portion 6012 and a controllable portion 6014, and wherein the blower 4142 includes actuators 6080 and 6180 for actuating the deformable member 6010.

Figure 6N:
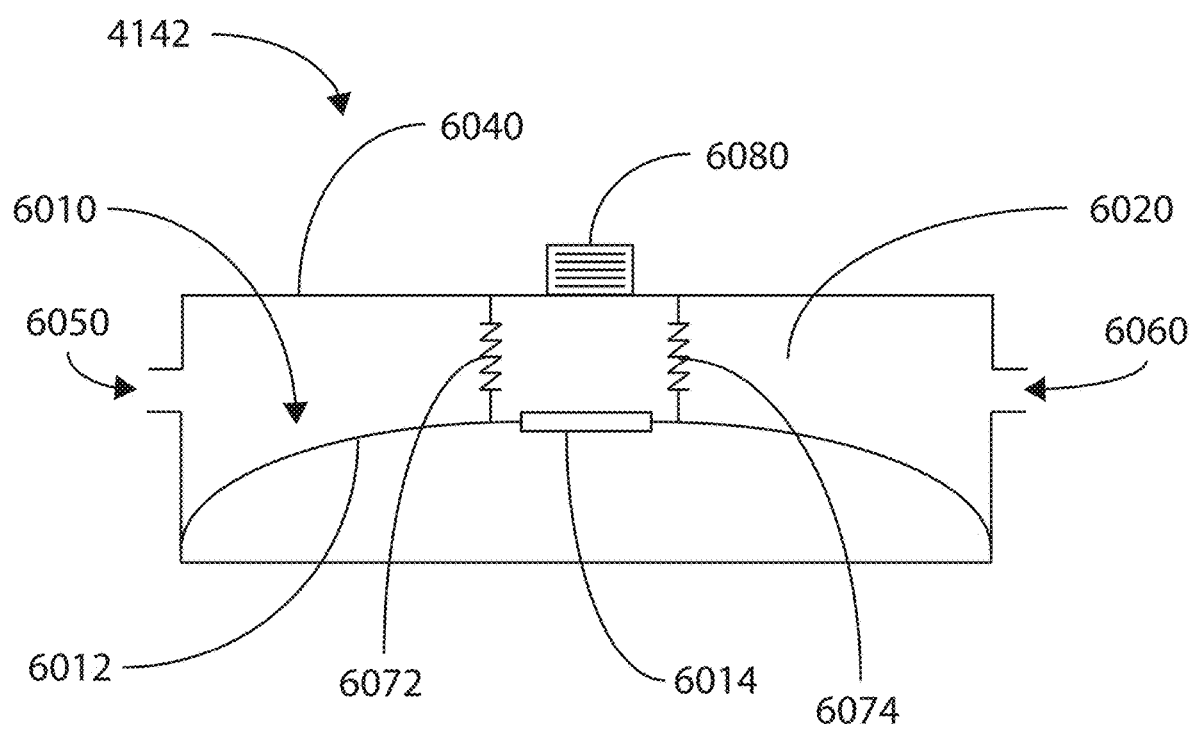

FIG. 6N shows an exemplary schematic of a blower 4142 according to the present technology, comprising a deformable member 6010 including an elastic portion 6012 and a controllable portion 6014, the blower further comprising a biasing portion to bias a position of the deformable member.

Figure 7A:
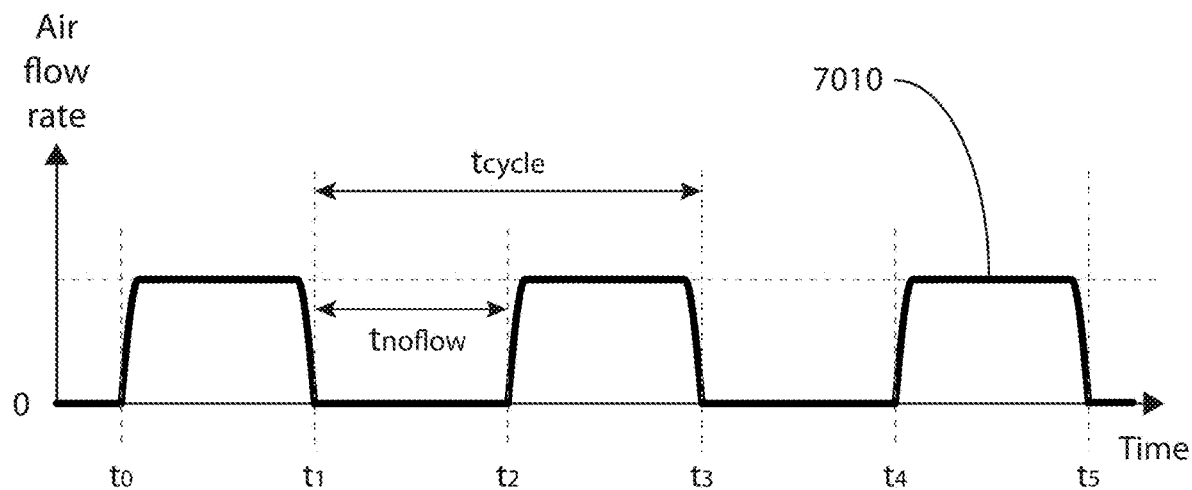

FIG. 7A shows an exemplary graph of air flow rate for an air flow generated by a blower 4142.

Figure 7B:
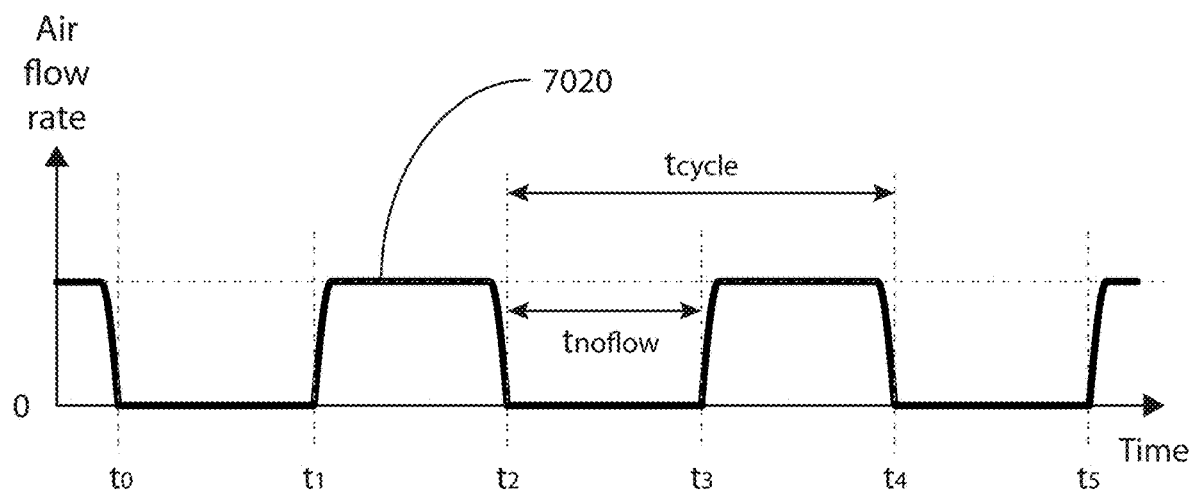

FIG. 7B shows an exemplary graph of air flow rate for an air flow generated by a blower 4142, wherein the flow shown is out of phase with that shown in FIG. 7A.

Figure 7C:
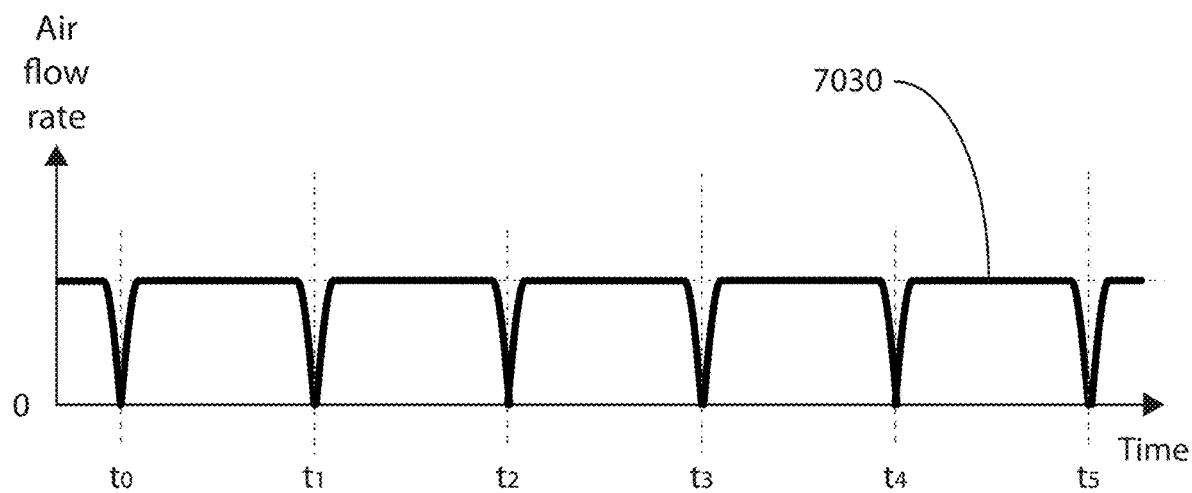

FIG. 7C shows an exemplary graph of air flow rate delivered through a blower outlet, wherein the flow shown is a sum of the flows shown in FIGS. 7A and 7B.

Figure 7D:
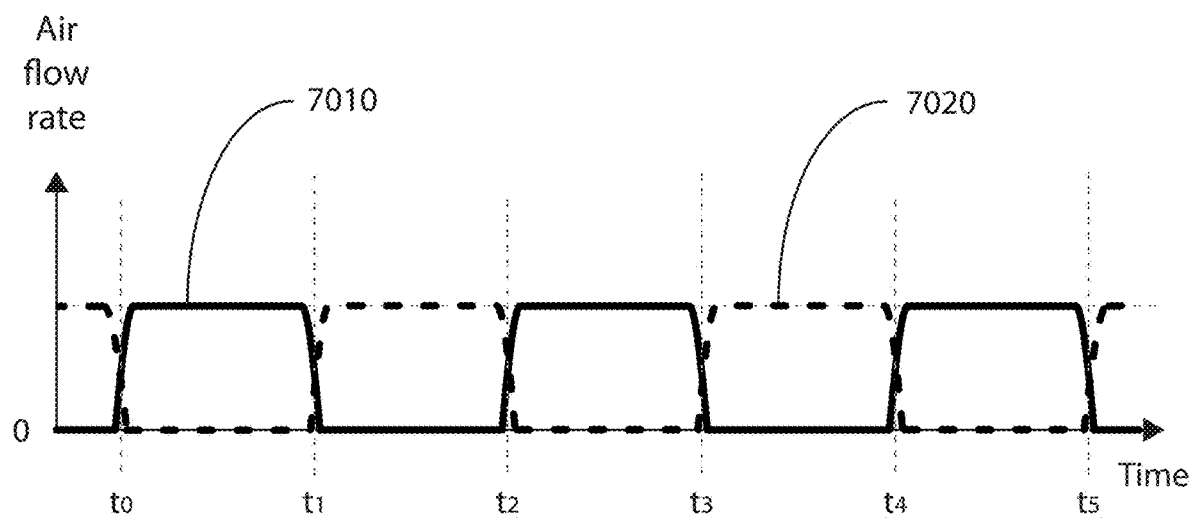

FIG. 7D shows an exemplary graph of air flow rate delivered through a blower outlet, showing two air flows that partly overlap during the rise and fall periods respectively.

Figure 7E:
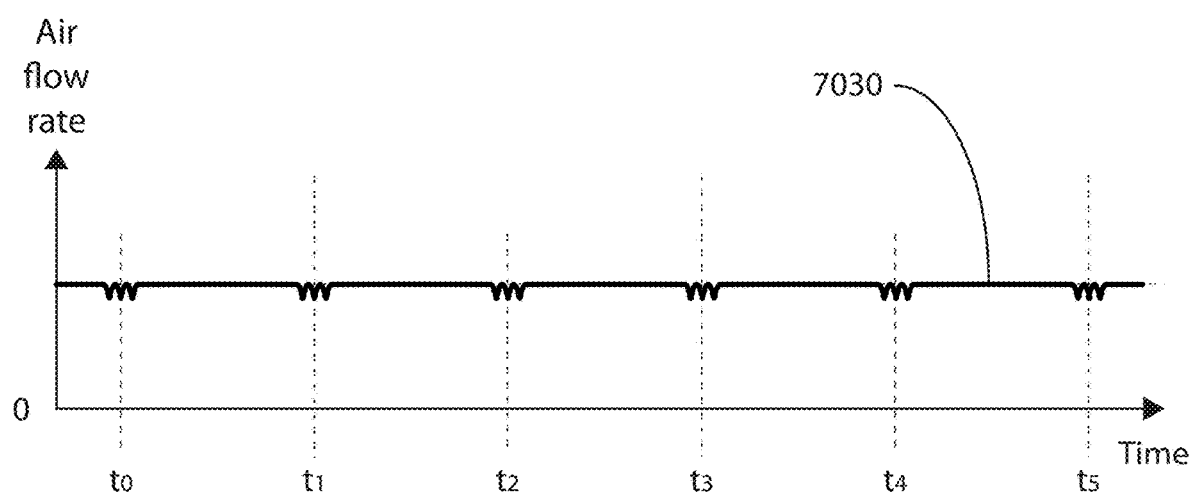

FIG. 7E shows an exemplary graph of air flow rate delivered through a blower outlet, wherein the flow rate is a sum of the flows shown in FIG. 7D.

FIGS. 8A-8D show a simplified representation of a blower 4142 according to one form of the present technology, comprising four chambers 8020, 8120, 8220 and 8320, and two deformable members 8010 and 8210, wherein the two deformable members 8010 and 8210 are operating out of phase by approximately 90 degrees.

Figure 9A:
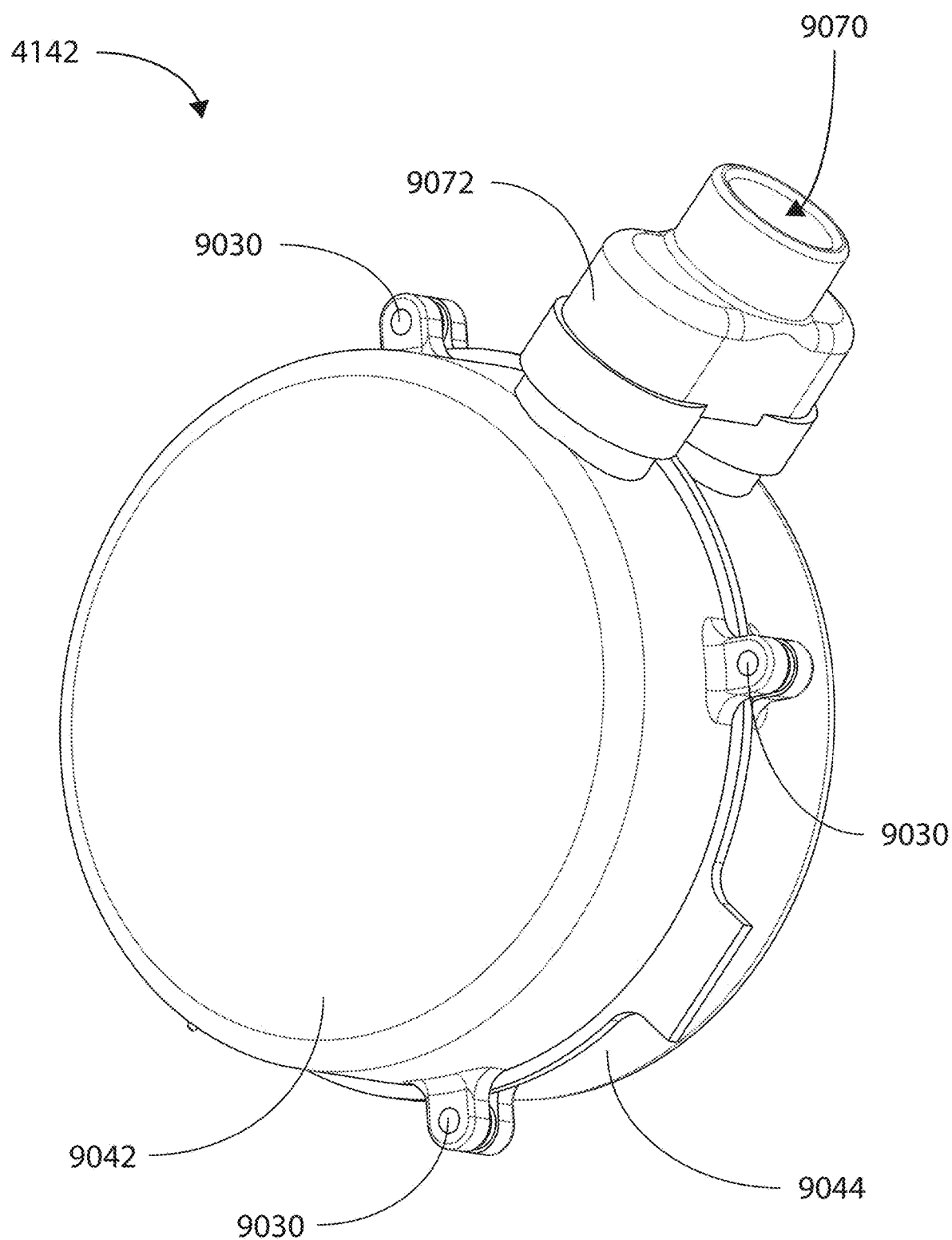
Figure 9B:
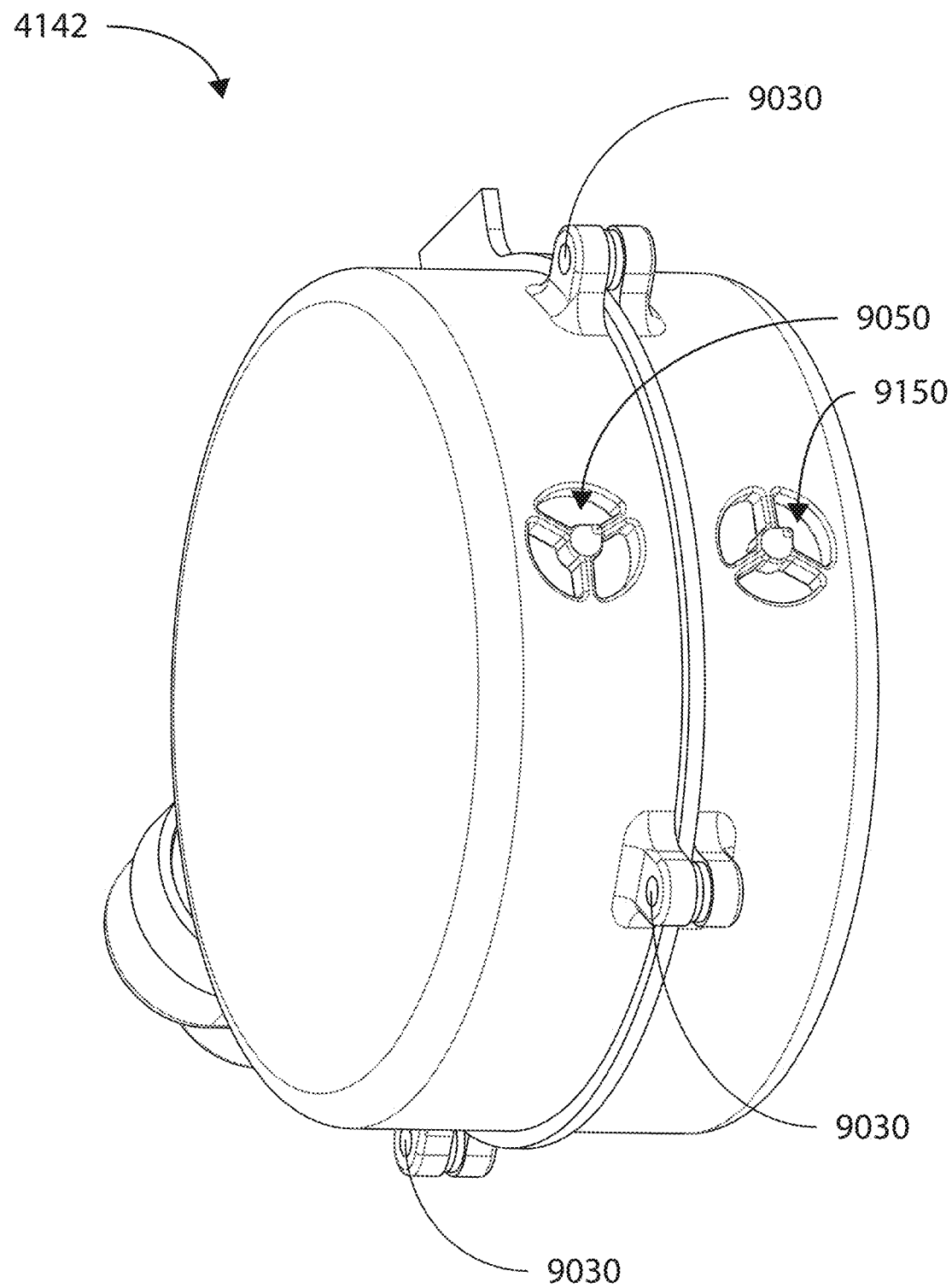

FIGS. 9A-9B show perspective views of a blower 4142 according to one form of the present technology, comprising a first housing 9042 and a second housing 9044, inlets 9050 and 9150 and a blower outlet 9070.

Figure 9C:
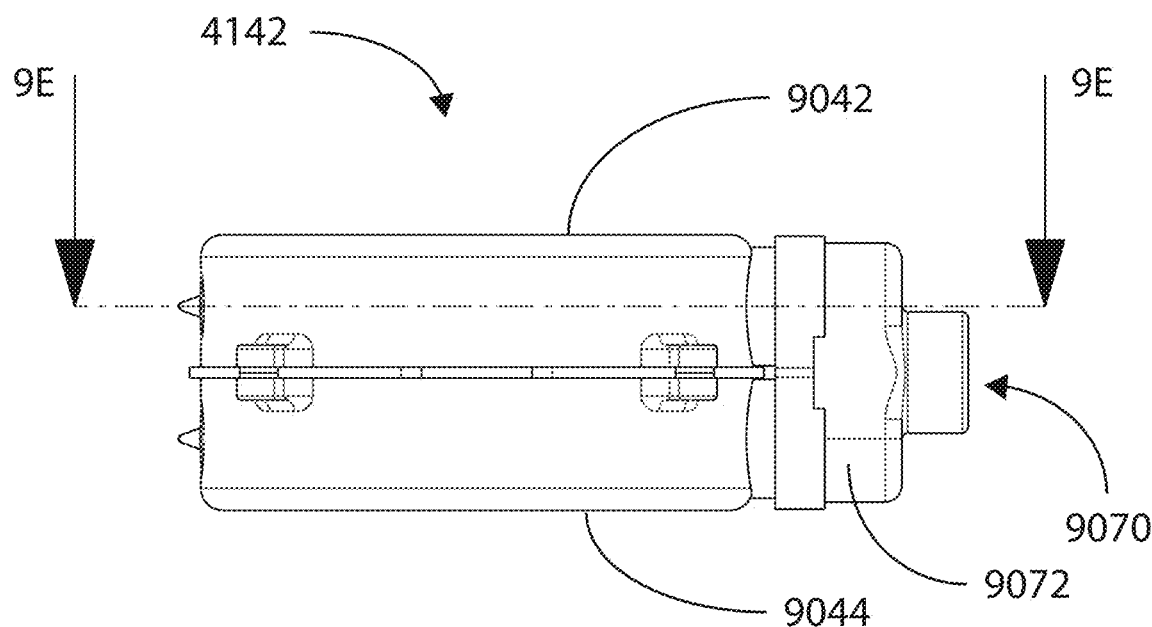
Figure 9D:
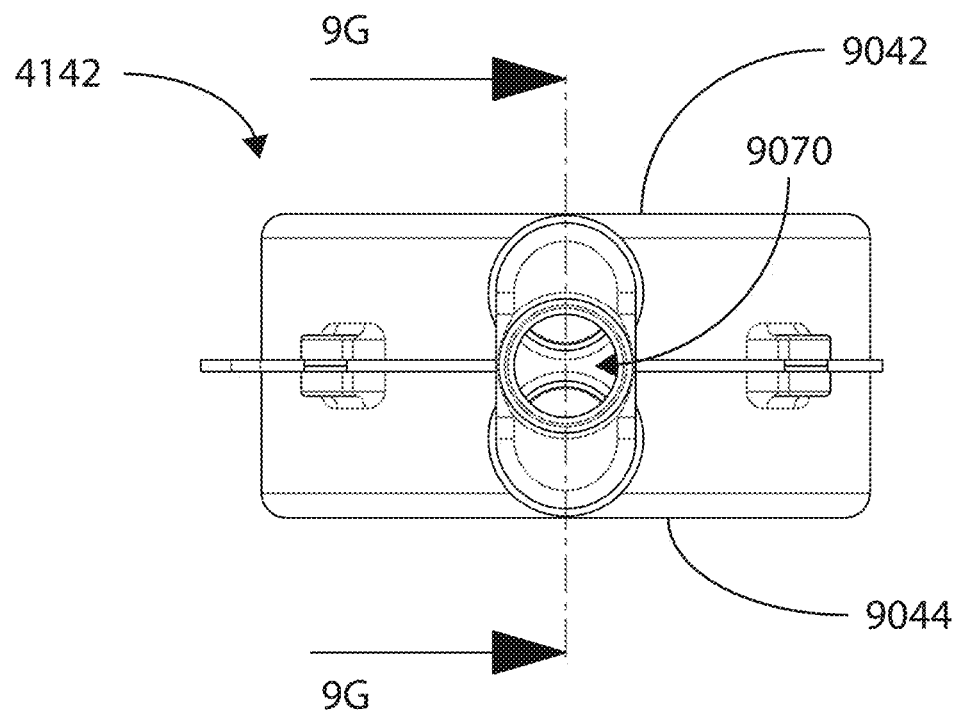

FIGS. 9C-9D shows side views of the blower 4142 as shown in FIGS. 9A-9B, indicating cross sections 9E-9E and 9G-9G respectively.

Figure 9E:
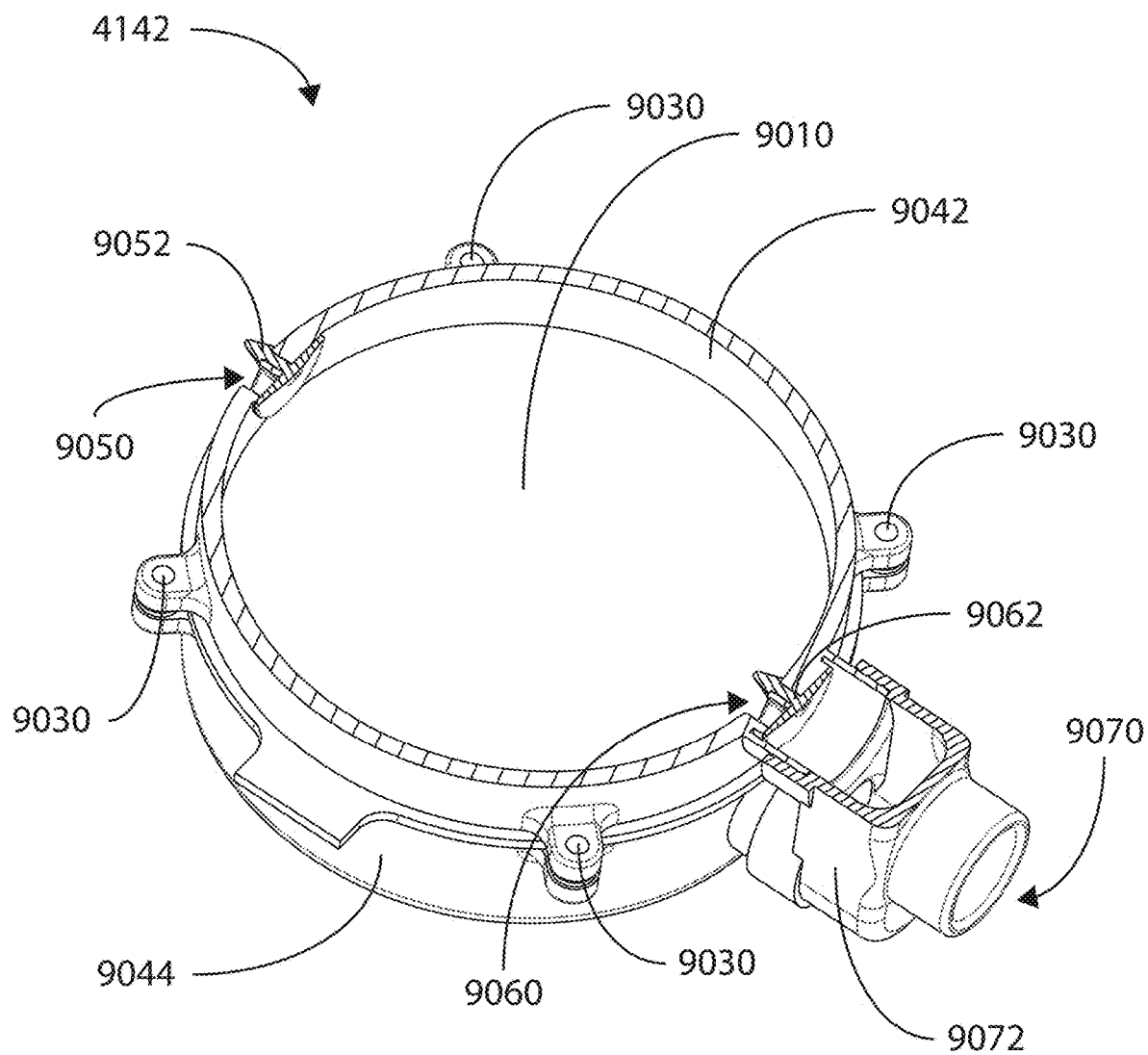

FIG. 9E shows a perspective cross-section view of the blower 4142 shown in FIG. 9C, showing a cross-section 9E-9E taken through the chamber 9020, chamber inlet 9050 and the chamber outlet 9060.

Figure 9F:
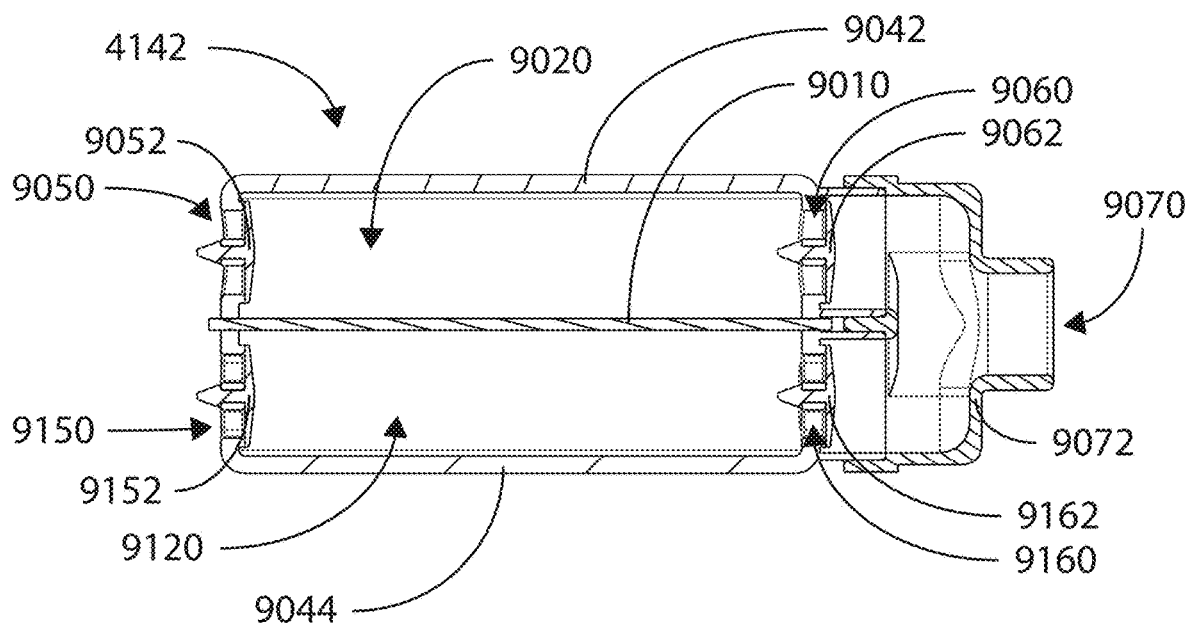

FIG. 9F shows a side cross-section view of the blower 4142 shown in FIG. 9D, showing a cross-section 9G-9G, through which the chambers 9020 and 9120, the deformable member 9010 and the blower outlet 9070 may be seen.

Figure 9G:
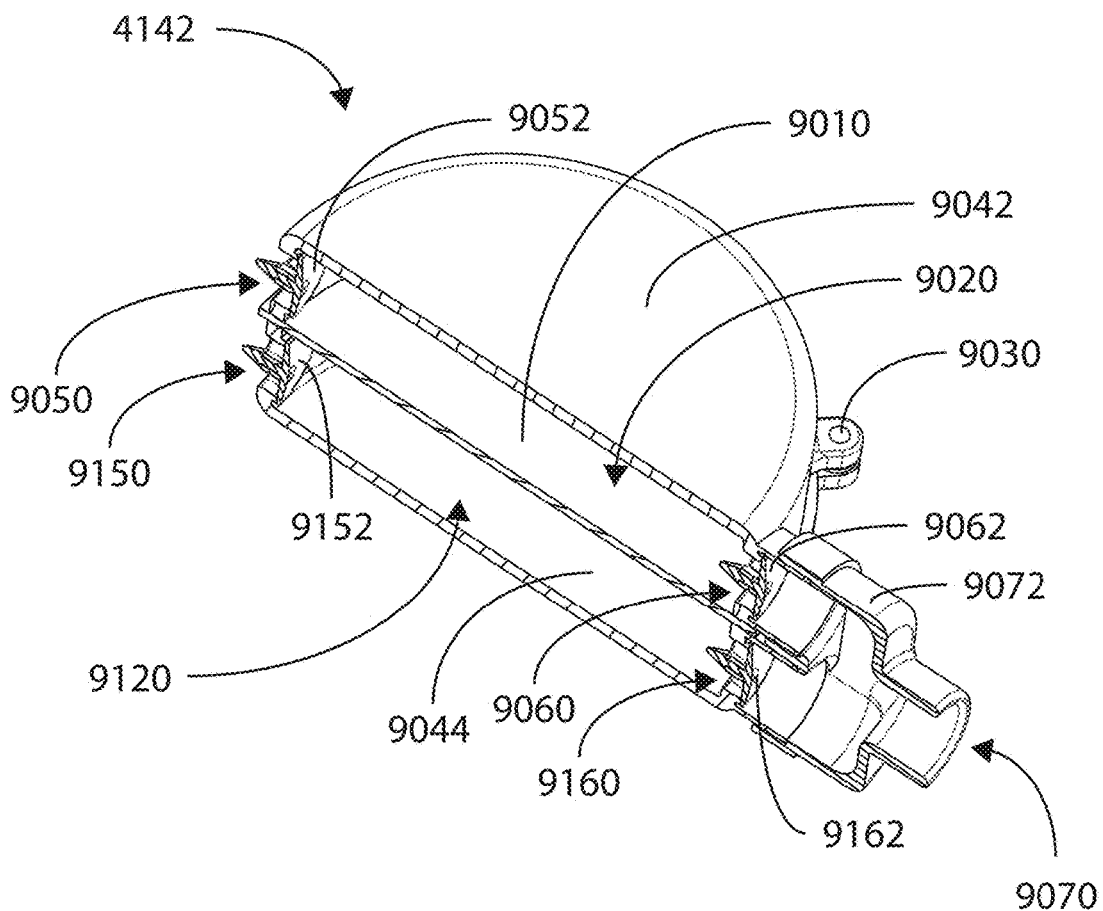

FIG. 9G shows a perspective cross-section view of the blower 4142 as shown in FIG. 9F, showing a cross-section 9G-9G.

Figure 10A:
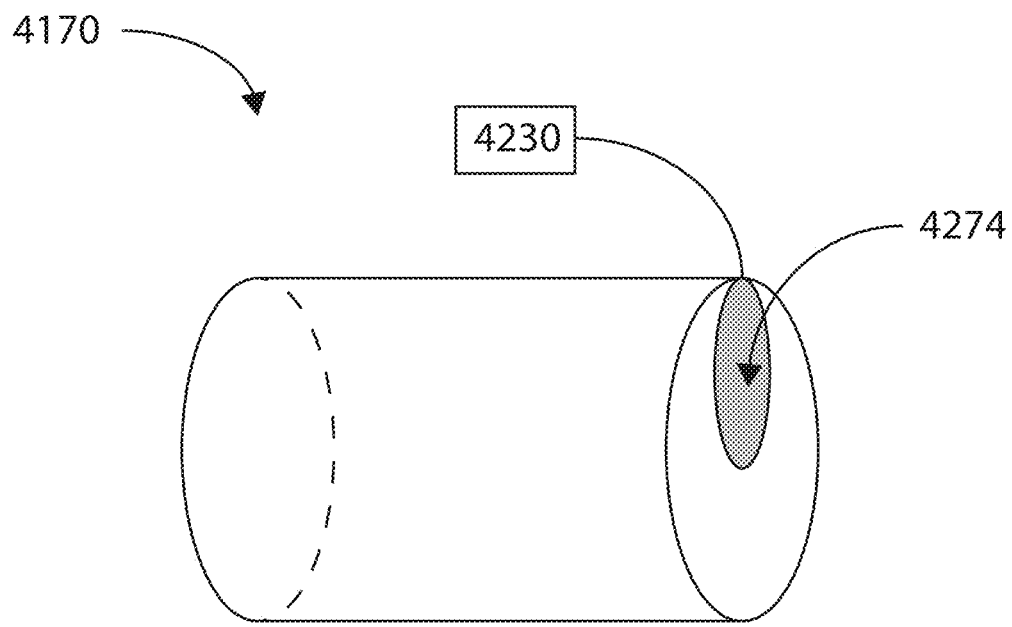

FIG. 10A shows a perspective view of an air circuit 4170 comprising a part of an air flow rate sensor 4274.

Figure 10B:
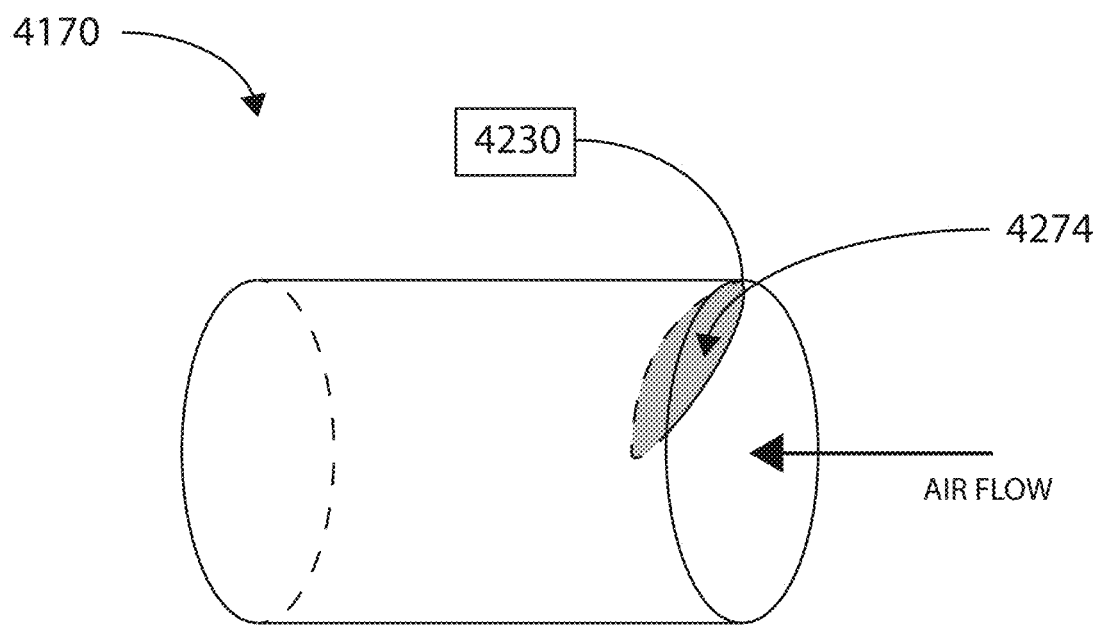

FIG. 10B shows another perspective view of an air circuit 4170 comprising a part of an air flow rate sensor 4274, wherein the air flow has increased from that shown in FIG. 10A.

Figure 11A:
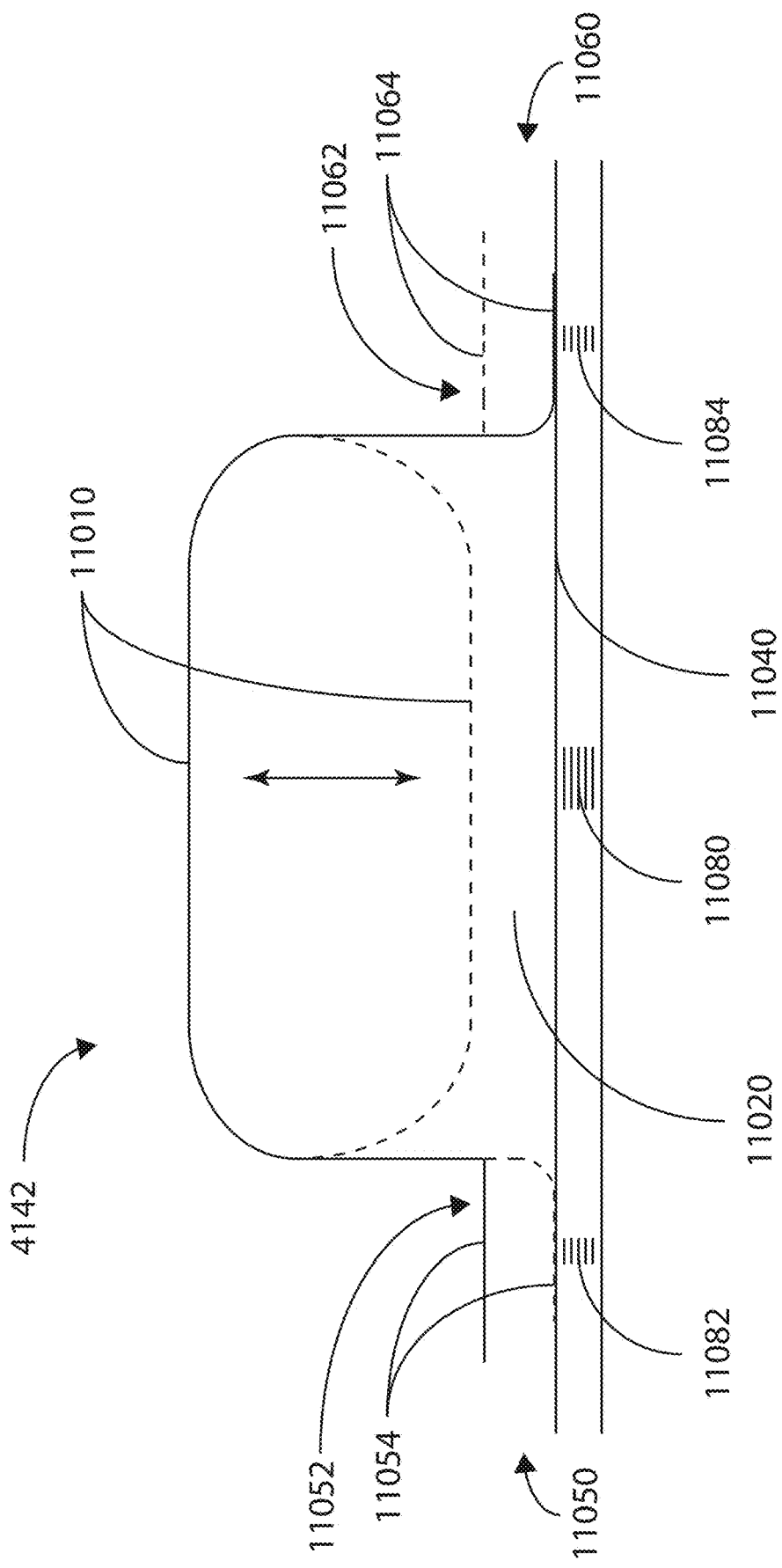

FIG. 11A shows a blower 4142 comprising movable members 11010, 11054 and 11056, wherein the movable members are electromagnetically actuated.

Figure 11B:
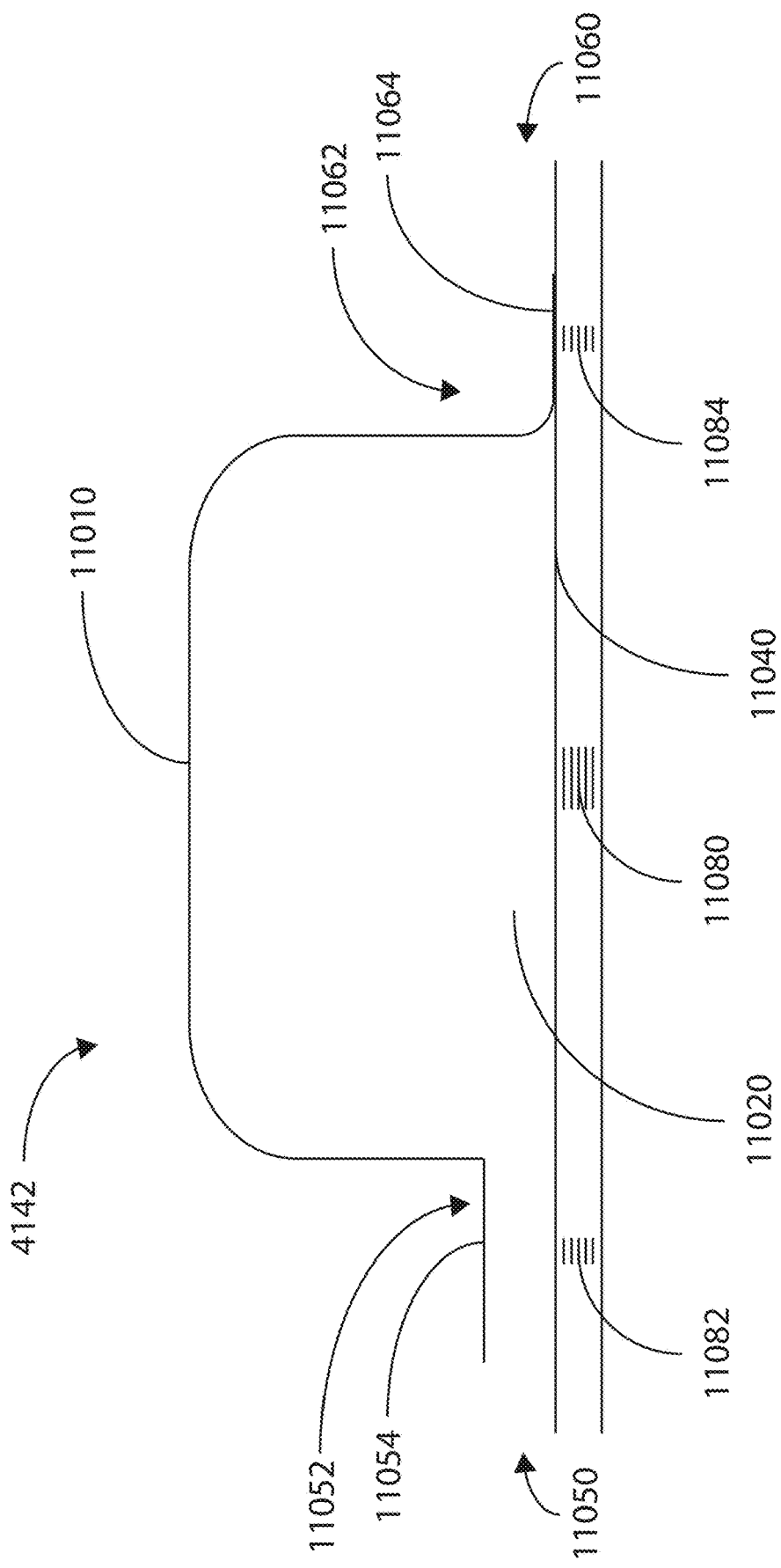

FIG. 11B shows the blower 4142 of FIG. 11A, in an intake configuration.

Figure 11C:
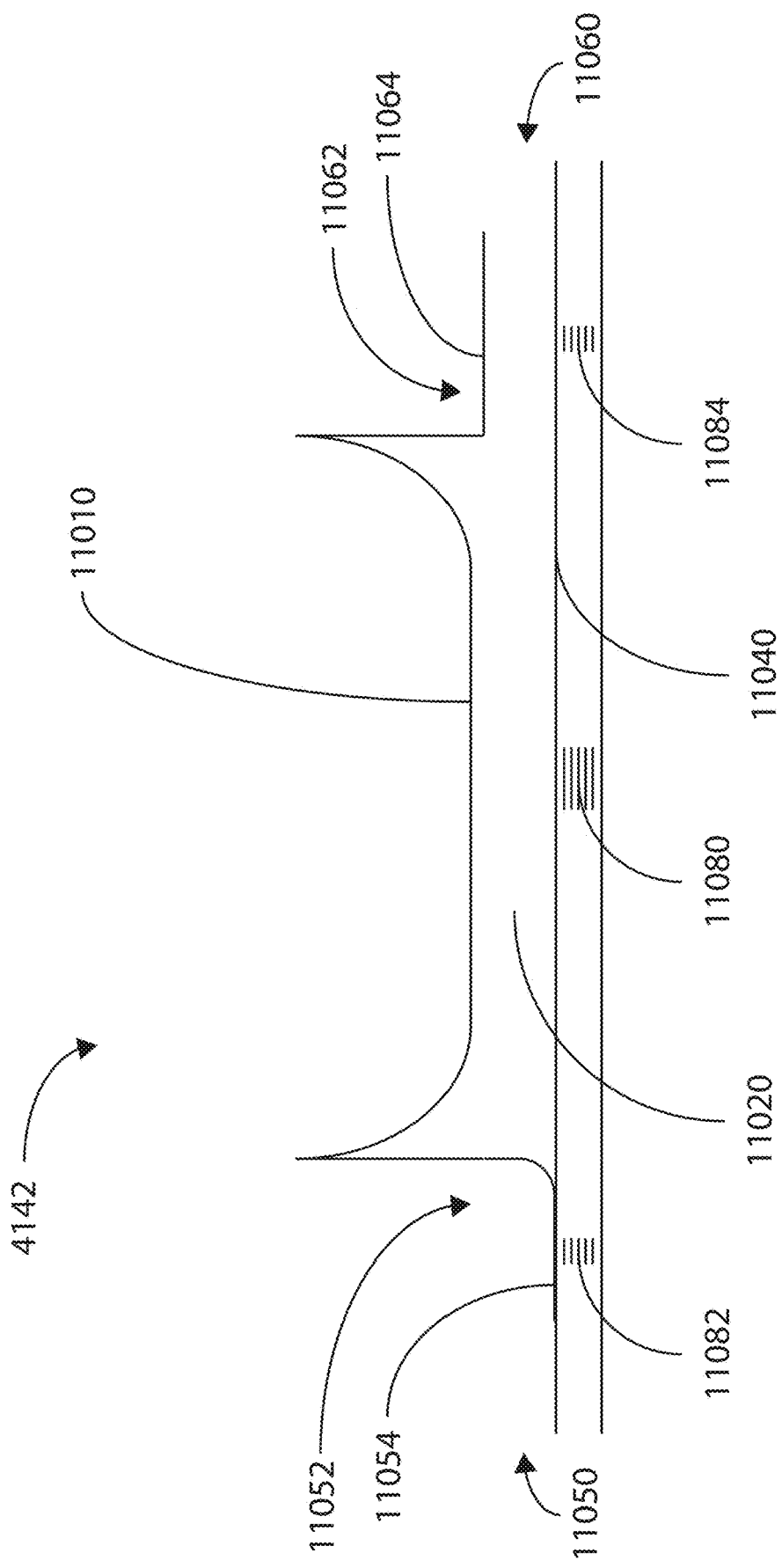

FIG. 11C shows the blower 4142 of FIG. 11A, in an exhaust configuration.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Blower
5.1.1 Introduction

One aspect of the present technology relates to a blower for generating a flow of air, such as at a positive pressure. The blower may be suitable for use in a respiratory pressure therapy device, such as a PAP device or a ventilator. As described above, prior art blowers include motor-driven blowers wherein components are moved (e.g. rotated) by the motor to generate the flow of air. Such blowers may have disadvantages of being one or more of highly complex, expensive, heavy, and difficult to repair.

5.1.2 A Blower With Deformable Members

According to one form of the present technology, the blower may comprise one or more deformable members configured to convert between a first configuration and a second configuration to generate the flow of air.

A deformable member may be converted (or actuated) between the first and the second configuration by electrical energy, such as by application, variation or cessation of application of electrical energy to the deformable member.

In some forms of the present technology, the blower may comprise one or more actuators configured to convert or actuate the deformable member between the first and the second configurations. An actuator, or an actuating portion, may be a separately arranged to, or may be integrated with, the deformable member. The actuator may then motivate a controllable portion of the deformable member, such as by generating, or varying an electromagnetic force.

The deformable member may convert between the first configuration and the second configuration to create a pumping action, such as by the deformable member at least partly defining a chamber of the blower. Thus the pumping action may be performed cyclically to draw in air to the chamber and to expel air from the chamber, whereby a continuous, periodic flow of air may be generated by the blower. The flow of air produced may be at a positive pressure.

The chamber of the blower may be defined by one or more walls (e.g. including the deformable member). The chamber may comprise one or more openings which function as air inlets and/or outlets. The one or more walls that define a chamber of the blower may also form a part of an external housing of the blower 4142, although the one or more walls may be separate to the housing, such as being located internal to the housing of the blower 4142.

According to another aspect, a deformable member may be configured to engage a rigid portion, such as a wall, for at least a portion of a pumping cycle. In one exemplary arrangement, shown in FIG. 6K, at least a portion of the deformable member 6010 may conform to a chamber wall 6040 in a first configuration (shown in dotted lined) and conform to a chamber wall 6140 in a second configuration (shown in solid lines).

Thus, in some forms of the present technology, one or more rigid walls may at least partly define a chamber in a first configuration, and in a second configuration, engage a deformable member of the chamber to at least partly define its shape in a second configuration. Accordingly, such an approach may enable further complexities for the chamber.

A deformable member may be rigidly connected to the housing of the blower 4142, such as directly secured to the housing, or through another portion of the housing, such as a wall defining a chamber of the blower. For example, the deformable member may be connected to the housing by a fastener such as a screw or a bolt, bonded by an adhesive, or clamped onto the housing.

A deformable member may be indirectly coupled to the housing of the blower 4142, such as through intermediate portions that are connected to the housing of the blower 4142. The deformable member may be connected to the housing via a mounting portion such as a bracket, or an intermediate housing.

It is noted that the term 'deformable member' is not intended to be limited to a discrete element or a component. A 'deformable member' in the context of the present document may include a portion of a single structure, wherein the portion is deformable. That is, 'deformable member' and 'deformable portion' are to be understood to be interchangeable.

Thus, it is also to be understood that the whole of a deformable member may not be deformable. Additionally, or alternatively, a deformable member may not be uniformly deformable throughout. For example, a deformable member may comprise a plurality of sections, wherein a first section is constructed to be more rigid than a second section. The term 'deformable member' for the purposes of the present document is used to describe a portion that deforms to create a pumping motion as described herewithin.

Exemplary actuation means/materials for deformable members may include, but not be limited to: electroactive polymer (EAP), piezoelectric, electrostatic, thermo-pneumatic, bimetallic, shape-memory alloys, ion-conductive polymer film (ICPF), electromagnetic, magneto-hydrodyamic, electro-hydrodynamic, electroosmotic, electrowetting, bubble type and electrochemical.

The particular implementation details and requirements in producing a blower using each of the exemplary actuation means/materials listed above may vary. Thus, some of the actuator technologies described above may be more suitable than others for a particular blower construction. An actuation means/material may be selected depending on a number of factors (e.g. size, geometry, displacement, response frequency, costs) relating to the blower and its chambers.

For example, EAP may be a more suitable material than a piezoelectric material for building a blower comprising a small number of chambers, such as between two to ten chambers. In another example, a piezoelectric material may be more suitable than an EAP if the blower was to comprise a high number of small chambers, such as between twenty and one hundred, or operating at a high frequency.

In another example, a deformable member comprising an EAP may be coupled to a biasing means, such as a spring. An EAP may be convertible between a relaxed state and an activated state. Thus, a deformable member using an EAP as an actuating means may comprise or be connected to a biasing means to constrain the deformable member while the EAP is in its relaxed state.

In some forms, ion conductive polymer film (ICPF) may be a suitable material for a deformable member in a low-power, fast response blower, for example comprising a plurality of small chambers.

A deformable member according to one aspect of the present technology may comprise a plurality of layers or portions, such as comprising a plurality of materials.

In one form, a deformable member may comprise a first, passive material encapsulating a second, controllable material, such as an elastic membrane encapsulating a magnetic material. The elastic membrane may comprise one or more magnets, such as distributed therethrough along its length, or located at or distributed around a centre of the deformable member. The elastic material may for example comprise silicone or a thermoplastic elastomer (TPE).

In another form, the deformable member may comprise an electromagnet encapsulated in an elastic material. In yet another form, the deformable member may comprise a metallic material coupled to a controllable material. For example, the deformable material may comprise a steel sheet configured to move between the first and second configurations, while remaining below its fatigue limit.

The deformable member may comprise one or more stiffening portions. For instance, the deformable member may comprise a polymeric sheet, or a metallic sheet, configured increase a stiffness of the deformable member.

As described elsewhere in the present document, a stiffness of the deformable member may be chosen by a designer according to the desired characteristic thereof, such as based on a number and a size of the chambers. Therefore, a construction of a deformable member comprising a first, passive portion, a second, controllable portion, and a third, stiffening portion may provide a designer with ample flexibility in a stiffness of the deformable member, its weight, and properties of the controllable portion.

For example, by varying a stiffening portion, the deformable member may be configured such that its natural frequency is relatively low, such as 2 Hz, 5 Hz, 10 Hz or 20 Hz, or such that its natural frequency is relatively high, such as 1 kHz, 2 kHz, 5 kHz or 10 kHz. Of course, any other values may be also suitable.

The blower may further comprise an electromagnet configured to actuate the deformable member, such as to one or more of possible configurations in order to generate the flow of air.

An exemplary arrangement is shown in FIG. 6M, showing a deformable member 6010, the deformable member comprising an elastic portion 6012 and a controllable portion 6014. The blower 4142 in FIG. 6M further comprises two actuators 6080 and 6180, wherein each actuator is located at or near the deformable member 6010 at a starting configuration the exhaust portion of a pumping cycle.

In the arrangement of FIG. 6M, the elastic portion 6012 may be a silicone membrane, and the controllable portion 6014 may be a magnet, or a plurality of magnets. Further, the actuators 6080 and 6180 may be electromagnets, which may be coupled to a controller configured to actuate the deformable member 6010 to generate the flow of air. Thus, the actuators 6080 and 6180 may attract or expel the controllable portion 6014 as required, such as cyclically, to actuate the deformable member 6010.

In some forms, the blower 4142 may further comprise a biasing portion such as a spring, coupled to the deformable member. The biasing portion may be configured to resist movement of the deformable member away from the actuator. FIG. 6N shows such an exemplary arrangement, wherein the blower 4142 comprises a first spring 6072 and a second spring 6074 coupled to the deformable member. Such biasing portions may be beneficial where the actuation mechanism may comprise a variable efficacy, such as according to distance between the actuator 6080 and the controllable portion 6014.

Delivery of the air using a blower comprising deformable members as described throughout the present application may present advantages over conventional prior art blowers. A blower comprising deformable members may exhibit advantageous properties in power consumption and complexity for example by being more efficient and/or simple, thus potentially consuming less energy and/or being cheaper to manufacture or repair.

5.1.3 A Blower Chamber Operation

A typical pumping cycle of a blower comprising a single chamber may comprise an intake portion during which air is being introduced (e.g. sucked) in to the chamber and an exhaust portion wherein air is being delivered (e.g. pushed) from the chamber. An air flow may thus be generated by the chamber as a result of each pumping cycle, such as at a positive pressure. In some forms, where the blower comprises a plurality of chambers (as will be described further below), a pumping cycle comprising an intake portion and an exhaust portion may be identifiable for each chamber, and a pumping cycle for a blower 4142 may be different to a pumping cycle for an individual chamber. Accordingly, each chamber may produce an air flow, which may be aggregated for a blower 4142, for example through a single blower outlet as described in further detail elsewhere in the present document.

One example of the blower 4142 is shown in FIG. 6A as a schematic. The deformable member 6010 (e.g. a membrane) is shown in FIG. 6A to be convertible between a first configuration and a second configuration to pump the chamber 6020.

In a first configuration (shown as a solid line in FIG. 6A), the deformable member may be curved in a first direction (towards an exterior of a chamber 6020) to increase a volume of a chamber 6020 of the blower, and in a second configuration (shown as a dotted line in FIG. 6A), the deformable member may be curved in the opposite direction (towards an interior of the chamber 6020) to reduce the volume of the chamber 6020 of the blower.

By converting between the first configuration and the second configuration, such as cyclically, the blower 4142 may pump a flow of air by cyclically drawing in and expelling air. Thus, the blower 4142 may receive air through the blower inlet 6050 and deliver a flow of air through the blower outlet 6060 by the aforementioned pumping action. The boundary of the chamber 6020 of the blower may be defined by chamber walls 6040 as well as the deformable member 6010. In some forms, as shown in FIG. 6K, a chamber wall 6040 may partly define the chamber in one configuration and define a shape of the deformable member 6010 in another configuration. Thus, the chamber wall 6040 may define the interior of the chamber only during a portion of a pumping cycle.

As described previously, the chamber walls 6040 as well as the deformable member 6010 may form parts of a housing of the blower 4142, and the blower 4142 may comprise an external housing that at least partially covers the chamber walls 6040 and/or the deformable member 6010.

Thus, in some forms, a portion or the entirety of each of the deformable member 6010 and/or chamber walls 6040 may be internally located to an external housing of the blower 4142.

As described elsewhere in the present document in greater detail, a blower 4142 may comprise a plurality of chamber walls and/or deformable members. In such a configuration, some of the chamber walls and/or the deformable members may form parts of a housing of the blower, while others may be internal to the blower.

In other forms of the present technology, the deformable member may be converted between a first configuration and a second configuration to move another component of the blower 4142, thereby creating a pumping action. For example, a deformable member 6010 may be connected to a movable wall 6030 (see FIG. 6B), to increase or decrease a volume of a chamber 6020 of the blower to generate the flow of air from the blower.

In some forms of the present technology, the deformable member may be configured to oscillate (e.g. to pump) at or near one or more of its resonant frequencies. For example, operating the deformable member at its resonant frequency may allow the deformable member to oscillate at an increased displacement and/or efficiency.

In some forms, the blower may be configured to operate at a frequency that is inaudible or substantially inaudible to reduce disturbance to the users and/or patients. Thus, in some forms, the blower may comprise a set of deformable members configured to oscillate at a frequency of approximately 20,000 Hz (20 kHz) or higher, where the frequency may be a resonant frequency of at least some of the set of deformable members. Alternatively, the blower may comprise a set of deformable members configured to oscillate at a sufficiently high frequency such that it is highly attenuated to most humans.

In other forms, the deformable member may be configured to oscillate at a relatively low frequency. A blower may comprise a deformable member configured to pump at a frequency such as 2 Hz, 5 Hz, 10 Hz, or 20 Hz for example.

According to one aspect of a present technology, the blower may comprise a chamber configured to operate (e.g. pump) at a first frequency, the chamber comprising a deformable member capable of deforming (or responding) at a second frequency. The second frequency may be higher than the first frequency, such that the deformable member may be controlled within a pumping cycle of the chamber.

In one example, an operating frequency of the chamber may be 5 Hz, the chamber comprising a deformable member controllable at a rate of up to 100 Hz. Then, a controller receiving a signal from a sensor (e.g. a pressure signal, at a rate of 1 kHz) may be able to dynamically control a movement of the deformable member within a cycle of the chamber, based on the received pressure signal.

For instance, the controller may adjust a swept volume of the deformable member during a pumping cycle, such as to reduce it or to increase it, from a predetermined value. A blower 4142 comprising a deformable member 6010 as shown in FIG. 6L may initiate an exhaust portion of a cycle at time $t_1$ when the deformable member 6010 is at a first position 6010-1.

Then, the deformable member 6010 may be configured to move to a second position 6010-2 at the end of the exhaust portion of the cycle at time $t_1+t_e$, wherein $t_e$ is the length of the exhaust portion of a pumping cycle. For a chamber operating at 5 Hz, $t_e$ may be approximately 0.1 s. For a deformable member 6010 controllable at 100 Hz, for example, a controller may be able to affect the movement of the deformable member 6010 every 0.01 s, thus the controller may control the deformable member 6010 to finish the exhaust portion of the cycle at a third position 6010-3.

Similarly, those skilled in the art would understand that a number of other in-cycle adjustments may be possible.

5.1.3.1 Valves

The blower 4142 may comprise one or more valves, such as an inlet valve 6052 or outlet valve 6062 as shown in FIG. 6B. The inlet valve and/or the outlet valve may open, close or control a fluid communication (e.g. of air) between a chamber and the atmosphere.

Use of the one or more valves may increase an efficiency of the blower 4142, for example by preventing air from travelling in a reverse direction (e.g. into a chamber through an outlet during an intake portion of a pumping cycle), or preventing air from leaking through a valve that may reduce a flow/pressure produced by the blower 4142.

The valves may be one-way valves, such that for example, the inlet valve 6052 may only allow a flow of air from the outside of the blower to the chamber 6020, and the outlet valve 6062 may only allow a flow of air from the chamber 6020 to the outside of the blower.

In another form, the one or more valves (e.g. valves 6052 and 6062) may be configurable between at least two states, such as shown in FIG. 6B, for example to convert between the two states according to a configuration of the deformable member 6010. For example, the valves 6052 and 6062 may be electrically actuated, such as between a closed state and an open state, and/or to any degree of openness therebetween.

As shown in FIG. 6B, the inlet valve 6052 may open when the deformable member 6010 increases a volume of a chamber 6020 (e.g. during an intake portion of a cycle), while the outlet valve 6062 may close (6052, 6010 and 6062 all shown in solid lines to indicate an 'intake' configuration). Also, the inlet valve 6052 may close when the deformable member 6010 reduces a volume of a chamber 6020 (e.g. during an exhaust portion of a cycle), while the outlet valve 6062 may open (6052, 6010 and 6062 all shown in dotted lines to indicate an 'exhaust' configuration).

A valve may comprise a deformable member, such as an EAP, electromagnetic or a piezoelectric material. In one form, the valve may comprise a deformable member configured to move between a first position and a second position to open and/or close the valve.

FIG. 6H shows an exemplary schematic of a blower 4142 according to the present technology, comprising an inlet valve 6052 and an outlet valve 6062, wherein each valve comprises a deformable member 6054 and 6064 respectively. Each deformable member 6054 or 6064 may move to open and/or close the respective valve.

The deformable members 6010, 6054 and 6064 are shown as solid lines in FIG. 6H to indicate a first configuration and in dotted lines in FIG. 6H to indicate a second configuration.

In FIG. 6H, when the deformable members 6010 of the chamber 6020 is moving towards a first configuration to increase the volume of a chamber 6020 of the blower, the inlet valve 6052 may be open, and the outlet valve 6062 may be closed. Also, when the deformable member 6010 of the chamber 6020 is moving towards a second configuration to decrease the volume of a chamber 6020 of the blower, the inlet valve 6052 may be closed, and the outlet valve 6062 may be open.

By way of example, the deformable members 6010, 6054 and 6065 shown in FIG. 6H may all comprise an EAP, and movable between a first configuration and a second configuration. Additionally, or alternatively, the deformable members 6010, 6054 and 6065 shown in FIG. 6H may all comprise a piezoelectric material, and movable between a first configuration and a second configuration. In yet another form, the deformable members 6010, 6054 and 6065 shown in FIG. 6H may comprise a magnetic material. It will of course be understood that a mixture of materials may be suitable.

In arrangements of a blower 4142 wherein a deformable member 6010 for pumping as well as a deformable member 6054 and/or 6065 are actuated by electromagnetic forces, a single electromagnet may be configured to actuate a plurality of deformable members, such as to pump and open and/or close a valve.

In some forms of the present technology, such as wherein the set of deformable members for the chamber (chamber deformable members) are oscillating at a high frequency (e.g. a piezoelectric membrane vibrating at an ultrasonic frequency such as at 20 kHz), any valves in the blower may also be configured to operate at a similar high frequency. In some forms, a valve may be configured to operate or an even higher frequency than a set of chamber deformable members such that the valve may respond faster than the set of chamber deformable members. A plurality of deformable members A blower may comprise a deformable member convertible between a first configuration and a second configuration to pump a chamber, as well as to act as a valve. The example of FIG. 6K shows a deformable member 6010 partly defining a first chamber 6020 and a second chamber 6120. The deformable member 6010 can be seen to be convertible between configurations to pump air from the chambers 6020 and 6120. It can be also seen that the deformable member 6010 is selectively blocking inlets 6050 and 6150 from the chamber 6020 and 6120 respectively, as well as selectively blocking outlets 6060 and 6160 from the chamber 6020 and 6120 respectively. Blower outlet 6060, 6160 may include a one-way valve, whereas blower inlet 6050, 6150 may not include a valve or a one-way valve.

In some forms of the present technology, arrangement of stationary componentry may be used to effectively act as valves. One such example may be a Tesla valve, and another may be a system that utilises inertia of the flow of air as described in U.S. Pat. No. 8,678,787, wherein air flow is maintained in a single direction.

5.1.3.2 Blower Comprising a Plurality of Deformable Members

In some forms, a blower 4142 may comprise a plurality of deformable members 6010, such as two deformable members 6010 and 6110 as shown in FIG. 6C. In the arrangement shown in FIG. 6C, each of the deformable members 6010 and 6110 are configured to increase or reduce a volume of the chamber 6020 which is defined by both of the deformable members 6010 and 6110.

The deformable members 6010 and 6110 may be identically sized and configured to move in concert so that they increase a volume of a chamber 6020 or reduce the volume of the chamber 6020 at the same time as each other. In other forms (not shown), at least one of a set of deformable members 6010 and 6110 may be sized and/or configured differently from each other while being configured to increase or decrease a volume of a common chamber 6020.

A deformable member may comprise a material that may be convertible between a first configuration and a second configuration by electrical energy (e.g. EAP, piezoelectric, electrostatic, ICPF). For example, a deformable member may comprise a suitable material that can be converted from a first configuration to a second configuration by application (e.g. of a predetermined magnitude) of electrical energy, which may be applied as a current. Additionally, or alternatively, the deformable member may be configured to convert between the first configuration and the second configuration by cessation of application of a current.

Some arrangements of the present technology may further comprise a capacitive member configured to maintain a deformable member in a particular configuration by retaining electrical energy in the capacitive member. In such an arrangement, a deformable member may be retained in a particular arrangement without requiring a further application of electrical energy, which may improve a power efficiency of the blower.

Furthermore, a deformable member suitable for the present application may also be capable of deforming to the magnitudes required to pump air at a sufficient flow rate. The deformable member may also be capable of performing a required number of pumping cycles, such as throughout a life of an RPT device.

Electroactive polymers and piezoelectric materials may be suitable examples of the deformable member in some implementations of the present technology. Thus, a blower as shown in FIG. 6A for example may comprise a deformable member 6010 comprising a membrane composed at least partly of an electroactive polymer (EAP). Thus, upon application of an electrical current, it may move from a first configuration (e.g. as shown in solid lines) expanding the size of the chamber 6020 to a second configuration (e.g. as shown in dotted lines) reducing the size of the chamber 6020.

In some forms, a deformable member may comprise an EAP and a biasing member (e.g. a spring). The deformable member may be in a first configuration wherein the EAP is in a relaxed state, and the biasing member substantially determines a shape of the deformable member. In a second configuration, the EAP may be in a tense state whereby the EAP substantially determines a shape of the deformable member.

One advantage of a deformable member at least partially comprising a membrane may be a reduced weight, and thus an increased responsiveness of the deformable member. Another advantage may be that due to a low thickness of a membrane, the stress caused in the deformable member may be maintained at a low level as the deformable member is arranged in a curved configuration as shown in some examples of the present technology.

A blower 4142 according to the present technology may be alternatively or additionally configured to respond to a variation in pressure that may be caused by a change in external conditions. For example, the blower 4142 may be configured to respond to a patient's breathing, so that a predetermined condition may be maintained at the destination of the air flow (e.g. at an entrance to a patient's airways). To maintain the predetermined condition, a pressure sensor 4272 may measure a pressure of the air flow generated by the blower 4142, and the blower 4142 may adjust an operation (e.g. frequency and/or amplitude) of the deformable members accordingly. For example, a pressure sensor 4172 may be configured to determine an air pressure at or near an outlet of the blower 4142 (e.g. as shown in FIG. 6G), and the operating frequency or amplitude of the deformable member 6010 may be adjusted according to the reading of the pressure sensor, such as decreasing an amplitude of movement of the deformable member as a response to an increase in the pressure measured by the pressure sensor.

In one example, a blower 4142 may comprise a total chamber volume of approximately 0.08 L, of which a swept volume may be 0.05 L. Such a blower may operate at a frequency of 40 Hz, to produce a flow rate of 120 L/min which is a typical maximum flow rate required for a PAP device. Of course, the specific flow rates, chamber volumes, operating frequencies, swept volumes etc. may vary according to particular design specifics and requirements of the apparatus using the blower.

As described above, such a blower comprising deformable members and configured to generate an air flow through movement of the deformable members may be more power efficient than prior art blowers, such as those comprising rotating componentry (e.g. centrifugal and/or axial blowers). Advantageously, a blower comprising deformable members may exhibit reduced levels of air leakage than that may occur around and/or past any impellers on the prior art blowers. Furthermore, the inherent aerodynamic inefficiencies (e.g. static regain, centrifugal processes) of a prior art blower wherein the air flow through various rotating componentry may be removed, thereby improving a power efficiency of the blower.

Another advantage of a blower comprising one or more deformable members as described herein may be that the inertia of the moving component may be reduced in comparison to a blower that comprises a rotational component. Thus, such a blower comprising deformable members may be able to respond to changing conditions with improved quickness than conventional blowers.

5.1.4 Blower Sensing/Controls

A blower 4142 (and/or a control system for the blower 4142, e.g. central controller 4230) as described herein may be operated based on one or measures from one or more sensors, such as a pressure sensor 4272 (e.g. as shown in FIG. 6G). In one form, the pressure sensor may be configured to produce one or more measures of pressure of the air flow generated by the blower, for example by measuring a pressure near the blower outlet 6060. It may also be possible to use a pressure sensor 4272 to measure a pressure at another point within the same pneumatic path as the blower 4142, such as in an air circuit 4170 and/or at the patient interface 3000, to control an operation of the blower 4142.

The pressure measures may be used to control the output of the blower 4142, such as to decrease an output of the blower 4142 in response to a pressure measure that is above a threshold, or to increase an output of the blower 4142 in response to a pressure measure that is below a threshold.

The blower 4142 according to some arrangements of the present technology displaces a predetermined volume of air according to a movement of the deformable member. Accordingly, a pressure of the air flow generated by the blower 4142 may be related to the flow rate of the air flow generated by the blower 4142.

Thus, in an aspect of the present technology, the pressure sensor 4272 may be used to determine a flow rate of air flow from the blower 4142. Alternatively, or additionally, a measure of pressure from a flow rate sensor 4274 may be used to determine a pressure of the air flow from the blower 4142. Accordingly, it may be possible for only a pressure sensor 4272 or a flow rate sensor 4274 to be utilised in order to determine a pressure and a flow rate of the air flow generated by the blower 4142.

Furthermore, only one of the pressure sensor 4272 and the flow rate sensor 4274 may be used to control the blower 4142, whereas in many cases with a prior art blower, both a pressure sensor 4272 and a flow rate sensor 4274 may be required to achieve an equivalent level of control (e.g. generate an air flow with particular output characteristics).

An air flow generated by the blower 4142 according to an aspect of the present technology may be represented by a waveform, such as of a flow rate against time, or a pressure against time. The waveform may be dependent on not only a first configuration and a second configuration that a deformable member (e.g. deformable 6010 as shown in FIG. 6A) is convertible between, however also the path taken by the deformable member therebetween. Therefore, by manipulating, or configuring, the sequence, path and/or progression of the deformable member between the first configuration and the second configuration, characteristics of the air flow generated by the blower 4142 may be controlled.

In some arrangements, a deformable member may be configured to deform between a first configuration and a second configuration in a predetermined sequence and/or progression, such as in a non-linear fashion, or in a linear fashion, for example with respect to time. For example, as a deformable member deforms from the first configuration to a second configuration, the electrical energy applied to the deformable member may vary, for example in a non-linear fashion with respect to time. In some forms, one or more of a rate of deformation by the deformable member, a velocity of movement by a portion connected to the deformable member, or a volume swept by a deformation of the deformable member may be non-linearly configured.

A number of movement 'templates' may be used for the deformable member, such as a sine, a trapezoidal, or a square wave form. As described elsewhere in the present document, a movement of a deformable member may be adjusted dynamically (within a single cycle) in some configurations, as well as between cycles.

In one form, a progression of the deformable member's conversion between the first configuration and the second configuration may be such that the rate of volume being swept by the deformable member is substantially constant. In another form, the deformable member may convert between the first configuration and the second configuration by maintaining a constant rate of ratio change to a volume of the chamber.

Yet further, the deformable member may convert between the first configuration and the second configuration at a rate that depends on a measure, such as a measure of pressure obtained by a sensor such as the pressure sensor 4272 shown in FIG. 6G. Other measures such as a measure of respiration, a measure of flow rate (e.g. through a vent, through a leak and/or through the RPT device) or any other measures relevant to an operation of a RPT device and/or provision of respiratory therapy may be also applicable. So, in one example, the rate of deformation by the deformable member may be non-linear throughout a cycle. In some forms, the rate of deformation may be predetermined, however in other forms, the rate of deformation may not be predetermined, such as where the rate of deformation may be determined according to a measure from a pressure sensor 4272.

The sequence, path and/or progression of the deformable member between configurations may be determined not only by movement of the deformable member alone, but also by a configuration of the chamber, the volume of which the deformable member modifies.

5.1.5 A Blower Comprising a Plurality of Chambers

A blower 4142 may comprise a plurality of chambers 6020 and 6120, for example as shown in FIGS. 6D and 6E. The plurality of chambers 6020 and 6120 may be adjacent to each other as shown in FIGS. 6D and 6E, although in other forms, one or more of the chambers 6020 and 6120 may be located away from each other, such as in separate external housings (not shown). Each of the chambers 6020 and 6120 may be connected to at least one deformable member (6010 and 6110) configured to increase or reduce a size of the chambers 6020 and 6120. The deformable members 6010 and 6110 may be configured to increase or reduce a size of one chamber 6020 and 6120 as shown in FIG. 6D, or a single deformable member 6010 may be configured to simultaneously increase or reduce a size of a plurality of chambers 6020 as shown in FIG. 6E.

Where a blower 4142 comprises a plurality of chambers (e.g. 6020 and 6120), each of the chambers may be homogenously configured such as in volume, shape or dimensions. However, it is also possible that each of the chambers 6020 and 6120 may be configured non-homogenously, so that for example a first chamber may be configured to be larger and/or in a different shape than a second chamber.

Furthermore, one or more of the plurality of chambers may be configured to comprise non-homogenous dynamic characteristics, such as in their expansion/compression characteristics. For instance, a first chamber and a second chamber may be configured to pump a flow of air at a one or more of: varying frequency, phase or air flow rate to each other.

For example, the blower 4142 shown in FIG. 6F comprises a first chamber 6020 and a second chamber 6120. As is shown in FIG. 6F, the chambers 6020 and 6120 may be configured differently to each other in size (e.g. measured in volume), and may each comprise a first deformable member 6010 and a second deformable member 6110 respectively. The deformable members 6010 and 6110 may also be configured differently to each other, such as to have varying amplitudes of movement as shown in FIG. 6F.

FIG. 6G shows an example arrangement wherein air flows from a plurality of chambers 6020 and 6120 may be combined to deliver a combined flow of air through a single blower outlet 6060. In this arrangement, a pressure sensor 4272 may be connected to the blower 4142 near the blower outlet 6060 to measure a pressure of the air flow exiting the blower so that the frequency and/or amplitude of the deformable members 6010 may be adjusted.

The use of a plurality of chambers with one or more non-homogenous characteristics may provide one or more benefits to an operation of the blower 4142.

For example, a blower comprising a single chamber 6020 (e.g. as shown in FIGS. 6A and 6B) may generate a flow of air that pulsates at a frequency corresponding to the movement of the deformable member 6010. That is, if the deformable member 6010 is moving up and down at a frequency of 40 times a second (40 Hz), the resulting air flow that is delivered through the blower outlet 6060 would also pulse at an equivalent frequency. Thus, the magnitude of air delivered through the blower outlet 6060 may vary through the cycle, and in a portion of the cycle during which air is being sucked in (intake portion of the cycle) to the chamber 6020, no air flow may be delivered through the blower outlet 6060 at all.

Thus, an exemplary graph of air flow rate delivered through the blower outlet 6060 by a blower 4142 comprising a single chamber 6020 (e.g. as shown in FIG. 6B) may appear as shown in FIG. 7A. Here, the first air flow rate waveform 7010 represents the amount of air flow rate delivered through the blower outlet 6060. In this form, the outlet valve 6062 prevents any egress of air during a portion of the pumping cycle wherein air is pumped in through the blower inlet 6050 into the chamber 6020. Thus the air flow rate may be zero at times, such as between $t_1$ and $t_2$, and between $t_3$ and $t_4$, as shown in FIG. 7A by the first air flow rate waveform 7010.

Then, during a period of each blower cycle $t_{cycle}$, at least a portion of the period may generate little to no air flow such as $t_{noflow}$ as shown in FIG. 7A. Such a flow regime may not adversely affect operation of the end device that uses the blower in some cases, however in others such a discontinuous flow regime may be disadvantageous to an operation of the end device. One such application where such discontinuous flow rates are undesirable may in respiratory therapies (such as PAP therapies), where the flow volume, rate and/or pressure received by the user/patient may be varied where such discontinuous flow rates are present. Therefore, it may be beneficial to seek to reduce or remove such flow regimes from the generated flow rates altogether.

One way to ameliorate such discontinuous flow rates in the generated air flow by the blower may be utilise a plurality of chambers. For example, a second chamber may be configured to produce a flow of air at an identical period and amplitude to the first chamber, however arranged such that the second chamber operates out of phase to the first chamber, such as by 180 degrees. One such waveform of the air flow is shown in FIG. 7B, where the second air flow rate waveform 7020 is shown. Thus, by combining the two air flows a combined air flow waveform 7030 may be produced as shown in FIG. 7C that reduces the period of no air flow condition to none or close to none.

In another form, the blower may be configured to generate two air flows 7010 (shown in solid lines) and 7020 (shown in dotted lines) as shown in FIG. 7D, where they partly overlap during a period of non-zero air flow, such as during the rise and fall periods respectively (between periods of changing amplitudes). Such an arrangement may result in an output air flow as shown in FIG. 7E, where only a relatively small variation in amplitude can be seen.

Furthermore, in some cases, by introducing one or more additional chambers of smaller sizes, the overall output air flow rates may be further controlled, such as to reduce any fluctuations over time. Thus, the flow of air generated by each of the plurality of chambers 6020 may be combined to generate the overall flow of air with desired characteristics.

In some forms, a blower 4142 may comprise multiple internal chambers, wherein each internal chamber operates out of phase with another internal chamber of the blower, such as by a predetermined amount. For example, a blower 4142 shown in FIG. 8A may comprise four chambers 8020, 8120, 8220 and 8320, each comprising an inlet (8050, 8150, 8250 and 8350 respectively) and an outlet (8060, 8160, 8260 and 8360 respectively). Each chamber may also be connected to a deformable member to generate an air flow through the outlet of the chamber as described herein, wherein the blower outlet (not shown in FIG. 8A) may combine the air flows from each outlets.

Figure 8A:
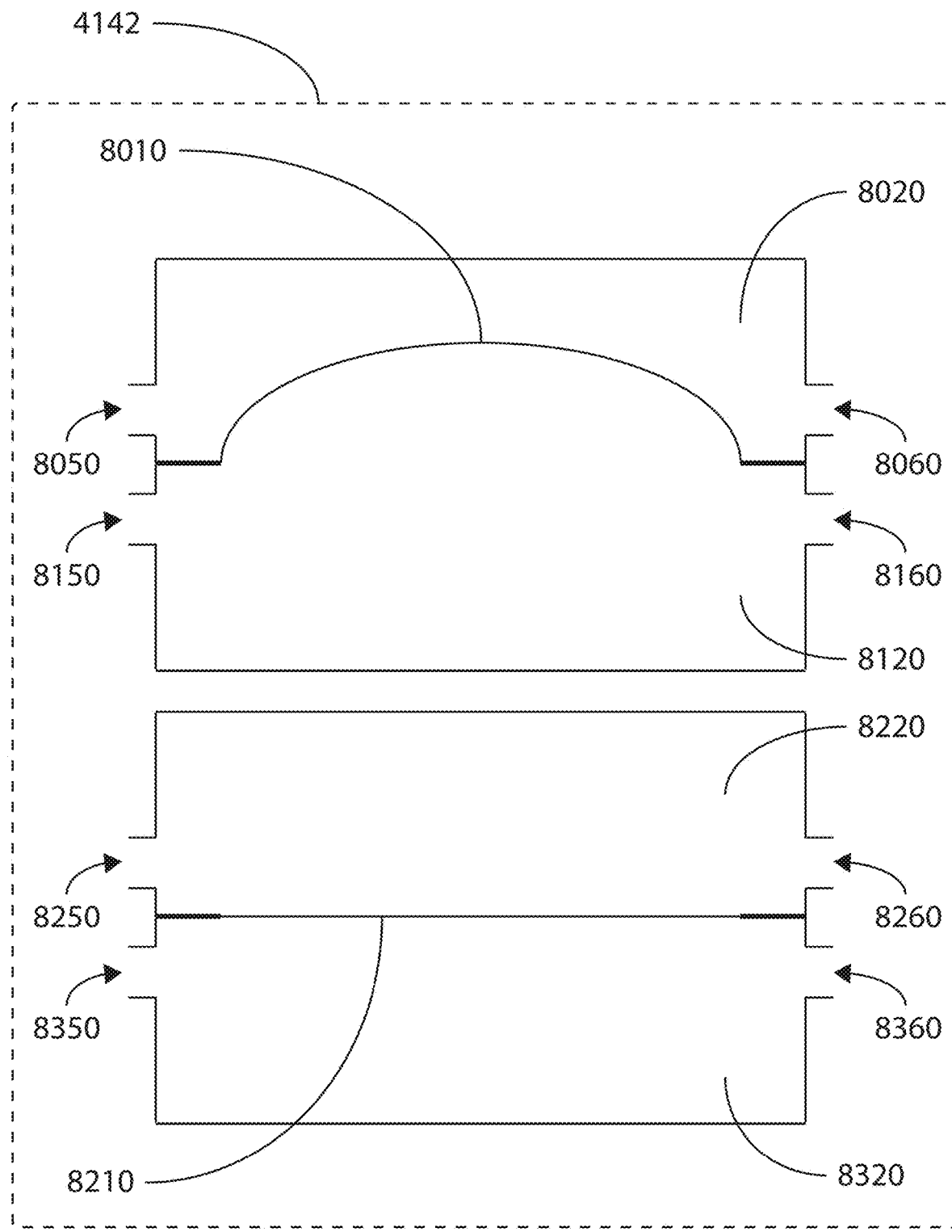
Figure 8B:
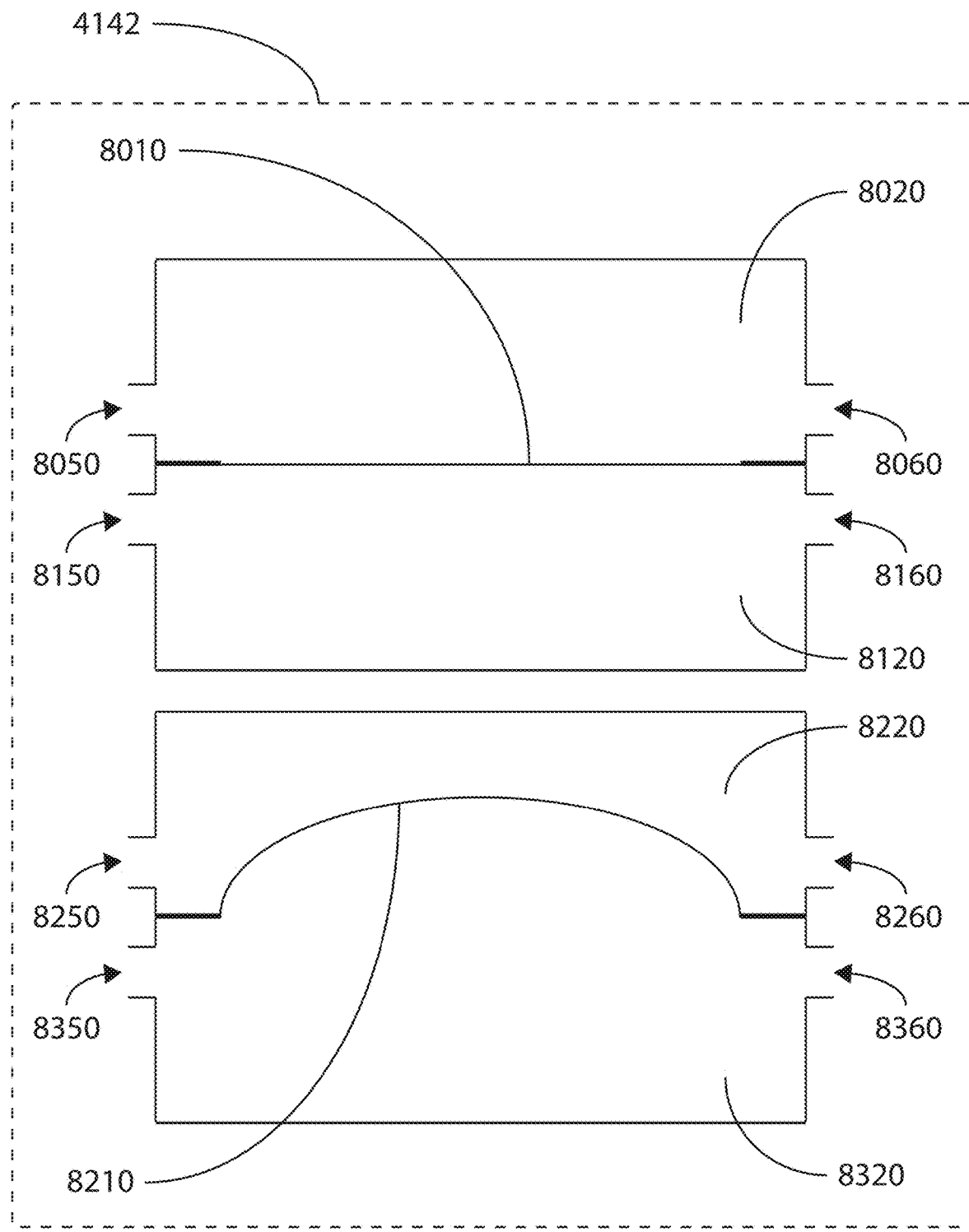
Figure 8C:
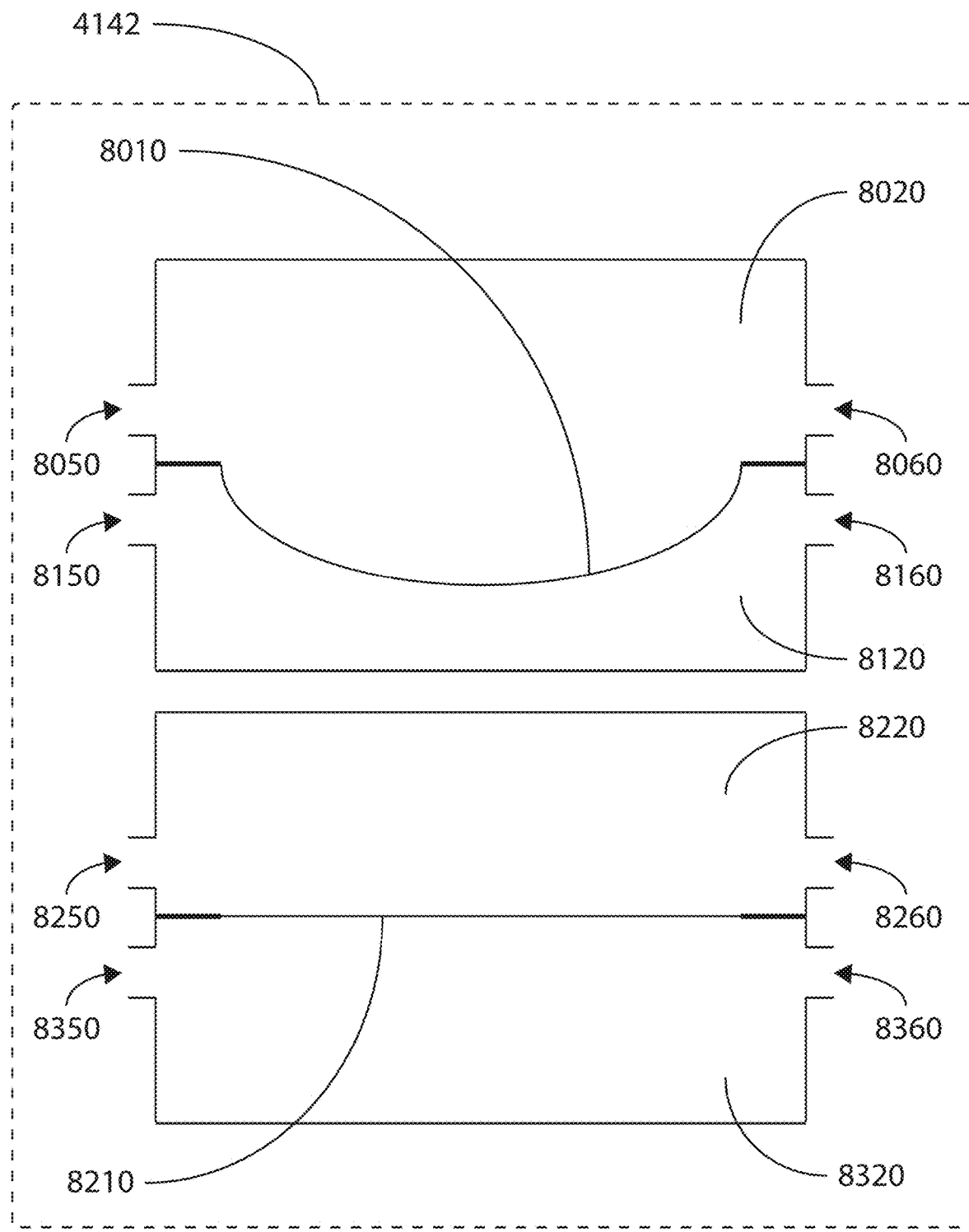
Figure 8D:
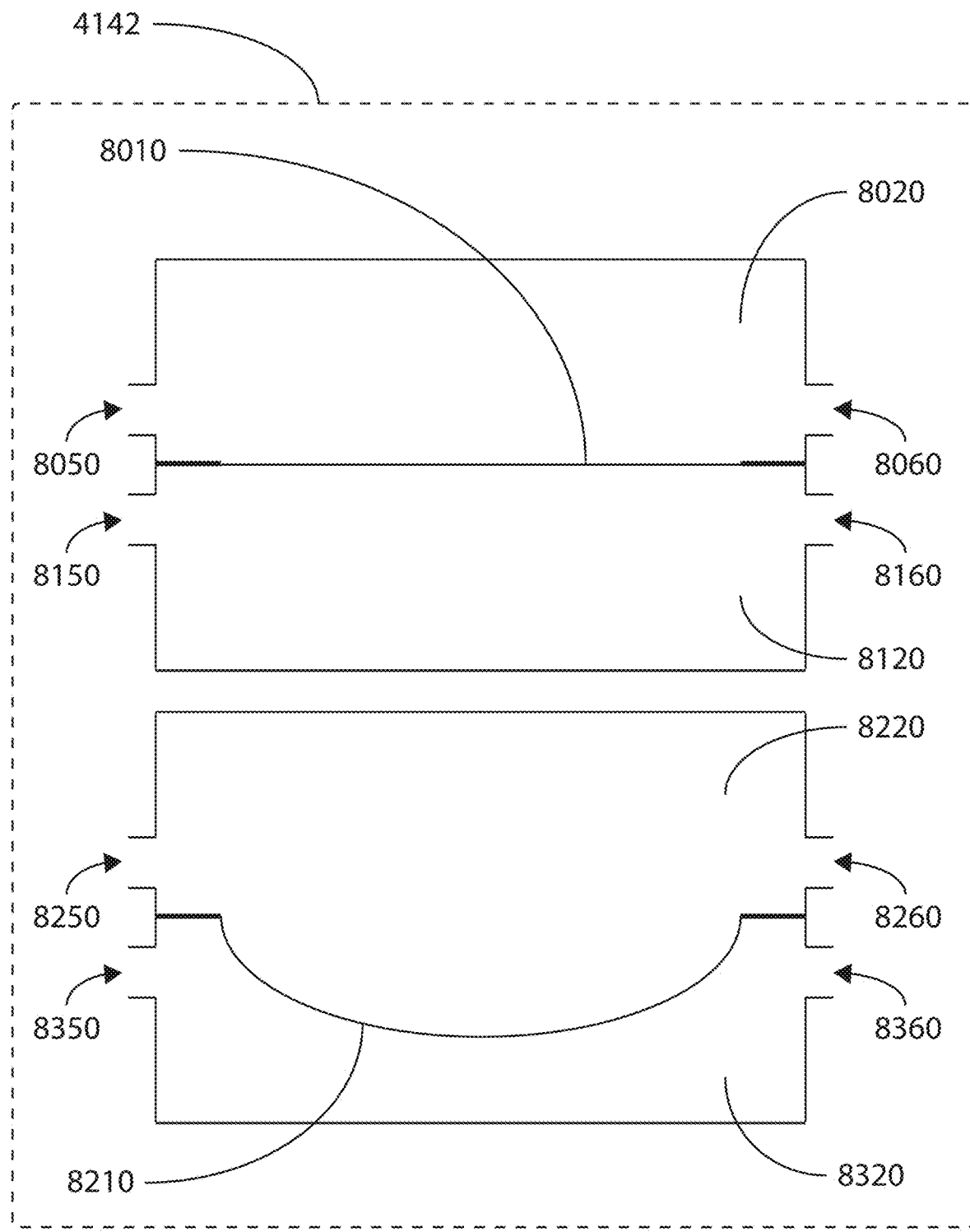

In the form shown in FIG. 8A, the blower 4142 may comprise a deformable member 8010 connected to (and at least partly defining) the chambers 8020 and 8120, and a deformable member 8210 connected to (and at least partly defining) the chambers 8220 and 8320. The deformable members 8010 and 8210 in this form may be configured to operate 90 degrees out of phase with each other as shown in FIG. 8A. Then, the arrangements of the blower 4142 throughout a period of operation (i.e. a pumping cycle of the blower 4142) at 90 degree intervals (e.g. at 0, 90, 180 and 270 degrees) are shown in FIGS. 8A-8D.

In such an arrangement, when at least one of the chambers 8020, 8120, 8220 and 8320 may be at a mid-point of an intake portion of the cycle, and another at a mid-point of an exhaust portion of the cycle, the other two chambers may be at their neutral portions (e.g. "dead centre" positions). Thus, as shown in FIGS. 8A-8D, as the chambers 8020, 8120, 8220 and 8320 cycle through to pump the air flow, advantageously, at no point in the cycle of the entire blower 4142 all chambers may be in their neural positions. This may allow the blower 4142 to deliver an air flow wherein an amount of disruption and/or fluctuations to the flow are reduced (e.g. at a substantially constant flow rate).

It will be thus understood that a blower comprising a plurality, or a set of chambers, each comprising a set (one or more) of deformable members may be used to produce a flow of air according to a desired set of characteristics. One or more of the geometry (e.g. size and shape) of the chamber and/or dynamic characteristics of the chamber (e.g. size and shape of the deformable members, frequency and/or amplitudes of the deformable members) may be determined to produce a blower that meets requirements of a RPT device for example.

It will be thus understood that a range of various examples of blowers may exist in implementations of the present technology. One exemplary blower arrangement may comprise a single chamber as shown in FIG. 6A. Another exemplary blower arrangement may comprise two chambers as shown in FIG. 6D. In another exemplary blower arrangement, the blower may comprise any number of chambers such as between three and one hundred, if not more.

A selection of the number of chambers in a blower may depend on a number of factors. For example, connection of a plurality of chambers to each other may be done in parallel (e.g. as shown in FIG. 6D) or in series (e.g. as shown in FIG. 6I).

Addition of a chamber in series to another chamber in a blower may increase energy (e.g. pressure) of the flow of air produced from the blower. For example, a flow of air exiting the first chamber 6020 in FIG. 6I may be at A cm $H_2O$, and a flow of air exiting the second chamber 6021 in FIG. 6I may be at approximately A+B cm $H_2O$.

It is noted that, without leak, the flow rate of air through a plurality of chambers connected in series may be substantially identical to each other. Thus, in FIG. 6I, the flow rate of air through the first chamber 6020 would be substantially identical to the flow rate of air through the second chamber 6021.

Addition of a chamber in parallel to another chamber in a blower may increase a flow rate of the flow of air produced from the blower. For example, a flow of air exiting the first chamber 6020 in FIG. 6G may have an air flow rate A 1/min, and a flow of air exiting the second chamber 6120 in FIG. 6G may have an air flow rate B 1/min. Thus, the flow from the two chambers may be combined to produce an increased air flow rate of A+B 1/min.

As described elsewhere in the present document in further detail, a blower comprising a plurality of chambers in parallel (e.g. as shown in FIG. 6G) may be driven such that at least some of the plurality of chambers may be driven out of phase with each other.

In some forms, a blower may comprise a plurality of chambers wherein at least some of the chambers are connected in parallel to each other and at least some of the chambers are connected in series to each other, such as in the exemplary schematic of a blower 4142 shown in FIG. 6J. In FIG. 6J, the first top chamber 6020 and the second top chamber 6021 are connected in series to each other, and the first bottom chamber 6120 and the second bottom chamber 6121 are connected in series to each other.

Thus, a blower may comprise a plurality of chambers connected in series, for example to deliver a flow of air at a required pressure level, and/or a plurality of chambers connected in parallel, for example to deliver a flow of air at a required flow rate.

Another exemplary arrangement for a blower 4142 according to the present technology is shown in FIGS. 9A-9G. In this form, the blower 4142 comprises a first housing 9042, a second housing 9044, a deformable member 9010, a first chamber 9020, a second chamber 9120 and a blower outlet 9070. The deformable member 9010 is shown to be connected to the chambers 9020 and 9120 by being rigidly fixed between the first housing 9042 and the second housing 9044, such as through the slots 9030 shown, and/or by adhesives. Where the blower 4142 comprises slots 9030 extending through the deformable member 9010 and the housings 9042 and 9044, one or more fasteners (e.g. bolt and nut, bolt, adhesive fasteners) may be used to couple the deformable member 9010 to the first housing 9042 and/or the second housing 9044.

Each chamber 9020 and 9120 may comprise an inlet (9050 and 9150 respectively), wherein each inlet may comprise a one-way valve (9052 and 9152 respectively) through which a flow of air may be delivered into the chamber however not allowed to exit from the chamber. Each chamber 9020 may comprise an outlet (9060 and 9160 respectively), wherein each outlet's outlet valve (9062 and 9162 respectively) may be a one-way valve to only allow a flow of air to be delivered from the chamber through the outlet.

The one-way valves shown in FIGS. 9E-9G may be constructed from a resilient elastomer, and installed against a rigid member (the housings 9042 and/or 9042 in this example) such that the valve may only be able to deform sufficiently in one direction. Thus, in FIG. 9F, the outlet valve 9062 may only move away from the chamber 9020, as the outlet valve 9062 is restricted from deforming in the direction towards the chamber 9020 due to the first housing 9042.

The blower 4142 may further comprise an outlet collector 9072 that receives air flows from one or more chamber outlets (e.g. 9060 and 9160) and delivers a flow of air from the blower 4142 through the blower outlet 9070. The outlet collector 9072 may be coupled to the housings 9042 and/or 9044, such as by interference fit, fasteners, adhesives or any number of other known methods. The outlet collector 9072 in some forms may be configured as a muffler to reduce a noise produced by the blower 4142, for example by comprising acoustic foam, and/or muffling chambers.

It will be understood that, as described above, the exemplary blower 4142 as shown in FIG. 9A-9G is not intended to be limiting. Thus, for example, a blower 4142 may incorporate aspects from the arrangement shown in FIGS. 9A-9G, and comprise any number of chambers with one or more deformable members as described elsewhere in the present document.

FIG. 11A shows another exemplary arrangement, wherein a blower 4142 comprises a deformable member 11010, an inlet valve 11052 and an outlet valve 11062. The inlet valve 11052 and the outlet valve 11062 may each comprise a deformable member 11054 and 11064 respectively, movable to operate the valves.

Similarly to above, the deformable members 11010, 11054 and 11064 are shown in two states, one in solid lines to denote an intake configuration and another in dotted lines to denote an exhaust configuration. For clarity, FIG. 11B shows the arrangement of FIG. 11A in the intake configuration, and FIG. 11C shows the arrangement of FIG. 11A in the exhaust configuration.

In the configuration shown in FIG. 11A, the deformable members 11010, 11054 and 11064 may be actuated electromagnetically. Thus, the blower 4142 may comprise one or more electromagnets 11080, 11082 and 11084 for example as shown in FIG. 11A, with each of the electromagnets 11080, 11082 and 11084 configured to actuate a deformable member 11010, 11054 or 11064 respectively.

Accordingly, each deformable member 11010, 11054 and 11064 may comprise a magnetic material, such as a ferrous material.

The size and location of each electromagnet and/or the deformable members may be configured according to the required movement. For example, the electromagnet 11080 configured to actuate the deformable member 11010 of the chamber 11020 may be larger than the other two electromagnets 11082 and 11084.

The electromagnets 11080, 11082 and 11084 may be separated from an air path of the blower 4142. For example, the electromagnets may be located behind or in a wall 11040 of the blower, or encased in a silicone or plastic layer.

As described elsewhere in the present document, the deformable members 11010, 11054 and 11064 may be wholly or partially flexible. Thus, in one form, a deformable member may comprise a flexible substrate (e.g. silicone membrane) comprising a distribution of magnetic material such that the deformable member may be actuated by an electromagnet. In another form, a deformable member may comprise a discrete magnetic material (e.g. a steel disc) coupled to a flexible material such that the deformable member may be actuated by an electromagnet.

5.2 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.3 Treatment Systems

In one form, the present technology comprises an apparatus or device for treating a respiratory disorder, such as by providing a flow of air to an entrance of a patient's airways. The apparatus or device may comprise an RPT device 4000 for supplying pressurised air to the patient 1000 via an air circuit 4170 to a patient interface 3000, for example as shown in FIG. 1A. The treatment system may further comprise a humidifier 5000 for humidifying the flow of air.

5.4 Patient Interface

Figure 2A:
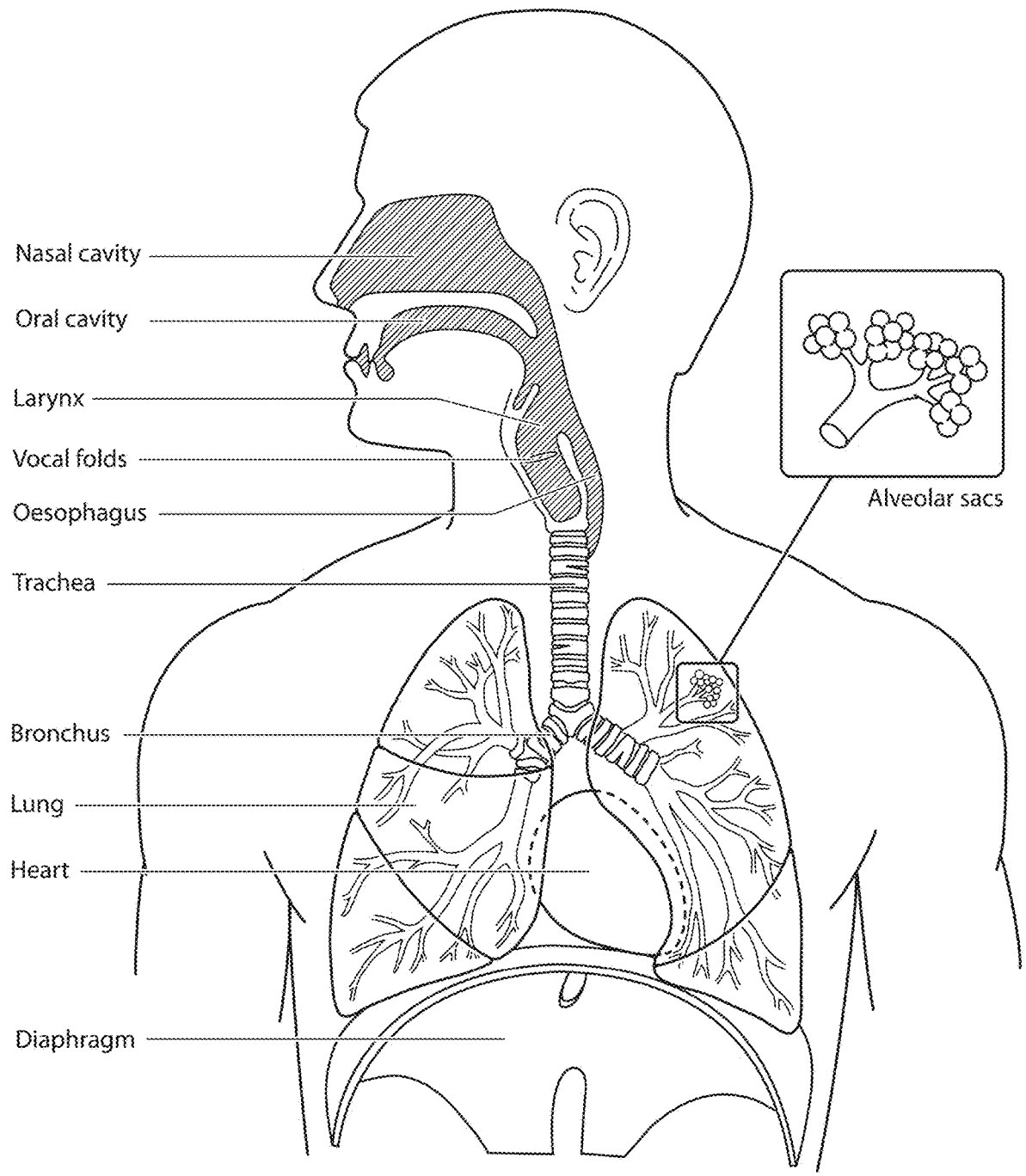
Figure 3A:
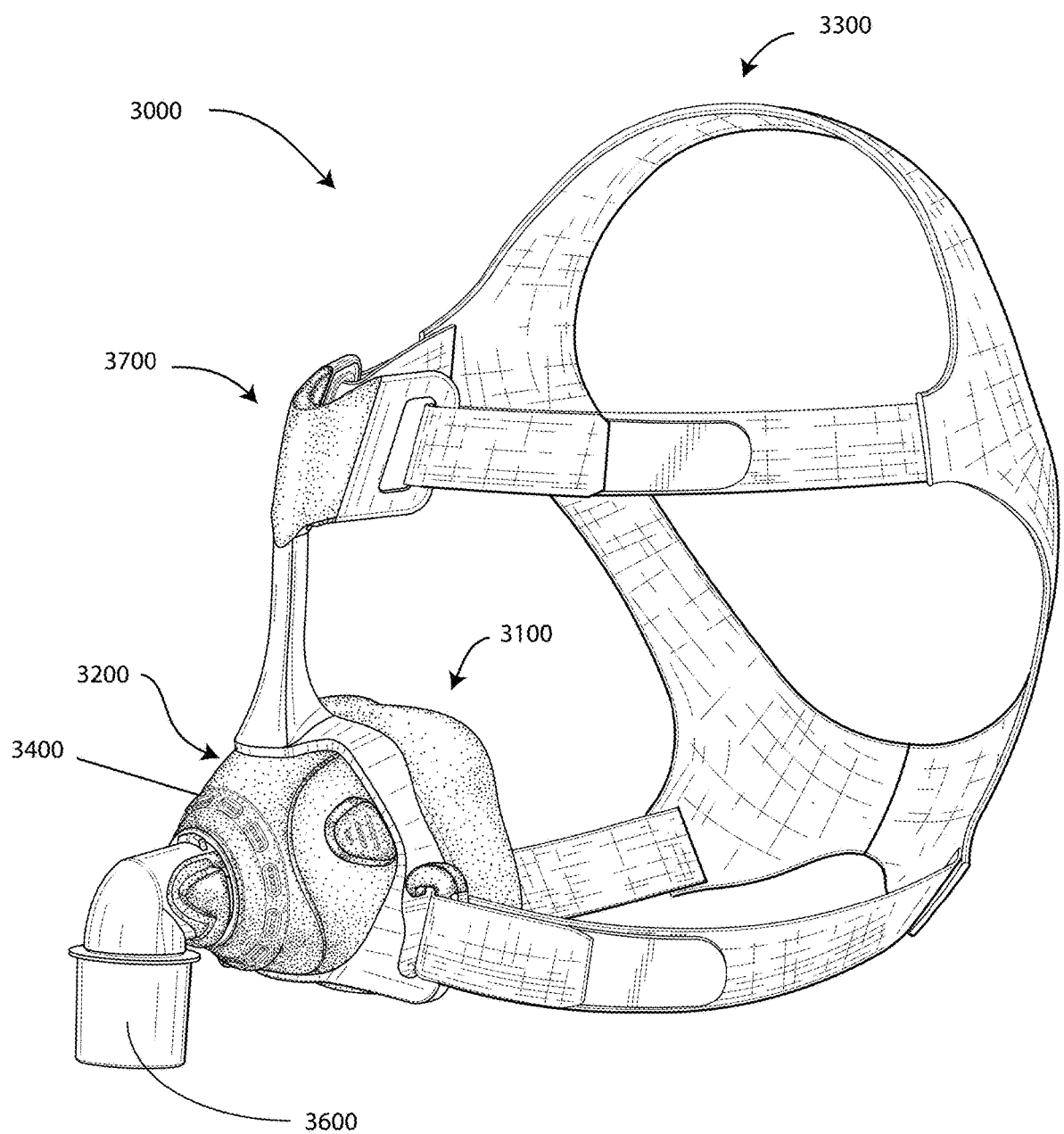

A non-invasive patient interface 3000 in accordance with one aspect of the present technology comprises (see FIG. 3A) the following functional aspects: a seal-forming structure 3100, a plenum chamber 3200, a positioning and stabilising structure 3300 and one form of connection port 3600 for connection to air circuit 4170. The patient interface may comprise a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.5 RPT Device

An RPT device 4000 in accordance with one aspect of the present technology comprises mechanical and pneumatic components 4100, electrical components 4200 and is configured to execute one or more algorithms 4300. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.5.1 RPT Device Mechanical & Pneumatic Components

An RPT device may comprise one or more of the following components in an integral unit. In an alternative form, one or more of the following components may be located as respective separate units.

5.5.1.1 Air Filter(s)

An RPT device in accordance with one form of the present technology may include an air filter 4110, or a plurality of air filters 4110.

Figure 4A:
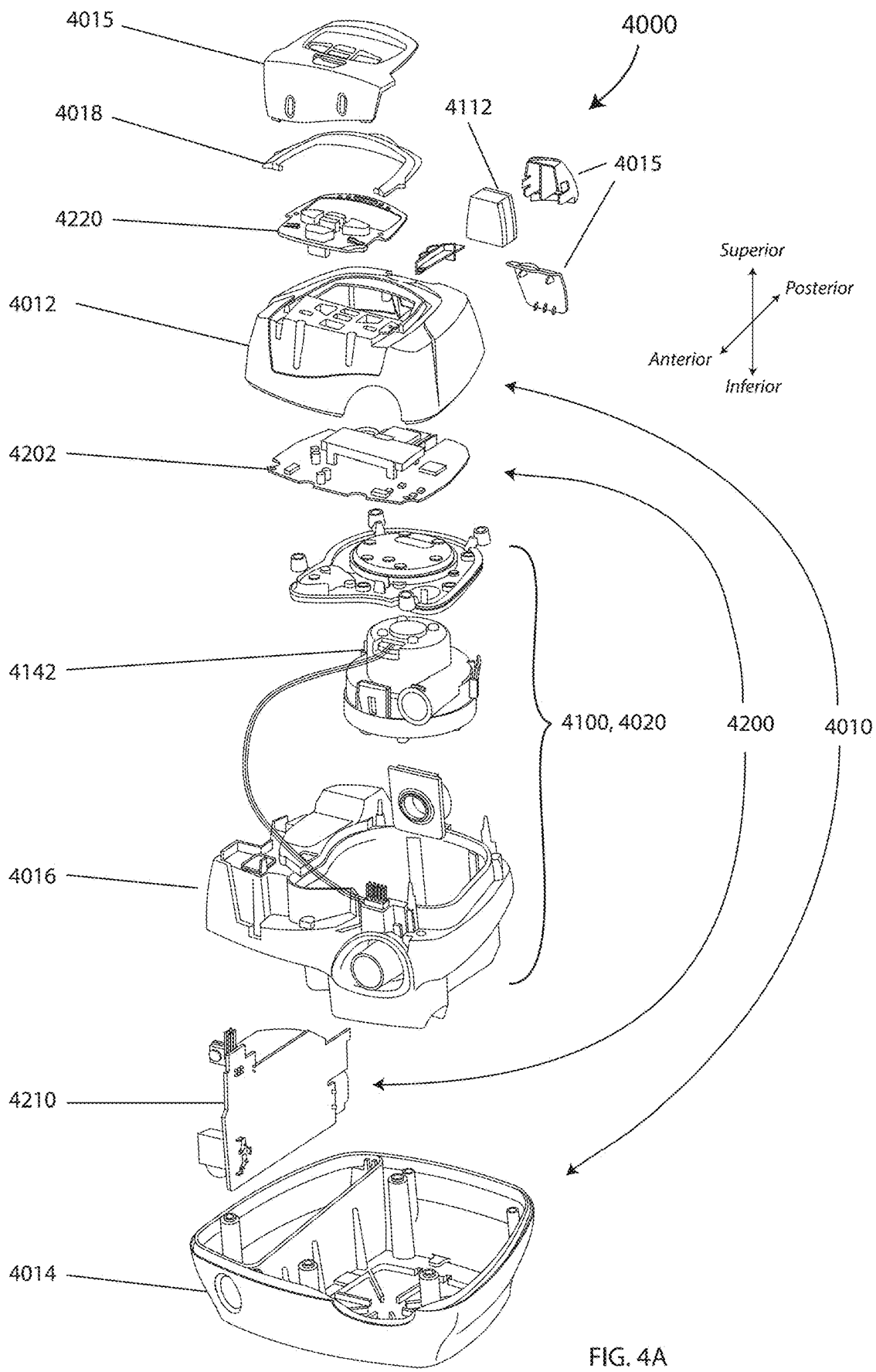
FIG. 4A shows an RPT device in accordance with one form of the present technology.
Figure 4B:
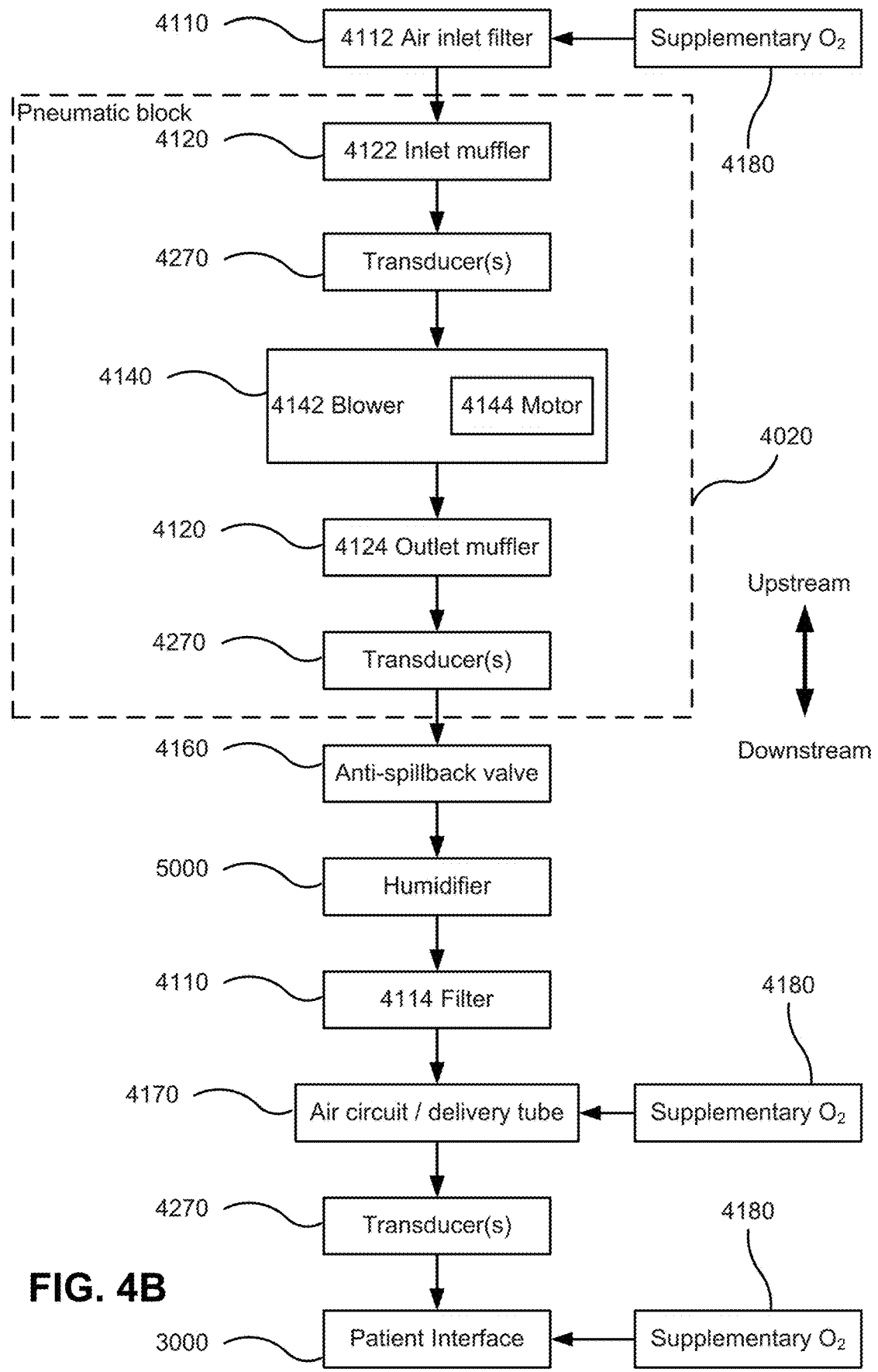
FIG. 4B is a schematic diagram of the pneumatic path of an RPT device in accordance with one form of the present technology. The directions of upstream and downstream are indicated.
Figure 4C:
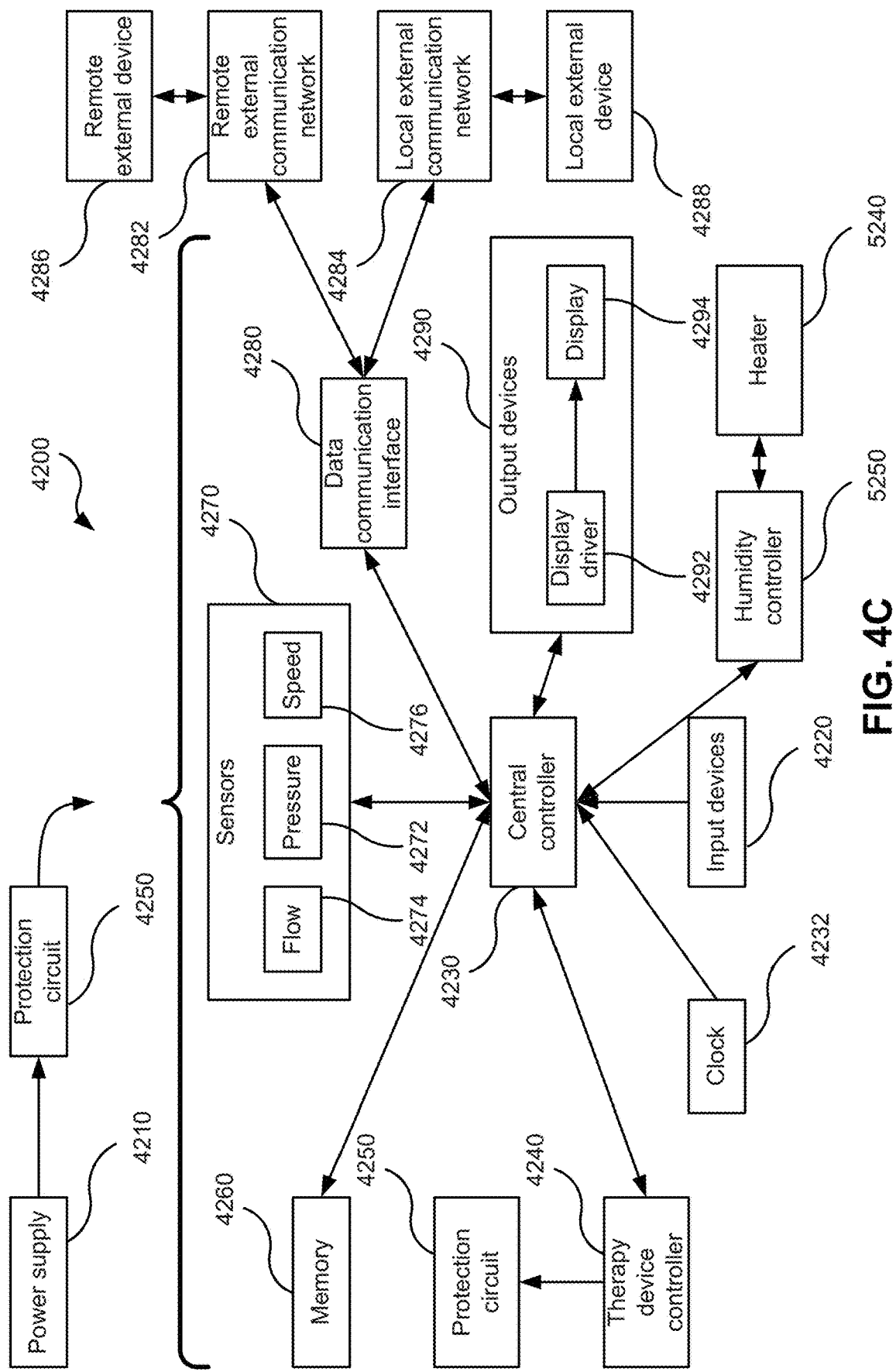
FIG. 4C is a schematic diagram of the electrical components of an RPT device in accordance with one form of the present technology.
Figure 4D:
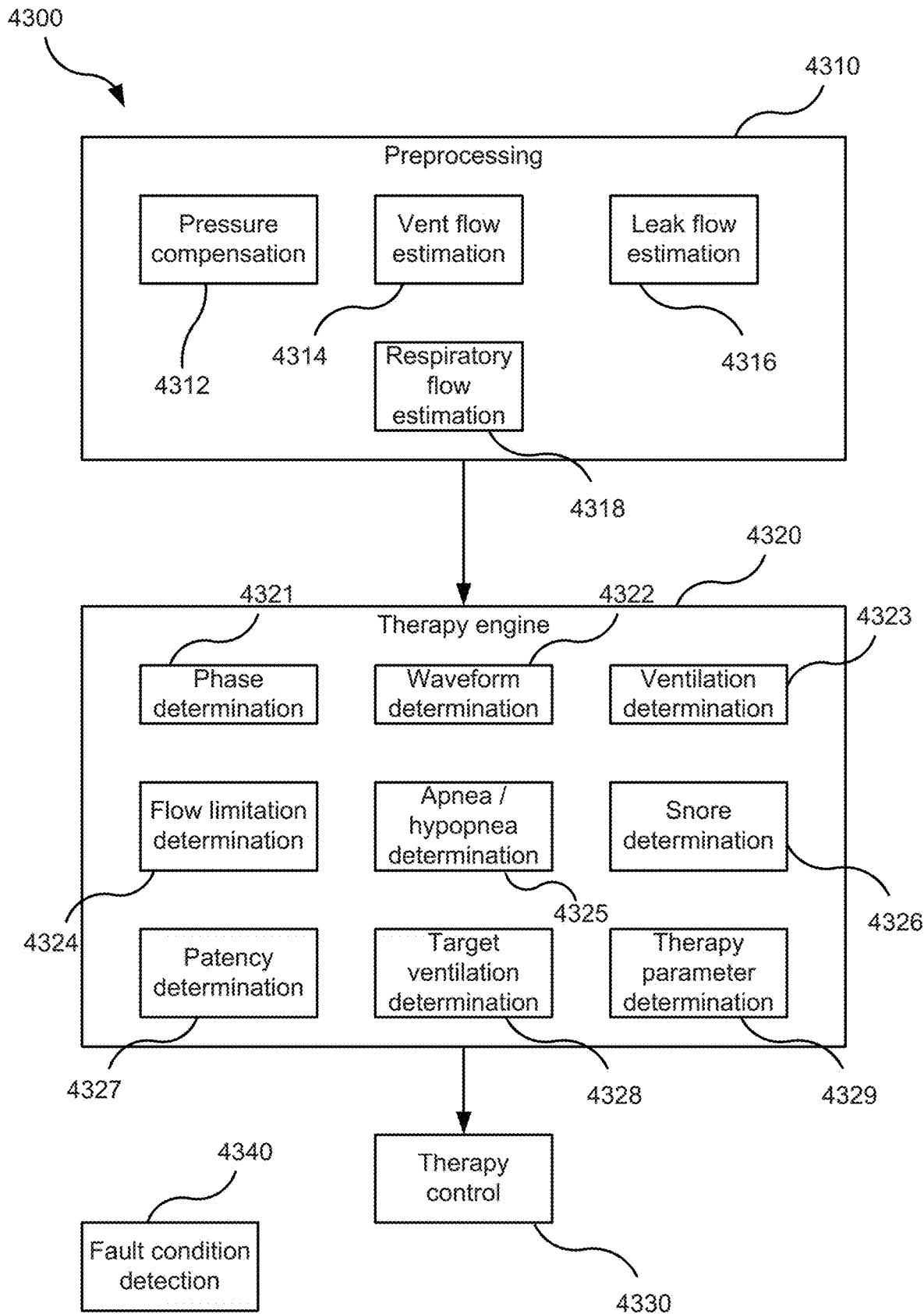
FIG. 4D is a schematic diagram of the algorithms implemented in an RPT device in accordance with one form of the present technology.
Figure 4E:
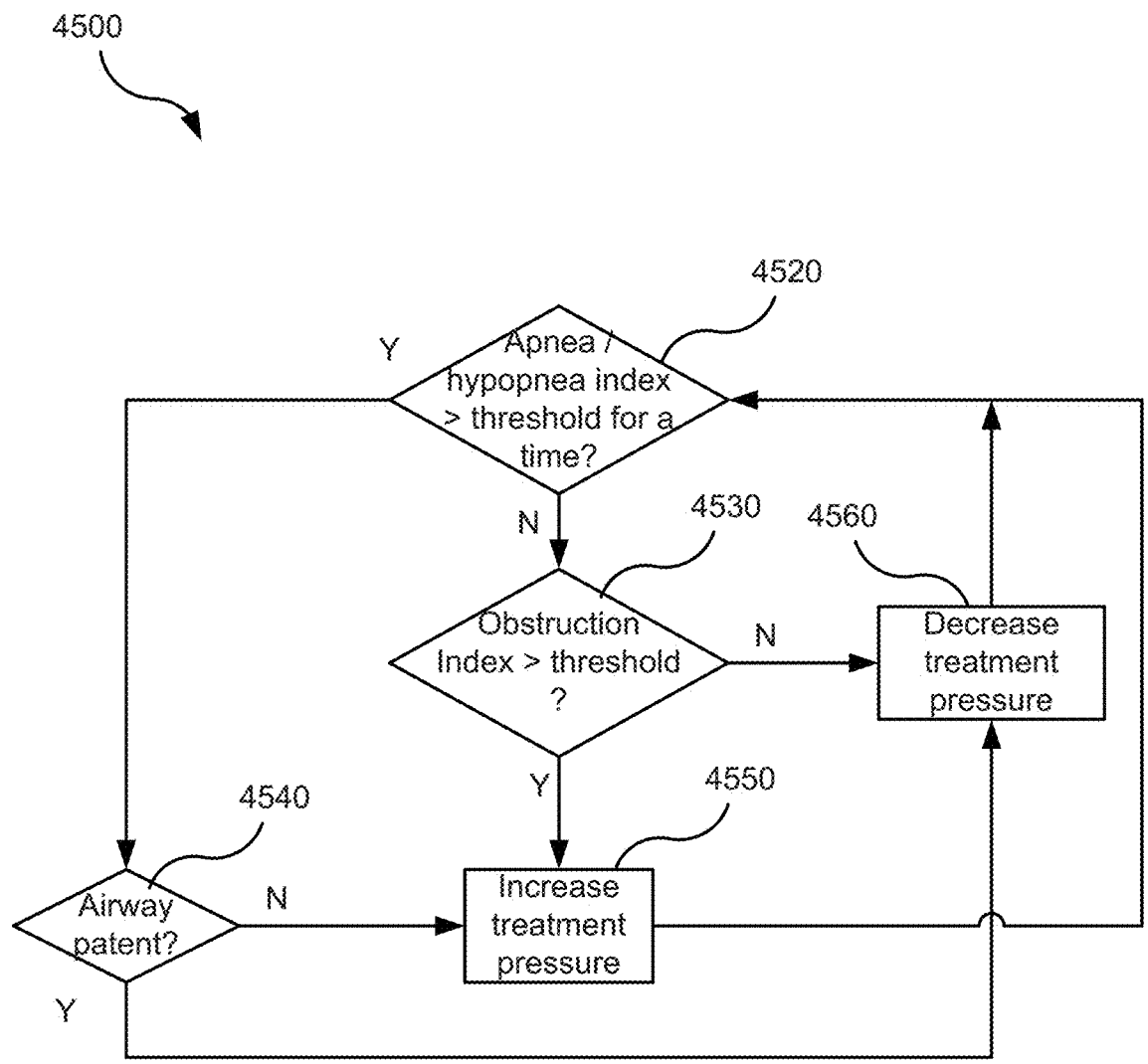
FIG. 4E is a flow chart illustrating a method carried out by the therapy engine module of FIG. 4D in accordance with one form of the present technology.

In one form, an inlet air filter 4112 is located at the beginning of the pneumatic path upstream of a pressure generator 4140. See FIG. 4B.

In one form, an outlet air filter 4114, for example an antibacterial filter, is located between an outlet of the pneumatic block 4020 and a patient interface 3000. See FIG. 4B.

5.5.1.2 Muffler(s)

In one form of the present technology, an inlet muffler 4122 is located in the pneumatic path upstream of a pressure generator 4140. See FIG. 4B.

In one form of the present technology, an outlet muffler 4124 is located in the pneumatic path between the pressure generator 4140 and a patient interface 3000. See FIG. 4B.

5.5.1.3 Pressure Generator 4140

In one form of the present technology, a pressure generator 4140 for producing a flow, or a supply, of air at positive pressure is a blower 4142. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O.

The pressure generator 4140 is under the control of the therapy device controller 4240.

In other forms, a pressure generator 4140 may be a motor-driven blower including a brushless DC motor with one or more impellers housed in a volute, a piston-driven pump, a pressure regulator connected to a high pressure source (e.g. compressed air reservoir), or a bellows.

5.5.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.5.1.4.1 Flow Rate Sensor

A flow rate sensor 4274 in accordance with the present technology may be based on a differential pressure transducer, for example, an SDP600 Series differential pressure transducer from SENSIRION.

One aspect of the present technology may relate to a sensor comprising a deformable material that can change its electrical properties and/or generate an electrical signal according to its configuration. For example, the deformable material may produce a signal indicative of one or more of a position or shape of the deformable material, wherein the signal may be electrical such as a current and/or a voltage.

One or more aspects of the produced signal may correlate to a flow of air, such as a flow rate and/or a pressure of the flow of air, for example as the flow of air travels through the air path of a respiratory therapy system. In one form, the sensor may be configured such that a flow of air deforms and/or moves a part of the sensor, wherein the deformation and/or movement occurs according to a flow rate and/or a pressure of the flow of air.

Thus, the sensor may comprise a sensing portion that is at least partly exposed to the flow of air in a portion of an air path. In an example, the sensing portion may be a sheet of electro-active polymer, wherein the sensing portion may deform according to a magnitude of the flow rate and/or the pressure of the air flow. The extent of deformation of the sensing portion may for example increase as the flow rate and/or the pressure of the air flow increases, and conversely, the deformation may decrease as the flow rate and/or the pressure decreases.

The sensor may comprise an exposed portion that is exposed to the air flow in a portion of an air path. The exposed portion may comprise a part of the sensing portion in some forms, although additionally, or alternatively, the exposed portion may comprise a rigid portion that is exposed to the air flow. Where the exposed portion comprises a rigid portion, the sensing portion may not be exposed to the air flow, although it is not necessary that the sensing portion is shielded from the air flow. The exposed portion may be open to the air flow in one of a number of possible methods, for example as a sheet extending from a periphery towards a centre of the air circuit (e.g. as shown in FIG. 10A), or as a sheet extending around a periphery of the air circuit. The exposed portion may be configured such that the flow of air may cause deformation of the exposed portion itself (e.g. wherein the exposed portion comprises a sensing portion), and/or the deformation of a separate sensing portion.

The deformation of the sensing portion may produce an electrical signal, for example in a form of a capacitance although in some configurations it may be also measured in current and/or a voltage. A bridge configuration may be used to measure a capacitance output of the sensor, which may comprise an ability to compensate for a change in temperature.

Advantageously, the sensing portion may be configured such that the electrical signal produced is at a higher sensitivity at a lower flow rate than at a higher flow rate. For example, the sensing portion may be a sheet that extends from a periphery of an air circuit to the centre of the air circuit. As a flow rate increases (e.g. from FIG. 10A to FIG. 10B), the deformation of the sensing portion may increase, deflecting the sensing portion towards a periphery of the air circuit, and thus decreasing an effective cross section area of the sensing portion that is exposed to the air flow.

In some forms, the sensing portion may in some form be covered or encased in silicone which may advantageously improve the sensor's resistance to moisture.

In one form, a signal representing a flow rate such as a total flow rate Qt from the flow rate sensor 4274 is received by the central controller 4230.

In some forms of the present technology, a flow rate may be estimated in lieu of a flow rate sensor. Instead, a blower 4142 may comprise a position sensor configured to generate a signal indicating a position of a deformable member. The flow rate generated by a chamber comprising a deformable member described in the present document may be proportional to the volume swept (or pumped) by the deformable member. Thus, an output of a position sensor (e.g. a Hall effect sensor) may be used as a measure of the flow rate of the chamber (and/or the blower).

Furthermore, advantageously, the output of the position sensor may also be used to control one or more deformable members in a closed-loop control system. Thus, a signal generated by the position sensor may be used in a plurality of control algorithms, potentially improving efficiency of the system.

5.5.1.4.2 Pressure Sensor

A pressure sensor 4272 in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

It will be understood that a pressure sensor 4272 according to one form of the present technology may comprise a deformable material as described above in relation to the flow rate sensor.

In one form, a signal from the pressure sensor 4272 is received by the central controller 4230.

5.5.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.5.1.5 Air Circuit

An air circuit 4170 in accordance with an aspect of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230 or a humidifier controller 5250. One example of an air circuit 4170 comprising a heated wire circuit is described in United States Patent Application No. US/2011/0023874, which is incorporated herewithin in its entirety by reference.

5.5.2 RPT Device Electrical Components

5.5.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.5.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.5.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280 and humidifier controller 5250.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.5.2.4 Clock

The RPT device 4000 may include a clock 4232 that is connected to the central controller 4230.

5.5.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.5.2.6 Protection Circuits

The one or more protection circuits 4250 in accordance with the present technology may comprise an electrical protection circuit, a temperature and/or pressure safety circuit.

5.5.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.5.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286.

The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.5.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.5.2.9.1 Display Driver

A display driver 4292 receives as an input the characters, symbols, or images intended for display on the display 4294, and converts them to commands that cause the display 4294 to display those characters, symbols, or images.

5.5.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.6 Humidifier 5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Respiratory Pressure Therapy (RPT): The application of a supply of air to an entrance to the airways at a treatment pressure that is typically positive with respect to atmosphere.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

5.7.2 RPT Device Parameters

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system. Respiratory flow rate, Qr, is the flow rate of air that is received into the patient's respiratory system.

Pressure: Force per unit area. Pressure may be measured in a range of units, including $cmH_2O$, $g-f/cm^2$ and hectopascal. 1 cmH$_2$O is equal to 1 g-f/cm$^2$ and is approximately 0.98 hectopascal. In this specification, unless otherwise stated, pressure is given in units of cmH$_2$O. The pressure in the patient interface is given the symbol Pm, while the treatment pressure, which represents a target value to be achieved by the mask pressure Pm at the current instant of time, is given the symbol Pt.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as 10$^{12}$ watt.

Sound Pressure: The local deviation from ambient pressure at a given time instant as a result of a sound wave travelling through a medium. Sound pressure is usually given in decibels SPL, that is, decibels relative to a reference pressure, normally taken as 20×10$^{-6}$ Pascal (Pa), considered the threshold of human hearing.

5.7.3 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 5.9 REFERENCE SIGNS LIST | |
| --- | --- |
| Reference Text | Reference No. |
| patient | 1000 |
| bed partner | 1100 |
| patient interface | 3000 |
| seal - forming structure | 3100 |
| plenum chamber | 3200 |
| structure | 3300 |
| connection port | 3600 |
| forehead support | 3700 |
| rpt device | 4000 |

5.9 REFERENCE SIGNS LIST

| Reference Text | Reference No. |
|---|---|
| external housing | 4010 |
| upper portion | 4012 |
| lower portion | 4014 |
| panel | 4015 |
| chassis | 4016 |
| handle | 4018 |
| pneumatic block | 4020 |
| pneumatic component | 4100 |
| air filter | 4110 |
| inlet air filter | 4112 |
| outlet air filter | 4114 |
| inlet muffler | 4122 |
| outlet muffler | 4124 |
| pressure generator | 4140 |
| blower | 4142 |
| blower | 4142 |
| motor | 4144 |
| air circuit | 4170 |
| pressure sensor | 4172 |
| electrical component | 4200 |
| PCBA | 4202 |
| power supply | 4210 |
| input device | 4220 |
| central controller | 4230 |
| clock | 4232 |
| therapy device controller | 4240 |
| protection circuit | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithm | 4300 |
| therapy control module | 4330 |
| humidifier | 5000 |
| humidifier inlet | 5002 |
| humidifier outlet | 5004 |
| humidifier base | 5006 |
| humidifier reservoir | 5110 |
| humidifier reservoir dock | 5130 |
| heating element | 5240 |
| humidifier controller | 5250 |
| deformable member | 6010 |
| deformable member | 6011 |
| elastic portion | 6012 |
| controllable portion | 6014 |
| chamber | 6020 |
| chamber | 6021 |
| movable wall | 6030 |
| chamber wall | 6040 |
| blower inlet | 6050 |
| inlet valve | 6052 |
| inlet valve deformable portion | 6054 |
| blower outlet | 6060 |
| outlet valve | 6062 |
| outlet valve deformable portion | 6064 |
| deformable member | 6065 |
| first spring | 6072 |
| second spring | 6074 |
| actuator | 6080 |
| deformable member | 6110 |
| chamber | 6120 |
| chamber | 6121 |
| chamber wall | 6140 |
| inlet | 6150 |
| outlet | 6160 |
| actuator | 6180 |
| first air flow rate waveform | 7010 |
| second air flow rate waveform | 7020 |
| combined air flow rate waveform | 7030 |
| deformable member | 8010 |
| chamber | 8020 |
| inlet | 8050 |
| outlet | 8060 |
| chamber | 8120 |
| inlet | 8150 |
| outlet | 8160 |
| deformable member | 8210 |
| chamber | 8220 |
| inlet | 8250 |
| outlet | 8260 |
| chamber | 8320 |
| inlet | 8350 |
| outlet | 8360 |
| deformable member | 9010 |
| chamber | 9020 |
| slot | 9030 |
| first housing | 9042 |
| second housing | 9044 |
| chamber inlet | 9050 |
| inlet valve | 9052 |
| chamber outlet | 9060 |
| outlet valve | 9062 |
| blower outlet | 9070 |
| outlet collector | 9072 |
| second chamber | 9120 |
| chamber inlet | 9150 |
| inlet valve | 9152 |
| chamber outlet | 9160 |
| outlet valve | 9162 |
| deformable member | 11010 |
| chamber | 11020 |
| wall | 11040 |
| inlet valve | 11052 |
| deformable member | 11054 |
| outlet valve | 11062 |
| deformable member | 11064 |
| electromagnet | 11080 |
| electromagnet | 11082 |
| electromagnet | 11084 |

The invention claimed is:

1. A blower for producing a flow of air at a positive pressure, the blower comprising:
 a housing;
 one or more air inlets;
 a plurality of chambers in the housing and arranged in parallel, each chamber configured to receive air from one or more of the one or more air inlets;
 a set of deformable members, each deformable member being convertible to a first configuration and a second configuration by electrical energy; and
 one or more air outlets, each chamber configured to deliver air from the blower through one or more of the one or more air outlets;
 wherein each of the plurality of chambers is configured to produce the flow of air at a positive pressure through the one or more air outlets by conversion of the set of deformable members between the first configuration and the second configuration;
 a controller in a form of a processor programmed to control application of electric energy to operate at least a first deformable member and a second deformable member of the set of deformable members out of phase with each other;

wherein the first deformable member divides the housing into a first chamber and a second chamber of the plurality of chambers, the first chamber includes a first air inlet of the one or more air inlets and a first air outlet of the one or more air outlets; and wherein the first chamber is isolated from the second chamber across the first deformable member such that the first air inlet and the first air outlet are disposed on a same side of the first deformable member, and airflow through the first chamber between the first air inlet and the first air outlet bypasses the second chamber.

2. The blower as claimed in claim 1, wherein the set of deformable members comprises an electroactive polymer.

3. The blower as claimed in claim 1, wherein the set of deformable members comprises a membrane.

4. The blower as claimed in claim 3, wherein a periphery of the membrane is secured to the housing.

5. The blower as claimed in claim 1, wherein the at least one of the set of deformable members is convertible between configurations by application of a predetermined magnitude of electrical energy.

6. The blower as claimed in claim 1, wherein the electrical energy is applied as a current through the one of the set of deformable members.

7. The blower as claimed in claim 1, further comprising a capacitive member configured to maintain at least one of the set of deformable members in a configuration by retaining electrical energy therein.

8. The blower as claimed in claim 1, wherein at least one of the set of deformable members is convertible to a third configuration between the first configuration and the second configuration.

9. The blower as claimed in claim 1, wherein all of the plurality of chambers are uniformly sized.

10. The blower as claimed in claim 1, further comprising a chamber arranged in series to one of the plurality of chambers.

11. The blower as claimed in claim 1, further comprising a valve comprising a deformable member.

12. The blower as claimed in claim 1, wherein the processor is configured to operate the first chamber and the second chamber of the plurality of chambers such that they produce air flows in a manner whereby only a fall period of the first chamber overlaps with a rise period of the second chamber.

13. The blower as claimed in claim 1, wherein there are two times more chambers of the plurality of chambers than of the set of deformable members.

14. The blower as claimed in claim 1, wherein the first deformable member is constructed at least partially from silicone, and prevents fluid flow from the first chamber to the second chamber.

15. The blower as claimed in claim 1, wherein the flow of air through each of the first chamber and the second chamber in a direction substantially parallel to a first axis, and wherein the first deformable member moves between the first configuration and the second configuration along a second axis substantially transverse to the first axis.

16. The blower as claimed in claim 1, wherein the first deformable member is configured to operate 90° out of phase with respect to the second deformable member.

17. The blower as claimed in claim 1, wherein the first chamber and the second chamber are 180° out of phase with each other.

18. The blower as claimed in claim 1, further comprising a first one-way valve and a second one-way valve, wherein the first one-way valve is disposed in the first air inlet and the second one-way valve is disposed in the first air outlet, the first one-way valve and the second one-way valve, together with the first deformable member, are controlled using the processor, wherein when the first deformable member is moving from the first configuration toward the second configuration, the first one-way valve is closed and the second one-way valve is open, and wherein when the first deformable member is moving from the second configuration toward the first configuration, the first one-way valve is open and the second one-way valve is closed.

19. The blower as claimed in claim 1, wherein
the plurality of chambers includes the first chamber, the second chamber, a third chamber, and a fourth chamber;
the one or more air inlets includes the first air inlet, a second air inlet, a third air inlet, and a fourth air inlet;
the one or more air outlets includes the first air outlet, a second air outlet, a third air outlet, and a fourth air outlet; and
the housing includes
a first sub-housing including the first deformable member dividing the first sub-housing into the first chamber and the second chamber, the first chamber includes the first air inlet and the first air outlet, the second chamber includes the second air inlet and the second air outlet, wherein the first chamber is isolated from the second chamber by the first deformable member so that airflow from the first air inlet to the first air outlet bypasses the second chamber and airflow from the second air inlet to the second air outlet bypasses the first chamber, and
a second sub-housing including the second deformable member dividing the second sub-housing into the third chamber and the fourth chamber, the third chamber includes the third air inlet and the third air outlet, the fourth chamber includes the fourth air inlet and the fourth air outlet, wherein the third chamber is isolated from the fourth chamber by the second deformable member so that airflow from the third air inlet to the third air outlet bypasses the fourth chamber and airflow from the fourth air inlet to the fourth air outlet bypasses the third chamber,
wherein the first sub-housing is isolated from the second sub-housing; and
wherein the first deformable member is 90° out of phase with the second deformable member, and each of the chambers sharing a sub-housing is 180° out of phase with each other.

20. The blower as claimed in claim 1, wherein the set of deformable members at least partly defines at least one of the plurality of chambers.

21. The blower as claimed in claim 20, wherein a deformable member of the set of deformable members at least partly defines at least two of the plurality of chambers.

22. The blower as claimed in claim 1, wherein the controller is configured to vary application of electrical energy to the set of deformable members according to a measure of pressure.

23. The blower as claimed in claim 22, wherein the measure of pressure is indicative of a pressure at the one or more air outlets.

24. The blower as claimed in claim 22, wherein the controller is configured to vary application of electrical energy to the set of deformable members to reduce a difference between the measure of pressure and a target pressure.

25. The blower as claimed in claim 24, wherein the target pressure is a predetermined pressure.

26. The blower as claimed in claim 24, wherein the controller is configured to vary a frequency of application of electrical energy to reduce the difference between the measure of pressure and the target pressure.

* * * * *